(12) United States Patent
Zhu et al.

(10) Patent No.: US 9,464,286 B2
(45) Date of Patent: Oct. 11, 2016

(54) HIGH THROUGHPUT GENERATION AND AFFINITY MATURATION OF HUMANIZED ANTIBODY

(75) Inventors: Li Zhu, Palo Alto, CA (US);
Shuanghong Wei, San Jose, CA (US);
Shaobing B. Hua, Cupertino, CA (US)

(73) Assignee: Adimab, LLC, Lebanon, NH (US)

( * ) Notice: Subject to any disclaimer, the term of this patent is extended or adjusted under 35 U.S.C. 154(b) by 0 days.

(21) Appl. No.: 11/480,037

(22) Filed: Jun. 29, 2006

(65) Prior Publication Data

US 2006/0246515 A1    Nov. 2, 2006

Related U.S. Application Data

(63) Continuation of application No. 10/460,595, filed on Jun. 11, 2003, now abandoned.

(60) Provisional application No. 60/403,296, filed on Aug. 12, 2002.

(51) Int. Cl.
*C12Q 1/68* (2006.01)
*C12N 15/10* (2006.01)

(52) U.S. Cl.
CPC ....... *C12N 15/1041* (2013.01); *C12N 15/1062* (2013.01); *C12N 15/1086* (2013.01)

(58) Field of Classification Search
None
See application file for complete search history.

(56) References Cited

U.S. PATENT DOCUMENTS

| | | |
|---|---|---|
| 4,230,685 A | 10/1980 | Senyei et al. |
| 4,452,773 A | 6/1984 | Molday |
| 4,661,454 A | 4/1987 | Botstein et al. |
| 4,770,183 A | 9/1988 | Groman et al. |
| 4,816,567 A | 3/1989 | Cabilly et al. |
| 4,946,778 A | 8/1990 | Ladner et al. |
| 4,959,317 A | 9/1990 | Sauer |
| 5,118,605 A | 6/1992 | Urdea |
| 5,223,409 A | 6/1993 | Ladner et al. |
| 5,283,173 A | 2/1994 | Fields et al. |
| 5,380,833 A | 1/1995 | Urdea |
| 5,506,121 A | 4/1996 | Skerra et al. |
| 5,525,490 A | 6/1996 | Erickson et al. |
| 5,530,101 A * | 6/1996 | Queen et al. |
| 5,565,332 A | 10/1996 | Hoogenboom et al. |
| 5,571,698 A | 11/1996 | Ladner et al. |
| 5,618,920 A | 4/1997 | Robinson et al. |
| 5,658,727 A | 8/1997 | Barbas et al. |
| 5,688,666 A | 11/1997 | Bass et al. |
| 5,695,941 A | 12/1997 | Brent et al. |
| 5,712,120 A | 1/1998 | Rodriguez et al. |
| 5,723,323 A | 3/1998 | Kauffman et al. |
| 5,723,584 A | 3/1998 | Schatz |
| 5,733,743 A | 3/1998 | Johnson et al. |
| 5,739,281 A | 4/1998 | Thogersen et al. |
| 5,750,373 A | 5/1998 | Garrard et al. |
| 5,767,260 A | 6/1998 | Whitlow et al. |
| 5,780,279 A | 7/1998 | Matthews et al. |
| 5,798,208 A | 8/1998 | Crea |
| 5,811,238 A | 9/1998 | Stemmer et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,830,663 A | 11/1998 | Embleton et al. |
| 5,837,242 A | 11/1998 | Holliger et al. |
| 5,837,500 A | 11/1998 | Ladner et al. |
| 5,840,479 A | 11/1998 | Little et al. |
| 5,846,765 A | 12/1998 | Matthews et al. |
| 5,858,657 A | 1/1999 | Winter et al. |
| 5,858,671 A | 1/1999 | Jones |
| 5,863,765 A | 1/1999 | Berry et al. |
| 5,866,344 A | 2/1999 | Georgiou |
| 5,869,250 A | 2/1999 | Cheng et al. |
| 5,871,907 A | 2/1999 | Winter et al. |
| 5,872,215 A | 2/1999 | Osbourne et al. |

(Continued)

FOREIGN PATENT DOCUMENTS

| | | |
|---|---|---|
| DE | 19624562 A1 | 1/1998 |
| EP | 0404097 A2 | 12/1990 |

(Continued)

OTHER PUBLICATIONS

Co et al. Nature, 351:501-502, Jun. 6, 1991.*
Fundamental Immunology, William E. Paul, ed., 3rd Edition, 1993, pp. 292-295.*
Rudikoff et al. Proc. Natl. Acad. Sci. USA, 79:1979-1983, Mar. 1982.*
Radar et al. Proc. Natl. Acad. Sci. USA, 95:8910-8915, Jul. 1998.*
MacCallum et al. J. Mol. Biol., 262, 732-745, 1996.*
Casset et al. Biochemical and Biophysical Research Communications, 307:198-205, 2003.*

(Continued)

*Primary Examiner* — Laura B Goddard
*Assistant Examiner* — Meera Natarajan
(74) *Attorney, Agent, or Firm* — Brenda Herschbach Jarrell; Robert N. Sahr; Choate Hall & Stewart LLP

(57) ABSTRACT

Compositions, methods, and kits are provided for efficiently generating and screening humanized antibody with high affinity against a specific antigen. The library of humanized antibody is generated by mutagenizing a chimeric antibody template that combines human antibody framework and antigen binding sites of a non-human antibody. Alternatively, the library of humanized antibody is generated by grafting essential antigen-recognition segment(s) such as CDRs of the non-human antibody into the corresponding position(s) of each member of a human antibody library. This library of humanized antibody is then screened for high affinity binding toward a specific antigen in vivo in organism such as yeast or in vitro using techniques such as ribosome display or mRNA display. The overall process can be efficiently performed in a high throughput and automated manner, thus mimicking the natural process of antibody affinity maturation.

18 Claims, 13 Drawing Sheets

(56) References Cited

U.S. PATENT DOCUMENTS

| | | | |
|---|---|---|---|
| 5,874,239 A | 2/1999 | Schatz |
| 5,885,793 A | 3/1999 | Griffiths et al. |
| 5,888,773 A | 3/1999 | Jost et al. |
| 5,917,018 A | 6/1999 | Thogersen et al. |
| 5,922,545 A | 7/1999 | Mattheakis et al. |
| 5,928,868 A | 7/1999 | Liu et al. |
| 5,932,433 A | 8/1999 | Schatz |
| 5,935,831 A | 8/1999 | Quax et al. |
| 5,948,620 A | 9/1999 | Hurd et al. |
| 5,955,275 A | 9/1999 | Kamb et al. |
| 5,962,255 A | 10/1999 | Griffiths et al. |
| 5,965,368 A | 10/1999 | Vidal et al. |
| 5,969,108 A | 10/1999 | McCafferty et al. |
| 5,976,862 A | 11/1999 | Kauffman et al. |
| 5,994,515 A | 11/1999 | Hoxie |
| 5,994,519 A | 11/1999 | Osbourn et al. |
| 6,010,884 A | 1/2000 | Griffiths et al. |
| 6,017,732 A | 1/2000 | Jespers et al. |
| 6,022,729 A | 2/2000 | Steinbuchel et al. |
| 6,027,910 A | 2/2000 | Klis et al. |
| 6,040,136 A | 3/2000 | Garrard et al. |
| 6,057,098 A | 5/2000 | Buechler et al. |
| 6,057,101 A | 5/2000 | Nandabalan et al. |
| 6,072,036 A | 6/2000 | Marasco et al. |
| 6,072,039 A | 6/2000 | Haase et al. |
| 6,083,693 A | 7/2000 | Nandabalan et al. |
| 6,103,493 A | 8/2000 | Skerra et al. |
| 6,114,147 A | 9/2000 | Frenken et al. |
| 6,132,963 A | 10/2000 | Brent et al. |
| 6,140,471 A | 10/2000 | Johnson et al. |
| 6,159,705 A | 12/2000 | Trueheart et al. |
| 6,171,795 B1 | 1/2001 | Korman et al. |
| 6,172,197 B1 | 1/2001 | McCafferty et al. |
| 6,180,336 B1 | 1/2001 | Osbourn et al. |
| 6,187,535 B1 | 2/2001 | LeGrain et al. |
| 6,200,759 B1 | 3/2001 | Dove et al. |
| 6,225,447 B1 | 5/2001 | Winter et al. |
| 6,248,516 B1 | 6/2001 | Winter et al. |
| 6,265,552 B1 | 7/2001 | Schatz |
| 6,291,158 B1 | 9/2001 | Winter et al. |
| 6,291,159 B1 | 9/2001 | Winter et al. |
| 6,291,160 B1 | 9/2001 | Lerner et al. |
| 6,291,161 B1 | 9/2001 | Lerner et al. |
| 6,291,650 B1 | 9/2001 | Winter et al. |
| 6,300,064 B1 | 10/2001 | Knappik et al. |
| 6,300,065 B1 | 10/2001 | Kieke et al. |
| 6,312,916 B1 | 11/2001 | Kopetzki et al. |
| 6,319,690 B1 | 11/2001 | Little et al. |
| 6,342,588 B1 | 1/2002 | Osbourn et al. |
| 6,358,733 B1 | 3/2002 | Motwani et al. |
| 6,368,813 B1 | 4/2002 | Reznik et al. |
| 6,406,863 B1 * | 6/2002 | Zhu et al. |
| 6,410,246 B1 | 6/2002 | Zhu et al. |
| 6,410,271 B1 | 6/2002 | Zhu et al. |
| 6,420,113 B1 | 7/2002 | Buechler et al. |
| 6,423,538 B1 | 7/2002 | Wittrup et al. |
| 6,489,123 B2 | 12/2002 | Osbourn et al. |
| 6,492,107 B1 | 12/2002 | Kauffman et al. |
| 6,492,123 B1 | 12/2002 | Holliger et al. |
| 6,492,160 B1 | 12/2002 | Griffiths et al. |
| 6,521,404 B1 | 2/2003 | Griffiths et al. |
| 6,531,580 B1 | 3/2003 | Huse et al. |
| 6,544,731 B1 | 4/2003 | Griffiths et al. |
| 6,545,142 B1 | 4/2003 | Winter et al. |
| 6,555,313 B1 | 4/2003 | Griffiths et al. |
| 6,569,641 B1 | 5/2003 | Kauffman et al. |
| 6,582,915 B1 | 6/2003 | Griffiths et al. |
| 6,589,527 B1 | 7/2003 | Winter et al. |
| 6,589,741 B2 | 7/2003 | Pluckthun et al. |
| 6,593,081 B1 | 7/2003 | Griffiths et al. |
| 6,610,472 B1 * | 8/2003 | Zhu et al. |
| 6,653,443 B2 | 11/2003 | Zhang et al. |
| 6,664,048 B1 | 12/2003 | Wanker et al. |
| 6,680,192 B1 | 1/2004 | Lerner et al. |
| 6,696,245 B2 | 2/2004 | Winter et al. |
| 6,696,248 B1 | 2/2004 | Knappik et al. |
| 6,696,251 B1 | 2/2004 | Wittrup et al. |
| 6,699,658 B1 | 3/2004 | Wittrup et al. |
| 6,706,484 B1 | 3/2004 | Knappik et al. |
| 6,750,042 B2 | 6/2004 | Summers et al. |
| 6,753,136 B2 | 6/2004 | Lohning |
| 6,806,079 B1 | 10/2004 | McCafferty et al. |
| 6,828,422 B1 | 12/2004 | Achim et al. |
| 6,833,441 B2 * | 12/2004 | Wang et al. |
| 6,841,359 B2 | 1/2005 | Szostak et al. |
| 6,846,634 B1 | 1/2005 | Tomlinson et al. |
| 6,916,605 B1 | 7/2005 | McCafferty et al. |
| 6,919,183 B2 | 7/2005 | Fandl et al. |
| 6,969,586 B1 | 11/2005 | Lerner et al. |
| 7,005,503 B2 | 2/2006 | Zhu et al. |
| 7,037,706 B1 | 5/2006 | Barrett et al. |
| 7,063,943 B1 | 6/2006 | McCafferty et al. |
| 7,083,945 B1 | 8/2006 | Chen et al. |
| 7,094,571 B2 | 8/2006 | Harvey et al. |
| 7,112,439 B2 | 9/2006 | Johnson et al. |
| 7,118,915 B2 | 10/2006 | Vogt et al. |
| 7,138,253 B2 | 11/2006 | Szostak et al. |
| 7,166,423 B1 | 1/2007 | Miltenyi et al. |
| 7,172,877 B2 | 2/2007 | Ting |
| 7,189,841 B2 | 3/2007 | Lerner et al. |
| 7,208,293 B2 | 4/2007 | Ladner et al. |
| 7,229,757 B2 | 6/2007 | Barrett et al. |
| 7,252,998 B2 | 8/2007 | Skerra et al. |
| 7,282,475 B2 | 10/2007 | Porter et al. |
| 7,302,146 B2 | 11/2007 | Turner et al. |
| 7,315,019 B2 | 1/2008 | Turner et al. |
| 7,335,019 B2 | 2/2008 | Suzuki et al. |
| 7,355,008 B2 | 4/2008 | Stavenhagen et al. |
| 7,371,849 B2 | 5/2008 | Honda et al. |
| 7,435,553 B2 | 10/2008 | Fandl et al. |
| 7,465,787 B2 | 12/2008 | Wittrup et al. |
| 7,569,357 B2 | 8/2009 | Kranz et al. |
| 7,700,302 B2 | 4/2010 | Hua et al. |
| 8,691,225 B2 | 4/2014 | Schoeberl et al. |
| 8,877,688 B2 | 11/2014 | Vasquez et al. |
| 8,927,694 B2 | 1/2015 | McDonagh et al. |
| 8,961,966 B2 | 2/2015 | Schoeberl et al. |
| 2002/0004215 A1 | 1/2002 | Osbourn et al. |
| 2002/0069421 A1 | 6/2002 | Hale et al. |
| 2002/0155157 A1 | 10/2002 | Luo et al. |
| 2002/0169284 A1 | 11/2002 | Ashkenazi et al. |
| 2002/0197691 A1 | 12/2002 | Sugiyama |
| 2003/0083474 A1 | 5/2003 | Schmidt |
| 2003/0092073 A1 | 5/2003 | Ambrosius et al. |
| 2003/0104524 A1 | 6/2003 | Summers et al. |
| 2003/0114659 A1 | 6/2003 | Winter et al. |
| 2003/0130496 A1 | 7/2003 | Winter et al. |
| 2003/0148372 A1 | 8/2003 | Tomlinson et al. |
| 2003/0165988 A1 | 9/2003 | Hua et al. |
| 2003/0190674 A1 | 10/2003 | Griffiths et al. |
| 2003/0228302 A1 | 12/2003 | Crea |
| 2003/0232333 A1 | 12/2003 | Ladner |
| 2003/0232395 A1 | 12/2003 | Hufton |
| 2004/0038921 A1 | 2/2004 | Kreutzer et al. |
| 2004/0082012 A1 | 4/2004 | Busch et al. |
| 2004/0110941 A2 | 6/2004 | Winter et al. |
| 2004/0146976 A1 | 7/2004 | Wittrup et al. |
| 2004/0157214 A1 | 8/2004 | McCafferty et al. |
| 2004/0157215 A1 | 8/2004 | McCafferty et al. |
| 2004/0175756 A1 | 9/2004 | Kolkman et al. |
| 2004/0190333 A1 | 9/2004 | Yuan et al. |
| 2004/0197347 A1 | 10/2004 | Sykes et al. |
| 2004/0197866 A1 | 10/2004 | Johnson et al. |
| 2004/0209317 A1 | 10/2004 | Ting |
| 2004/0219611 A1 | 11/2004 | Racher |
| 2004/0248298 A1 | 12/2004 | Schutz et al. |
| 2004/0259162 A1 | 12/2004 | Kappel et al. |
| 2005/0009028 A1 | 1/2005 | Heintz et al. |
| 2005/0019827 A1 | 1/2005 | Diller et al. |
| 2005/0048512 A1 | 3/2005 | Kolkman et al. |
| 2005/0048545 A1 | 3/2005 | Cull et al. |
| 2005/0053591 A1 | 3/2005 | Pun |
| 2005/0053973 A1 | 3/2005 | Kolkman et al. |
| 2005/0058661 A1 | 3/2005 | Sykes et al. |

(56) References Cited

U.S. PATENT DOCUMENTS

| | | |
|---|---|---|
| 2005/0089932 A1 | 4/2005 | Kolkman et al. |
| 2005/0164301 A1 | 7/2005 | Kolkman et al. |
| 2005/0176070 A1 | 8/2005 | Auton |
| 2005/0191710 A1 | 9/2005 | Hanrahan et al. |
| 2005/0202512 A1 | 9/2005 | Tomlinson et al. |
| 2005/0221384 A1 | 10/2005 | Kolkman et al. |
| 2005/0233389 A1 | 10/2005 | Ting et al. |
| 2005/0255462 A1 | 11/2005 | Barrett et al. |
| 2006/0003334 A1 | 1/2006 | Achim et al. |
| 2006/0008883 A1 | 1/2006 | Lazar et al. |
| 2006/0019260 A1 | 1/2006 | Lerner et al. |
| 2006/0024676 A1 | 2/2006 | Uhlmann et al. |
| 2006/0046261 A1 | 3/2006 | Porter et al. |
| 2006/0046285 A1 | 3/2006 | Watzele et al. |
| 2006/0052294 A1 | 3/2006 | Otto |
| 2006/0061754 A1 | 3/2006 | Turner et al. |
| 2006/0061755 A1 | 3/2006 | Turner et al. |
| 2006/0062531 A1 | 3/2006 | Turner et al. |
| 2006/0063264 A1 | 3/2006 | Turner et al. |
| 2006/0106199 A1 | 5/2006 | Erdmann et al. |
| 2006/0166252 A1 | 7/2006 | Ladner et al. |
| 2006/0172281 A1 | 8/2006 | Schutz et al. |
| 2006/0211087 A1 | 9/2006 | Roosild et al. |
| 2006/0234302 A1 | 10/2006 | Hoet et al. |
| 2006/0257937 A1 | 11/2006 | Ladner |
| 2007/0031879 A1 | 2/2007 | Ley et al. |
| 2007/0037216 A1 | 2/2007 | Johnson et al. |
| 2007/0082330 A1 | 4/2007 | Barrett et al. |
| 2007/0099267 A1 | 5/2007 | Harvey et al. |
| 2007/0141548 A1 | 6/2007 | Kohl et al. |
| 2007/0258954 A1 | 11/2007 | Iverson et al. |
| 2007/0275416 A1 | 11/2007 | Gloeckner et al. |
| 2008/0053543 A1 | 3/2008 | Baier et al. |
| 2008/0053901 A1 | 3/2008 | Mierendorf et al. |
| 2008/0053917 A1 | 3/2008 | Larson et al. |
| 2008/0064093 A1 | 3/2008 | Porter et al. |
| 2008/0153712 A1 | 6/2008 | Crea |
| 2008/0171059 A1 | 7/2008 | Howland et al. |
| 2008/0206239 A1 | 8/2008 | Jones et al. |
| 2009/0082213 A1 | 3/2009 | Horowitz et al. |
| 2009/0280560 A1 | 11/2009 | Wittrup et al. |
| 2010/0009866 A1 | 1/2010 | Prinz et al. |
| 2010/0292103 A1 | 11/2010 | Ladner |
| 2011/0009280 A1 | 1/2011 | Hufton et al. |
| 2011/0082054 A1 | 4/2011 | Ladner |
| 2011/0136695 A1 | 6/2011 | Crea |
| 2011/0189183 A1 | 8/2011 | Williamson et al. |
| 2013/0046056 A1 | 2/2013 | Spector et al. |
| 2014/0031292 A1 | 1/2014 | Wittrup et al. |
| 2014/0031522 A1 | 1/2014 | Li et al. |
| 2014/0080766 A1 | 3/2014 | Pirie et al. |
| 2014/0296434 A1 | 10/2014 | Spector et al. |
| 2014/0364340 A1 | 12/2014 | Vasquez et al. |
| 2015/0080558 A1 | 3/2015 | Spector et al. |

FOREIGN PATENT DOCUMENTS

| | | |
|---|---|---|
| WO | WO-85/04330 A1 | 10/1985 |
| WO | WO-88/01649 A1 | 3/1988 |
| WO | WO-88/06630 A1 | 9/1988 |
| WO | WO-90/07380 A2 | 7/1990 |
| WO | WO-93/11161 A1 | 6/1993 |
| WO | WO-94/07922 A1 | 4/1994 |
| WO | WO 95/26400 A1 | 10/1995 |
| WO | WO-97/08320 A1 | 3/1997 |
| WO | WO-97/20923 A1 | 6/1997 |
| WO | WO-97/49809 A1 | 12/1997 |
| WO | WO-98/49198 A1 | 11/1998 |
| WO | WO-9852976 A1 | 11/1998 |
| WO | WO-99/06834 A2 | 2/1999 |
| WO | WO 99/28502 A1 | 6/1999 |
| WO | WO-99/36569 A1 | 7/1999 |
| WO | WO-99/50461 A1 | 10/1999 |
| WO | WO 99/53049 A1 | 10/1999 |
| WO | WO-99/55367 A1 | 11/1999 |
| WO | WO-00/18905 A1 | 4/2000 |
| WO | WO 00/54057 A1 | 9/2000 |
| WO | WO-01/79229 A2 | 10/2001 |
| WO | WO-01/79481 A2 | 10/2001 |
| WO | WO-2005/007121 A2 | 1/2005 |
| WO | WO-2005023993 A2 | 3/2005 |
| WO | WO-2006/138700 A2 | 12/2006 |
| WO | WO-2007/056441 A2 | 5/2007 |
| WO | WO-2008/019366 A2 | 2/2008 |
| WO | WO-2008/053275 A2 | 5/2008 |
| WO | WO-2008067547 A2 | 6/2008 |
| WO | WO-2009/036379 A2 | 3/2009 |
| WO | WO-2010005863 A1 | 1/2010 |

OTHER PUBLICATIONS

Portner-Taliana et al. Journal of immunological Methods, 238:161-172, 2000.*

Muhle-Goll et al. Biochemistry, 34:13554-13564, 1995.*

Wu et al., (J. Mol. Biol., vol. 294(1), pp. 151-162, 1999).*

Fusco, et al. In Vivo Construction of cDNA Libraries for Use in the Yeast Two-Hybrid System. Yeast. 1999; 15:715-720.

Kieke, et al. Selection of functional T cell receptor mutants from a yeast surface-display library. Proc. Natl. Acad. Sci. USA. 1999; 96:5651-5656.

Ma, et al. Plasmid construction by homologous recombination in yeast. Gene. 1987; 58:201-216.

Uetz, et al. A comprehensive analysis of protein-protein interactions in *Saccharomyces cerevisiae*. Nature. 2000; 403:623-627.

Zhu, et al: Analysis of a peptide hormone-receptor interaction in the yeast two-hybrid system. Proc. Natl. Acad. Sci. USA. 1997; 94:13063-13068.

Horwitz AH et al., "Secretion of Functional Antibody and Fab Fragments From Yeast Cells," *Proc. Natl. Acad. Sci. USA*, 85:8678-8682 (1998).

Cioe, L., Cloning and Nucleotide Sequence of a Mouse Erythrocyte beta-Spectrin cDNA, Blood, 70:915-920 (1987).

Interference No. 105809 Decision on Motions, dated Nov. 2, 2012.

Interference No. 105809 Dyax Resp to Order to Show Cause, dated Jan. 4, 2013.

Kokubu F. et al., Complete structure and organization of immunoglobulin heavy chain constant region genes in a phylogenetically primitive vertebrate, The EMBO Journal, 7(7):1979-1988 (1988).

McCormack, W.T., Comparison of latent and nominal rabbit Ig VHa1 allotype cDNA sequences. J. Immunol., 141(6):2063-2071 (1988).

Schwager, J. et al., Amino acid sequence of heavy chain from Xenopus levis IgM deduced from cDNA sequence: Implications for evolution of immunoglobulin domains, Proc. Natl. Acad. Sci. USA, 85:2245-2249 (1988).

U.S. Appl. No. 13/213,302, Protest Under 37 CFR § 1.291 on behalf of Dyax Corp, May 11, 2012, 491 pages.

U.S. Appl. No. 13/249,581, Protest Under 37 CFR § 1.291 on behalf of Dyax Corp, May 25, 2012, 566 pages.

U.S. Appl. No. 13/300,308, Protest Under 37 CFR § 1.291 on behalf of Dyax Corp, May 25, 2012, 742 pages.

U.S. Appl. No. 13/300,340, Protest Under 37 CFR § 1.291 on behalf of Dyax Corp, May 25, 2012, 734 pages.

U.S. Appl. No. 13/300,534, Protest Under 37 CFR § 1.291 on behalf of Dyax Corp, May 25, 2012, 486 pages.

Philibert et al., "A focused antibody library for selected scFvs expressed at high levels in the cytoplasm," BMC Biotechnology, 2007, 7:81.

Abbas, A.K. et al., Cellular and Molecular Immunology 4th Ed. W.B. Saunders Company, p. 133 (2000).

Adams, G.P. and Schier, R., "Generating Improved Single-Chain Fv Molecules For Tumor Targeting" Journal of Immunological Methods, 231:249-260 (1999).

Adams, G.P. and Weiner, L. M., "Monoclonal antibody therapy of cancer" Nature Biotechnology, 23(9) 1147-1157 (2005).

Adimab Clean Copy of Claims, Filed in Interference No. 105,809, Filed May 19, 2011.

(56) References Cited

OTHER PUBLICATIONS

Adimab Current List of Exhibits, Filed in Interference No. 105,809, Filed Jan. 20, 2012.
Adimab Current List of Exhibits, Filed in Interference No. 105,809, Filed Sep. 30, 2011.
Adimab Designation of Lead and Backup Counsel, Filed in Interference No. 105,809, Filed May 19, 2011.
Adimab Exhibit 2001, Filed in Interference No. 105,809, Filed Aug. 19, 2011—U.S. Pat. No. 7,700,302 Issued May 19, 1992.
Adimab Exhibit 2002, Filed in Interference No. 105,809, Filed Aug. 19, 2011—Boder and Wittrup—Boder et al "Yeast surface display for screening combinatorial polypeptide libraries" (1997).
Adimab Exhibit 2003, Filed in Interference No. 105,809, Filed Aug. 19, 2011—Boder and Wittrup "Yeast Surface Display for Directed Evolution of Protein Expression, Affinity, and Stability" (2000).
Adimab Exhibit 2004, Filed in Interference No. 105,809, Filed Aug. 19, 2011—Schreuder et al., "Immobilizing proteins on the surface of yeast cells" (1996).
Adimab Exhibit 2005, Filed in Interference No. 105,809, Filed Aug. 19, 2011—Liu et al. "Rapid Construction of Recombinant DNA by the Univector Plasmid-Fusion System" (2005).
Adimab Exhibit 2006, Filed in Interference No. 105,809, Filed Aug. 19, 2011—Walhout et al., "GATEWAY Recombinational Cloning: Application to the Cloning of Large Numbers of Open Reading Frames or ORFeomes" (2000).
Adimab Exhibit 2007, Filed in Interference No. 105,809, Filed Aug. 19, 2011—Smith, G. "Homologous Recombination Near and Far from DNA Breaks: Alternative Roles and Contrasting Views" (2001).
Adimab Exhibit 2008, Filed in Interference No. 105,809, Filed Aug. 19, 2011—Declaration of David M. Kranz, Ph.D.
Adimab Exhibit 2009, Filed in Interference No. 105,809, Filed Aug. 19, 2011—Sauer, B. "Inducible Gene Targeting in Mice Using the Crd / lox System" (1998).
Adimab Exhibit 2010, Filed in Interference No. 105,809, Filed Aug. 19, 2011—WO 03/02956 Published Apr. 10, 2003.
Adimab Exhibit 2011, Filed in Interference No. 105,809, Filed Aug. 19, 2011—EP 02766425 Amendment before Examination filed Jun. 16, 2004.
Adimab Exhibit 2012, Filed in Interference No. 105,809, Filed Aug. 19, 2011—EP Publication No. EP1438400 Published Jun. 17, 2009.
Adimab Exhibit 2013, Filed in Interference No. 105,809, Filed Aug. 19, 2011—USSN 10,26264: Non-Final Rejection Issued Dec. 13, 2007.
Adimab Exhibit 2014, Filed in Interference No. 105,809, Filed Aug. 19, 2011—Pogue and Goodnow—"Gene Dose-dependent Maturation and Receptor Editing of B Cells Expressing Immumoglobulin (Ig)G1 or IgM/IgG1 Tail Antigen Receptors" (2000).
Adimab Exhibit 2015, Filed in Interference No. 105,809, Filed Aug. 19, 2011—U.S. Appl. No. 10/262,646: Amendment in Reply to Action of Sep. 7, 2006.
Adimab Exhibit 2016, Filed in Interference No. 105,809, Filed Aug. 19, 2011—U.S. Appl. No. 10/262,646: Amendment in Reply to Action of Dec. 13, 2007.
Adimab Exhibit 2017, Filed in Interference No. 105,809, Filed Aug. 19, 2011—Swers et al., "Shuffled antibody libraries created by in vivo homologous recombination and yeast surface display" (2004).
Adimab Exhibit 2018, Filed in Interference No. 105,809, Filed Aug. 19, 2011—U.S. Appl. No. 12/625,337: Dyax's Third Preliminary Amendment and Suggestion of Interference under 37 C.F.R. § 41.202(a) filed Jan. 24, 2011.
Adimab Exhibit 2019, Filed in Interference No. 105,809, Filed Aug. 19, 2011—*Agilent Technologies, Inc.* v. *Affymetrix, Inc.* Decided Jun. 4, 2009.
Adimab Exhibit 2020, Filed in Interference No. 105,809, Filed Aug. 19, 2011—*Jones J. Robertson and Robert M. Currie* v. *Jos Timmermans and Jean C. Raymond* Decided May 5, 2010.
Adimab Exhibit 2021, Filed in Interference No. 105,809, Filed Aug. 19, 2011—U.S. Appl. No. 10/818,920: Ex parte Donald V. Smart—Appeal 2009-015036.
Adimab Exhibit 2022, Filed in Interference No. 105,809, Filed Aug. 19, 2011—Dyax Motions List filed Jun. 28, 2011.
Adimab Exhibit 2023, Filed in Interference No. 105,809, Filed Aug. 19, 2011—U.S. Appl. No. 10/262,646: Final Rejection Issued Oct. 3, 2008.
Adimab Exhibit 2024, Filed in Interference No. 105,809, Filed Aug. 19, 2011—U.S. Appl. No. 10/262,646: Amendment in Reply to Action of Oct. 3, 2008 filed Apr. 3, 2009.
Adimab Exhibit 2025, Filed in Interference No. 105,809, Filed Aug. 19, 2011—U.S. Appl. No. 12/625,337: Amendment and Response to Notice to File Missing Parts filed Aug. 17, 2010.
Adimab Exhibit 2026, Filed in Interference No. 105,809, Filed Aug. 19, 2011—U.S. Appl. No. 09/703,399, filed Oct. 31, 2000.
Adimab Exhibit 2027, Filed in Interference No. 105,809, Filed Aug. 19, 2011—USSN 2011/0009280 Published Jan. 13, 2011.
Adimab Exhibit 2028, Filed in Interference No. 105,809, Filed Aug. 19, 2011—Adimab's Reissue Application U.S. Appl. No. 13/213,302, filed Aug. 19, 2011.
Adimab Exhibit 2029, Filed in Interference No. 105,809, Filed Aug. 19, 2011—U.S. Pat. No. 7,700,302: Amendment in Accordance with 37 C.F.R. §1.73(b) filed Aug. 19, 2011.
Adimab Exhibit 2030, Filed in Interference No. 105,809, Filed Aug. 19, 2011—Dyax's U.S. Appl. No. 10/262,646, filed Sep. 30, 2002.
Adimab Exhibit 2031, Filed in Interference No. 105,809, Filed Aug. 19, 2011—Dyax's U.S. Appl. No. 60/326,320, filed Oct. 1, 2001.
Adimab Exhibit 2032, Filed in Interference No. 105,809, Filed Aug. 19, 2011—Adimab's U.S. Appl. No. 11/593,957, filed Nov. 6, 2006.
Adimab Exhibit 2033, Filed in Interference No. 105,809, Filed Aug. 19, 2011—Adimab's U.S. Appl. No. 10/360,828, filed Feb. 7, 2003.
Adimab Exhibit 2034, Filed in Interference No. 105,809, Filed Aug. 19, 2011—Adimab's U.S. Appl. No. 10/133,978, filed Apr. 25, 2002.
Adimab Exhibit 2035, Filed in Interference No. 105,809, Filed Aug. 19, 2011—Adimab's U.S. Appl. No. 10/072,301, filed Feb. 8, 2002.
Adimab Exhibit 2036, Filed in Interference No. 105,809, Filed Aug. 19, 2011—Adimab's U.S. Appl. No. 10/071,866, filed Feb. 8, 2002.
Adimab Exhibit 2037, Filed in Interference No. 105,809, Filed Aug. 19, 2011—U.S. Appl. No. 12/625,337, filed Nov. 24, 2009.
Adimab Exhibit 2038, Filed in Interference No. 105,809, Filed Aug. 19, 2011—Assignment for U.S. Pat. No. 7,700,302 filed Nov. 6, 2006.
Adimab Exhibit 2039, Filed in Interference No. 105,809, Filed Aug. 19, 2011—Filing Receipt for U.S. Appl. No. 11/593,957 dated Dec. 4, 2006.
Adimab Exhibit 2040, Filed in Interference No. 105,809, Filed Aug. 19, 2011—Hua et al., "Minimum Length of Sequence Homology Required for in Vivo Cloning by Homologous Recombination in Yeast" (1997).
Adimab Exhibit 2041, Filed in Interference No. 105,809, Filed Aug. 19, 2011—U.S. Appl. No. 10/262,646: Notice of Abandonment dated Dec. 10, 2009.
Adimab Exhibit 2042, Filed in Interference No. 105,809, Filed Aug. 19, 2011—U.S. Appl. No. 10/133,978: Office Action Restricing Claims dated Oct. 5, 2004.
Adimab Exhibit 2043, Filed in Interference No. 105,809, Filed Aug. 19, 2011—U.S. Appl. No. 09/703,399 Complete File History.
Adimab Exhibit 2044, Filed in Interference No. 105,809, Filed Aug. 19, 2011—U.S. Appl. No. 13/213,302 Second Amendment to Introduce Missing Drawing Sheets filed on Aug. 19, 2011.
Adimab Exhibit 2045, Filed in Interference No. 105,809, Filed Sep. 30, 2011—U.S. Pat. No. 7,138,496 Issued Nov. 21, 2006.
Adimab Exhibit 2046, Filed in Interference No. 105,809, Filed Sep. 30, 2011—U.S. Pat. No. 7,005,503 Issued Feb. 28, 2006.
Adimab Exhibit 2047, Filed in Interference No. 105,809, Filed Sep. 30, 2011—U.S. Appl. No. 13/249,581: Complete File History of the CON of Reissue.
Adimab Exhibit 2048, Filed in Interference No. 105,809, Filed Sep. 30, 2011—U.S. Appl. No. 13/213,302: Fourth Preliminary Amendment filed Aug. 19, 2011.
Adimab Exhibit 2049, Filed in Interference No. 105,809, Filed Sep. 30, 2011—U.S. Pat. No. 6,610,472 Issued Aug. 26, 2003.

(56) References Cited

OTHER PUBLICATIONS

Adimab Exhibit 2050, Filed in Interference No. 105,809, Filed Sep. 30, 2011—U.S. Appl. No. 13/213,302: Third Preliminary Amendment filed Aug. 19, 2011.
Adimab Exhibit 2051, Filed in Interference No. 105,809, Filed Nov. 21, 2011—Horwitz et al., "Secretion of functional antibody and Fab fragment from yeast cells" (1988).
Adimab Exhibit 2052, Filed in Interference No. 105,809, Filed Nov. 21, 2011—US Publication No. 2003/0232395 Published Dec. 18, 2003.
Adimab Exhibit 2053, Filed in Interference No. 105,809, Filed Nov. 21, 2011—Website of Nathalie Scholler, MD., Ph.D.
Adimab Exhibit 2054, Filed in Interference No. 105,809, Filed Nov. 21, 2011—Raymond et al., "General Method for Plasmid Construction Using Homologous Recombination" (1999).
Adimab Exhibit 2055, Filed in Interference No. 105,809, Filed Nov. 21, 2011—U.S. Pat. No. 6,300,065 Issued Oct. 9, 2001.
Adimab Exhibit 2056, Filed in Interference No. 105,809, Filed Nov. 21, 2011—U.S. Pat. No. 6,027,910 Issued Feb. 22, 2000.
Adimab Exhibit 2057, Filed in Interference No. 105,809, Filed Nov. 21, 2011—U.S. Pat. No. 6,696,251 Issued Feb. 24, 2004.
Adimab Exhibit 2058, Filed in Interference No. 105,809, Filed Nov. 21, 2011—International Publication No. WO 94/18330 Published Aug. 18, 1994.
Adimab Exhibit 2059, Filed in Interference No. 105,809, Filed Nov. 21, 2011—U.S. Pat. No. 6,114,147 Issued Sep. 5, 2000.
Adimab Exhibit 2060, Filed in Interference No. 105,809, Filed Nov. 21, 2011—Schreuder et al., "Targeting of a Heterologous Protein to the Cell Wall of Saccharamyces cerevisiae" (1993).
Adimab Exhibit 2061, Filed in Interference No. 105,809, Filed Nov. 21, 2011—Imai and Yamamoto "The fission yeast mating pheromone P-factor: its molecular structure, gene structure, and ability to induce gene expression and $G_1$ arrest in the mating partner" (1993).
Adimab Exhibit 2062, Filed in Interference No. 105,809, Filed Nov. 21, 2011—Cappellaro et al "Mating type-specific cell—cell recognition of Saccharomyces cerevisiae: cell wall attachment and active sites of a- and α-agglutinin[1]" (1994).
Adimab Exhibit 2063, Filed in Interference No. 105,809, Filed Nov. 21, 2011—Van der vaart et al., "Comparison of Cell Wall Proteins of Saccharomyces cerevisiae as Anchors for Cell Surface Expression of Heterologous Proteins" (1997).
Adimab Exhibit 2064, Filed in Interference No. 105,809, Filed Nov. 21, 2011—Murai et al., "Construction of a Starch-Utilizing Yeast by Cell Surface Engineering" (1997).
Adimab Exhibit 2065, Filed in Interference No. 105,809, Filed Nov. 21, 2011—Ueda and Tanaka "Cell Surface Engineering of Yeast: Construction of Arming Yeast with Biocatalyst" (2000).
Adimab Exhibit 2066, Filed in Interference No. 105,809, Filed Nov. 21, 2011—Shibasaki et al., "Construction of an engineered yeast with glucose-inducible emission of green fluorescence from the cell surface" (2000).
Adimab Exhibit 2067, Filed in Interference No. 105,809, Filed Nov. 21, 2011—Boder and Wittrup "Yeast surface display system for antibody engineeirng" (1996).
Adimab Exhibit 2068, Filed in Interference No. 105,809, Filed Nov. 21, 2011—Deposition of David M. Kranz, Ph.D. dated Oct. 14, 2011.
Adimab Exhibit 2069, Filed in Interference No. 105,809, Filed Nov. 21, 2011—Depostion of Nathalie Scholler, M.D., Ph. D. dated Oct. 24, 2011.
Adimab Exhibit 2070, Filed in Interference No. 105,809, Filed Nov. 21, 2011—U.S. Pat. No. 6,699,658 Issued Mar. 2, 2004.
Adimab Exhibit 2071, Filed in Interference No. 105,809, Filed Nov. 21, 2011—U.S. Pat. No. 7,208,293 Issued Apr. 24, 2007.
Adimab Exhibit 2072, Filed in Interference No. 105,809, Filed Nov. 21, 2011—International Publication No. WO 94/01567 Published Jan. 20, 1994.
Adimab Exhibit 2073, Filed in Interference No. 105,809, Filed Nov. 21, 2011—U.S. Pat. No. 6,423,538 Issued Jul. 23, 2002.
Adimab Exhibit 2074, Filed in Interference No. 105,809, Filed Nov. 21, 2011—Hendershot and Sitia "Immunoglobulin Assembly and Secretion" (2004).
Adimab Exhibit 2075, Filed in Interference No. 105,809, Filed Nov. 21, 2011—Hoogenboom and Chames "Natural and designer binding sites made by phage display technology" (2000).
Adimab Exhibit 2076, Filed in Interference No. 105,809, Filed Nov. 21, 2011—U.S. Appl. No. 11/593,957 Notice of Allowance dated Nov. 19, 2009.
Adimab Exhibit 2077, Filed in Interference No. 105,809, Filed Nov. 21, 2011—Declaration of Eric T. Boder, Ph.D. filed Nov. 21, 2011.
Adimab Exhibit 2078, Filed in Interference No. 105,809, Filed Nov. 21, 2011—Second Declaration of David M. Kranz, Ph.D. filed Nov. 21, 2011.
Adimab Exhibit 2079, Filed in Interference No. 105,809, Filed Nov. 21, 2011—U.S. Appl. No. 13/300,340: Reissue Application filed Nov. 18, 2011.
Adimab Exhibit 2080 [corrected], Filed in Interference 105,809, Filed Nov. 21, 2011—U.S. Appl. No. 13/300,308: [corrected] Reissue Application filed Nov. 18, 2011.
Adimab Exhibit 2081, Filed in Interference No. 105,809, Filed Nov. 21, 2011—Declaration of James Sheridan, Ph.D. filed Nov. 21, 2011.
Adimab Exhibit 2082, Filed in Interference No. 105,809, Filed Nov. 21, 2011—Curriculum Vitae for Eric T. Boder, Ph.D.
Adimab Exhibit 2083, Filed in Interference No. 105,809, Filed Nov. 21, 2011—Curriculum Vitae for David M. Kranz, Ph.D.
Adimab Exhibit 2084, Filed in Interference No. 105,809, Filed Nov. 21, 2011—U.S. Pat. No. 5,223,409 Issued Jun. 29, 1993.
Adimab Exhibit 2085, Filed in Interference No. 105,809, Filed Nov. 21, 2011—Patel et al., "Parallel selection of antibody libraries on phage and yeast surfaces via a cross-species display" (2011).
Adimab Exhibit 2086, Filed in Interference No. 105,809, Filed Nov. 21, 2011—Struhl et al., "High-frequency transformation of yeast: Autonomous replication of hybrid DNA molecules" (1979).
Adimab Exhibit 2087, Filed in Interference No. 105,809, Filed Jan. 20, 2012—Ueda and Tanaka "Genetic immobilization of proteins on the yeast cell surface" (2000).
Adimab Exhibit 2088, Filed in Interference No. 105,809, Filed Jan. 20, 2012—Deposition of Eric T. Boder, Ph.D. dated Dec. 20, 2011.
Adimab Exhibit 2089, Filed in Interference No. 105,809, Filed Jan. 20, 2012—Second Deposition of David M. Kranz, Ph.D. dated Jan. 3, 2012.
Adimab Exhibit 2090, Filed in Interference No. 105,809, Filed Jan. 20, 2012—Schöndorf et al., "Characterization of the Complete Genome of the Tupaia (Tree Shrew) Adenovirus" (2002/2003).
Adimab Exhibit 2091, Filed in Interference No. 105,809, Filed Jan. 20, 2012—Availability emails for Dr. Sheridan, Dr. Boder, Dr. Kranz, Dr. Zhu and Dr. Scholler, between Wolf, Greenfield & Sacks, P.C. and Choate Hall & Stewart LLP.
Adimab Exhibit 2092, Filed in Interference No. 105,809, Filed Jan. 20, 2012—Second Deposition of Nathalie Scholler, M.D., Ph.D. dated Jan. 12, 2012.
Adimab Exhibit 2093, Filed in Interference No. 105,809, Filed Jan. 20, 2012—U.S. Pat. No. 7,700,302: Application for Reissue of Utility Patent filed on Sep. 30, 2011.
Adimab Exhibit 2094, Filed in Interference No. 105,809, Filed Jan. 20, 2012—Davison et al., "Genetic content and evolution of adenoviruses" (2003).
Adimab Exhibit 2095, Filed in Interference No. 105,809, Filed Jan. 20, 2012—U.S. Appl. No. 13/213,302 Filing Receipt for Reissue of U.S. Pat. No. 7,700,302 dated Oct. 11, 2011.
Adimab Exhibit 2096, Filed in Interference No. 105,809, Filed Jan. 20, 2012—U.S. Appl. No. 13/300,308 Filing Receipt for Reissue of U.S. Pat. No. 7,138,496 dated Dec. 26, 2011.
Adimab Exhibit 2097, Filed in Interference No. 105,809, Filed Jan. 20, 2012—U.S. Appl. No. 13/213,302: Petition to Accept an Unintentionally Delayed Priority Claim under 37 C.F.R. § 1.78(a)(3) filed Jan. 18, 2012.
Adimab Exhibit 2098, Filed in Interference No. 105,809, Filed Jan. 20, 2012—U.S. Appl. No. 13/300,340: Petition to Accept an Unintentionally Delayed Priority Claim under 37 C.F.R. § 1.78(a)(3) filed Jan. 18, 2012.

(56) References Cited

OTHER PUBLICATIONS

Adimab Exhibit 2099, Filed in Interference No. 105,809, Filed Jan. 20, 2012—U.S. Appl. No. 13/300,308: Petition to Accept an Unintentionally Delayed Priority Claim under 37 C.F.R. § 1.78(a)(3) filed Jan. 19, 2012.
Adimab Exhibit 2100, Filed in Interference No. 105,809, Filed Feb. 3, 2012—Adimab's Objections to ¶¶ 26, 44-47 & 48-51 of Dyax Exhibit 1112 filed Jan. 27, 2012.
Adimab List of Exhibits, Filed in Interference No. 105,809, Filed Feb. 3, 2012.
Adimab List of Proposed Motions, Filed in Interference No. 105,809, Filed Jun. 28, 2011.
Adimab Misc. Motion 7—Approved, Filed in Interference No. 105,809, Filed Nov. 23, 2011.
Adimab Miscellaneous Motion 7, Filed in Interference No. 105,809, Filed Nov. 23, 2011.
Adimab Miscellaneous Motion 8, Filed in Interference No. 105,809, Filed Feb. 3, 2012.
Adimab Miscellaneous Motion 9, Filed in Interference No. 105,809, Filed Feb. 3, 2012.
Adimab Notice Designating Additional Backup Counsel, Filed in Interference No. 105,809, Filed Dec. 12, 2011.
Adimab Notice of Exhibit List Filed, Filed in Interference No. 105,809, Filed Jan. 20, 2012.
Adimab Notice of Exhibit List Filed, Filed in Interference No. 105,809, Filed Feb. 3, 2012.
Adimab Notice of Exhibits filed, Filed in Interference No. 105,809, Filed Aug. 19, 2011.
Adimab Notice of Exhibits Filed, Filed in Interference No. 105,809, Filed Sep. 30, 2011.
Adimab Notice of Real Party in Interest, Filed in Interference No. 105,809, Filed May 19, 2011.
Adimab Notice of Related Proceedings, Filed in Interference No. 105,809, Filed May 19, 2011.
Adimab Notice of Service of Priority Statement, Filed in Interference No. 105,809, Filed Aug. 26, 2011.
Adimab Opposition 1, Filed in Interference No. 105,809, Filed Nov. 21, 2011.
Adimab Opposition 2, Filed in Interference No. 105,809, Filed Nov. 21, 2011.
Adimab Opposition 3, Filed in Interference No. 105,809, Filed Nov. 21, 2011.
Adimab Opposition 4, Filed in Interference No. 105,809, Filed Nov. 21, 2011.
Adimab Priority Statement, Filed in Interference No. 105,809, Filed Aug. 19, 2011.
Adimab Reply 1, Filed in Interference No. 105,809, Filed Jan. 20, 2012.
Adimab Reply 2, Filed in Interference No. 105,809, Filed Jan. 20, 2012.
Adimab Reply 3, Filed in Interference No. 105,809, Filed Jan. 20, 2012.
Adimab Reply 4, Filed in Interference No. 105,809, Filed Jan. 20, 2012.
Adimab Reply 5, Filed in Interference No. 105,809, Filed Jan. 20, 2012.
Adimab Reply 6, Filed in Interference No. 105,809, Filed Jan. 20, 2012.
Adimab Request for File Copies, Filed in Interference No. 105,809, Filed May 19, 2011.
Adimab Request for Oral Argument, Filed in Interference No. 105,809, Filed Feb. 3, 2012.
Adimab Responsive Motion 6, Filed in Interference No. 105,809, Filed Sep. 30, 2011.
Adimab Substantive Motion 1, Filed in Interference No. 105,809, Filed Aug. 19, 2011.
Adimab Substantive Motion 2, Filed in Interference No. 105,809, Filed Aug. 19, 2011.
Adimab Substantive Motion 3, Filed in Interference No. 105,809, Filed Aug. 19, 2011.
Adimab Substantive Motion 4—request to substitute count, Filed in Interference No. 105,809, Filed Aug. 19, 2011.
Adimab Substantive Motion 5, Filed in Interference No. 105,809, Filed Aug. 19, 2011.
Adimab's Notice of Filing Preliminary Amendment, Filed in Interference No. 105,809, Filed Sep. 8, 2011.
Akamatsu, Y. et al., "Construction of a human Ig combinatorial library from genomic V segments and synthetic CDR3 fragments" J. Immunol., 51(9):4651-4659 (1993).
Allen, J.B. et al., "Finding prospective partners in the library: the two-hybrid system and phage display find a match" TIBS, 20:(12):511-516 (1995).
Alt, F.W. and Baltimore, D., "Joining of Immunoglobulin Heavy Chain Gene Segments: Implications from a Chromosome with Evidence of Three D-JH Fusions" PNAS, 79:4118-4122 (1982).
Alves, J. et al., "Accuracy of the EcoRV restriction endonuclease: binding and cleavage studies with oligodeoxynucleotide substrates containing degenerate recognition sequences" Biochemistry, 34(35): 11191-11197 (1995).
Arden, B., "Conserved motifs in T-cell receptor CDR1 and CDR2: implications for ligand and CDS co-receptor binding" Current Opinion in Immunology, Current Biology LTD., 10(1):74-81 (1998).
Aronheim, Ami et al., "Isolation of an AP-1 Repressor by a Novel Method For Detecting Protein-Protein Interactions" Molecular and Cellular Biology, 17(6):3094-3102 (1997).
Aujame, L. et al., "High affinity human antibodies by phage display" Human Antibodies, 8(4):155-168 (1997).
Ayala, M. et al., "Variable region sequence modulates periplasmic export of a single-chain Fv antibody fragment in *Escherichia coli*" BioTechniques, 18(5):832-838, 840-2 (1995).
Balint, R.F. and Larrick, J.W., "Antibody engineering by parsimonious mutagenesis" Gene, 137:109-118 (1993).
Barbas, C.F. 3rd et al., "Human autoantibody recognition of DNA" Proc. Natl. Acad. Sci., 92:2529-2533 (1995).
Barbas, C.F. 3rd et al., "Semisynthetic combinatorial antibody libraries: a chemical solution to the diversity problem" Proceedings of the National Academy of Sciences of USA, 89:4457-4461 (1992).
Barbas, C.F. 3rd, et al., "Assembly of combinatorial antibody libraries on phage surfaces: The gene III site" Proc. Natl. Acad. Sci., 88:7978-7982 (1991).
Basu, M. et al., "Synthesis of compositionally unique DNA by terminal deoxynucleotidyl transferase" Biochem. Biophys. Res. Comm., 111(3):1105-1112 (1983).
Bhatia, S.K. et al., "Rolling adhesion kinematics of yeast engineered to express selectins" Biotech. Prog., 19:1033-1037 (2003).
Binz, H.K. et al., "Engineering novel binding proteins from nonimmunoglobulin domains" Nat. Biotechnol., 23(10):1257-1268 (2005).
Bird, R.E. et al., "Single-chain antigen-binding proteins" Science, 242(4877):423-426 (1988).
Blakesley, et al., "Duplex Regions in "Single-stranded" øX174 DNA Are Cleaved by a Restriction Endonuclease from Haemophilus aegyptius*" The Journal of Bilogical Chemistry, 252:7300-7306 (1977).
Boder, E.T. and Jiang, W., "Engineering Antibodies for Cancer Therapy" Annu. Rev. Chem. Biomol. Eng. 2:53-75 (2011).
Boder, E.T. and Wittrup, K.D., "Optimal screening of surface-displayed polypeptide libraries" Biotechnol Prog., 14(1):55-62 (1998).
Boder, E.T. and Wittrup, K.D., "Yeast surface display for screening combinatorial polypeptide libraries" Nat Biotechnol., 15(6):553-7 (1997).
Boder, E.T. et al., "Directed evolution of antibody fragments with monovalent femtomolar antigen-binding affinity" Proc Natl Acad Sci USA, 97(20):10701-5 (2000).
Borth, N. et al., "Efficient selection of high-producing subclones during gene amplification of recombinant Chinese hamster ovary cells by flow cytometry and cell sorting" Biotechnol. and Bioengin., 71(4):266-273 (2000-2001).

(56) References Cited

OTHER PUBLICATIONS

Brachmann, Rainer K. and Boeke, J.D., "Tag games in yeast: the two-hybrid system and beyond" Curr. Opin. Biotechnol., 8(5):561-568 (1997).
Bradbury, A., "Display Technologies Expand Their Horizons" TIBTECH 17:137-138 (1999).
Bradbury, A., "Molecular Library Technologies at the Millenium", TIBTECH 18:132-133 (2000).
Bradbury, A., "Recent advances in phage display: the report of the Phage Club first meeting" Immunotechnology, 3(3):227-231 (1997).
Bray, J.K. et al., "Optimized Torsion-Angle Normal Modes Reproduce Conformational Changes More Accurately Than Cartesian Modes" Biophysical Journal 101 2966-2969 (2011).
Breitling, F. et al., "A surface expression vector for antibody screening" Gene, 104(2):147-153 (1991).
Brezinschek, H.P. et al., "Analysis of the human VH gene repertoire. Differential effects of selection and somatic hypermutation on human peripheral CD5(+)/IgM+ and CD5(−)/IgM+ B cells" The American Society for Clinical Investigation, Inc., 99(10):2488-2501 (1997).
Broder, Y.C. et al., "The ras recruitment system, a novel approach to the study of protein-protein interactions" Current Biology 8(20):1121-1124 (1998).
Burton, D.R. et al., "A large array of human monoclonal antibodies to type 1 human immunodeficiency virus from combinatorial libraries of asymptomatic seropostive individuals" Proc. Natl. Acad. Sci., 88(22):10134-10137 (1991).
Canaán-Haden, L., "Purification and application of a single-chain Fv antibody fragment specific to hepatitis B virus surface antigen" BioTechniques, 19(4) 606-608, 610, 612 passim(1995).
Castelli, L.A. et al., "High-level secretion of correctly processed beta-lactamase from Saccharomyces ceravisiae using a high-copy-number secretion vector" Biomolecular Research Institute, 142(1):113-117 (1994).
Caton, A.J. and Koprowski, H., "Influenza virus hemagglutinin-specific antibodies isolated from a combinatorial expression library are closely related to the immune response of the donor" Proc. Natl. Acad. Science, USA, 87(16):6450-6454 (1990).
Cattaneo, A. and Biocca, S., "The selection of intracellular antibodies" TIBTECH, 17:115-120 (1999).
Cha, J.H. et al., "Cell surface monkey CD9 antigen is a coreceptor that increases diphtheria toxin sensitivity and diphtheria toxin receptor affinity" Journal of Biological Chemistry, 275(10):6901-6907 (2000).
Chang, C.N. et al., "Expression of antibody Fab domains on bacteriophage surfaces. Potential use for antibody selection" J. Immunol, 147(10):3610-3614. (1991).
Chang, H.C. et al., "A general method for facilitating heterodimeric pairing between two proteins: Application to expression of alpha and beta T-cell receptor extracellular segments" Proc Natl. Acad. Sci., USA, 91:11408-11412 (1994).
Charlton, H.R. et al., "Characterisation of a generic monoclonal antibody harvesting system for adsorption of DNA by depth filters and various membranes" Bioseparation 8: 281-291 (1999).
Chaudhary, V.K. et al., "A rapid method of cloning functional variable-region antibody genes in Escherichia coli as single-chain immunotoxins" Proc. Natl. Acad. Sci., 87(3):1066-1070 (1990).
Chen, C.M. et al., "Direct interaction of hepatitis C virus core protein with the cellular lymphotoxin-beta receptor modulates the signal pathway of the lymphotoxin-beta receptor" Journal of Virology, 71(12):9414-9426 (1997).
Chen, W. et al., "Characterization of germline antibody libraries from human umbilical cord blood and selection of monoclonal antibodies to viral envelope glycoproteins: Implications for mechanisms of immune evasion and design of vaccine immunogens" Biochem. Biophys. Res. Commun. 1-6 (2012).
Chiswell, David and McCaffery, John, "Phage antibodies: will new 'coliclonal' antibodies replace monoclonal antibodies?" TIBTECH, 10(3):80-84 (1992).

Chothia, C. and Lesk, A.M., "Canonical structures for the hypervariable regions of immunoglobulins" J. Mol. Biol., 196(4):901-917 (1987).
Chothia, C. et al., "Conformations of immunoglobulin hypervariable regions" Nature, 342(6252):877-883 (1989).
Chothia, C. et al., "Structural repertoire of the human VH segments" J. Mol. Biol., 227(3):799-817 (1992).
Clackson, T. and Wells, J.A., "In vitro selection from protein and peptide libraries" Elsevier Science Ltd., 12(5):173-184 (1994).
Clackson, T. et al., "Making antibody fragments using phage display librarires" Nature, 352(6336):624-628 (1991).
Clean copy of involved claims, Filed in Interference No. 105,809, Filed May 20, 2011.
Cochet O. et al., "Intracellular expression of an antibody fragment-neutralizing p21 ras promotes tumor regression", Cancer Res. ,58(6):1170-1176 (1998).
Collins, A.M. et al., "Partitioning of rearranged Ig genes by mutation analysis demonstrates D-D fusion and V gene replacement in the expressed human repertoire" J. Immunol., 172(1):340-348 (2004).
Collins, A.M. et al., "The reported germline repertoire of human immunoglobulin kappa chain genes is relatively complete and accurate" Immunogenetics, 60(11):669-676 (2008).
Corbett, S.J. et al., "Sequence of the human immunoglobulin diversity (D) segment locus: a systematic analysis provides no evidence for the use of DIR segments, nverted D egments, "minor" D segments or D-D recombination" J. Mol. Bioi., 270:587-597 (1997).
Corrected Adimab Opposition 4, Filed in Interference No. 105,809, Filed Nov. 23, 2011.
Courtney, B.C. et al., "A phage display vector with improved stability, applicability and ease of manipulation", Gene, 165(1):139-140 (1995).
Couto, J.R. et al., "Designing human consensus antibodies with minimal positional templates", Cancer Res., (23 Suppl):5973s-5977s (1995).
Crameri, R. and Blaser, K., "Cloning Aspergillus fumigatus allergens by the pJuFo filamentous phage display system" Int Arch Allergy Immunol,110(1):41-45 (1996).
Crameri, R. and Suter, M. , "Display of biologically active proteins on the surface of filamentous phages: a cDNA cloning system for selection of functional gene products linked to the genetic information responsible for their production" Gene, 137(1):69-75 (1993).
Current List of Exhibits, Filed in Interference No. 105,809, Filed Nov. 21, 2011.
Cwirla, S.E., et al., "Peptides on phage: a vast library of peptides for identifying ligands" Proc. Natl. Acad. Sci. USA, 87(16):6378-6382 (1990).
Davies, J. and Riechmann, L., "Affinity improvement of single antibody VH domains: residues in all three hypervariable regions affect antigen binding" Immunotechnology 2(3):169-179 (1996).
de Haard et al., "A Large Non-immunized Human Fab Fragment Phage Library That Permits Rapid Isolation and Kinetic Analysis of High Affinity Antibodies" Journal of Biological Chemistry, 274(26):18218-18230 (1999).
De Jaeger, G. et al., "Analysis of the interaction between single-chain variable fragments and their antigen in a reducing intracellular environment using the two-hybrid system" FEBS Lett., 467(2-3):316-320 (2000).
de Kruif, J. et al., "Selection and application of human single chain Fv antibody fragments from a semi-synthetic phage antibody display library with designed CDR3 regions" J. Mol. Biol. 248(1):97-105 (1995).
De Simone, A. et al., "Experimental free energy surfaces reveal the mechanisms of maintenance of protein solubility" PNAS, 108:52 21057-21062 (2011).
Declaration BD.R. 203, Filed in Interference No. 105,809, Filed May 6, 2011.
Delves, P.J. "Antibody production: essential techniques" John Wiley & Sons, New York, pp. 90-113 (1997).
Designation of Lead and Backup Counsel, Filed in Interference No. 105,809, Filed May 20, 2011.

(56) References Cited

OTHER PUBLICATIONS

Dyax Corrected Substantive Motion 1, Filed in Interference No. 105,809, Filed Sep. 2, 2011.
Dyax Exhibit 1000, Filed in Interference No. 105,809, Filed Aug. 19, 2011—Dyax Exhibit List dated Aug. 19, 2011.
Dyax Exhibit 1001, Filed in Interference No. 105,809, Filed Aug. 19, 2011—U.S. Pat. No. 7,700,302 Issued Apr. 20, 2010.
Dyax Exhibit 1002, Filed in Interference No. 105,809, Filed Aug. 19, 2011—U.S. Appl. No. 12/625,337, filed Nov. 24, 2009.
Dyax Exhibit 1003, Filed in Interference No. 105,809, Filed Aug. 19, 2011—Curriculum Vitae for Nathalie Scholler (née Buonavista), M.D., Ph.D.
Dyax Exhibit 1004, Filed in Interference No. 105,809, Filed Aug. 19, 2011—Boder and Witrup "Yeast surface display for screening combinatorial polypetide libraries" (1997).
Dyax Exhibit 1005, Filed in Interference No. 105,809, Filed Aug. 19, 2011—Kieke et al., "Isolation of anti-T cell receptor scFv mutants by yeast surface display" (1997).
Dyax Exhibit 1006, Filed in Interference No. 105,809, Filed Aug. 19, 2011—Cho et al., "A yeast surface display system for the discovery of ligands that trigger cell activation" (1998).
Dyax Exhibit 1007, Filed in Interference No. 105,809, Filed Aug. 19, 2011—Boder and Wittrup "Optimal Screening of Surface-Displayed Polypeptide Libraries" (1998).
Dyax Exhibit 1008, Filed in Interference No. 105,809, Filed Aug. 19, 2011—Kieke et al., "Selection of functional T cell receptor mutants from a yeast surface-display library" (1999).
Dyax Exhibit 1009, Filed in Interference No. 105,809, Filed Aug. 19, 2011—VanAntwerp and Wittrup "Fine Affinity Discrimination by Yeast Surface Display and Flow Cytometry" (2000).
Dyax Exhibit 1010, Filed in Interference No. 105,809, Filed Aug. 19, 2011—Holler et al., "In vitro evolution of a T cell recepto with high affinity for peptide / MHC" (2000).
Dyax Exhibit 1011, Filed in Interference No. 105,809, Filed Aug. 19, 2011—Shusta et al., "Directed evolution of a stable scaffold for T-cell receptor engineering" (2000).
Dyax Exhibit 1012, Filed in Interference No. 105,809, Filed Aug. 19, 2011—Boder et al., "Directed evolution of antibody fragments with monovalent femtomolar antigen-binding affinity" (2000).
Dyax Exhibit 1013, Filed in Interference No. 105,809, Filed Aug. 19, 2011—Yeung and Wittrup "Quantitative Screening of Yeast Surface-Displayed Polypeptide Libraries by Magnetic Bead Capture" (2002).
Dyax Exhibit 1014, Filed in Interference No. 105,809, Filed Aug. 19, 2011—Orr et al., "Rapid Method for Measuring ScFv Thermal Stability by Yeast Surface Display" (2003).
Dyax Exhibit 1015, Filed in Interference No. 105,809, Filed Aug. 19, 2011—Griffin et al., "Blockade of T Cell Activation Using a Surface-Linked Single-Chain Antibody to CTLA-4 (CD152)" (2000).
Dyax Exhibit 1016, Filed in Interference No. 105,809, Filed Aug. 19, 2011—Kieke et al., "High Affinity T Cell Receptors from Yeast Display Libraries Block T Cell Activation by Superantigens" (2001).
Dyax Exhibit 1017, Filed in Interference No. 105,809, Filed Aug. 19, 2011—Brophy et al., "A yeast display system for engineering functional peptide-MHC complexes" (2003).
Dyax Exhibit 1018, Filed in Interference No. 105,809, Filed Aug. 19, 2011—Starwalt et al., "Directed evolution of a single-chain class II MHC product by yeast display" (2003).
Dyax Exhibit 1019, Filed in Interference No. 105,809, Filed Aug. 19, 2011—van den Beucken et al., "Affnity maturation of Fab antibody fragments by fluorescent-activated cell sorting of yeast-displayed libraries" (2003).
Dyax Exhibit 1020, Filed in Interference No. 105,809, Filed Aug. 19, 2011—Brochure of the 13th Annual Phage and Yeast Display of Antibodies and Protein Conference.
Dyax Exhibit 1021, Filed in Interference No. 105,809, Filed Aug. 19, 2011—U.S. Pat. No. 6,610,472 Issued Aug. 26, 2003.
Dyax Exhibit 1022, Filed in Interference No. 105,809, Filed Aug. 19, 2011—Walhout et al., "Gateway Recombinational Cloning: Application to the Cloning of Large Numbers of Open Reading Frames or ORFeomes" (2000).
Dyax Exhibit 1023, Filed in Interference No. 105,809, Filed Aug. 19, 2011—Swers et al., "Shuffled antibody libraries created in vivo homologous recombination and yeast surface display" (2004).
Dyax Exhibit 1024, Filed in Interference No. 105,809, Filed Aug. 19, 2011—Swers et al., "Integrated Mimicry of B Cell Antibody Mutagenesis Using Yeast Homologous Recombination" (2011).
Dyax Exhibit 1025, Filed in Interference No. 105,809, Filed Aug. 19, 2011—Abbas et al., "Cellular and Molecular Immunology", 4th ed., p. 43, Figure 3-1,. W.B. Saunders Co. (2000).
Dyax Exhibit 1026, Filed in Interference No. 105,809, Filed Aug. 19, 2011—Lewin, B. "Genes V", p. 99, Oxford University Press (1994).
Dyax Exhibit 1027, Filed in Interference No. 105,809, Filed Aug. 19, 2011—Dranginis et al., "A Biochemical Guide to Yeast Adhesins: Glycoproteins for Social and Antisocial Occasions" (2007).
Dyax Exhibit 1027A, Filed in Interference No. 105,809, Filed Aug. 19, 2011—Dranginis et al., "A Biochemical Guide to Yeast Adhesins: Glycoproteins for Social and Antisocial Occasions" (2007).
Dyax Exhibit 1028, Filed in Interference No. 105,809, Filed Aug. 19, 2011—Sharifmoghadam, et al., "The fission yeast Map4 protein is a novel adhesin required for mating" (2006).
Dyax Exhibit 1029, Filed in Interference No. 105,809, Filed Aug. 19, 2011—International Publication No. WO 02/055718 Published Jul. 18, 2002.
Dyax Exhibit 1030, Filed in Interference No. 105,809, Filed Aug. 19, 2011—Specification of U.S. Appl. No. 09/703,399 as filed.
Dyax Exhibit 1031, Filed in Interference No. 105,809, Filed Aug. 19, 2011—Ma et al., "Plasmid construction by homologous recombination in yeast" (1987).
Dyax Exhibit 1032, Filed in Interference No. 105,809, Filed Aug. 19, 2011—Wood et al., "The synthesis and in vivo assembly of functional antibodies in yeast" (1985).
Dyax Exhibit 1033, Filed in Interference No. 105,809, Filed Aug. 19, 2011—Weaver-Feldhaus et al., "Yeast mating for combinatorial Fab library generation and surface display" (2004).
Dyax Exhibit 1034, Filed in Interference No. 105,809, Filed Aug. 19, 2011—Shen et al., "Delineation of Functional Regions within the Subunits of the *Saccharomyces cerevisiae* Cell Adhesion Molecule a-Agglutinin" (2001).
Dyax Exhibit 1035, Filed in Interference No. 105,809, Filed Aug. 19, 2011—Ma et al., "Association of Transport-Defective Light Chains with Immunoglobulin Heavy Chain Binding Protein" (1990).
Dyax Exhibit 1036, Filed in Interference No. 105,809, Filed Aug. 19, 2011—Colby et al., "Development of a Human Light Chain Variable Domain ($V_L$) Intracellular Antibody Specific for the Amino Terminus of Huntingtin via Yeast Surface Display" (2004).
Dyax Exhibit 1037, Filed in Interference No. 105,809, Filed Aug. 19, 2011—U.S. Pat. No. 4,946,778 Issued Aug. 7, 1990.
Dyax Exhibit 1038, Filed in Interference No. 105,809, Filed Aug. 19, 2011—Hamilton and Gerngross "Glycosylation engineering in yeast: the advent of fully humanized yeast" (2007).
Dyax Exhibit 1039, Filed in Interference No. 105,809, Filed Aug. 19, 2011—Bird et al., "Single-Chain Antigen-Binding Proteins" (1998).
Dyax Exhibit 1040, Filed in Interference No. 105,809, Filed Aug. 19, 2011—Boder and Wittrup "Yeast Surface Display for Directed Evolution of Protein Expression, Affinity, and Stability" (2000).
Dyax Exhibit 1041, Filed in Interference No. 105,809, Filed Aug. 19, 2011—First Declaration of Nathalie Scholler, M.D., Ph.D. filed Aug. 19, 2011.
Dyax Exhibit 1042, Filed in Interference No. 105,809, Filed Aug. 19, 2011—U.S. Appl. No. 11/593,957: Non-final Office Action dated Aug. 12, 2008.
Dyax Exhibit 1043, Filed in Interference No. 105,809, Filed Aug. 19, 2011—U.S. Appl. No. 11/593,957: Adimab's response to the Non-final Office Action filed Jan. 13, 2009.

(56) References Cited

OTHER PUBLICATIONS

Dyax Exhibit 1044, Filed in Interference No. 105,809, Filed Aug. 19, 2011—First Declaration of Li Zhu, Ph.D. dated Jan. 13, 2009.
Dyax Exhibit 1045, Filed in Interference No. 105,809, Filed Aug. 19, 2011—U.S. Appl. No. 11/593,957: Final Office Action dated Apr. 8, 2009.
Dyax Exhibit 1046, Filed in Interference No. 105,809, Filed Aug. 19, 2011—U.S. Appl. No. 11/593,957: Adimab's response to Final Office Action filed Oct. 7, 2009.
Dyax Exhibit 1047, Filed in Interference No. 105,809, Filed Aug. 19, 2011—Second Declaration of Li Zhu, Ph.D. filed Oct. 7, 2009.
Dyax Exhibit 1048, Filed in Interference No. 105,809, Filed Aug. 19, 2011—U.S. Appl. No. 11/593,957: Request to Change Inventorship under 37 C.F.R. § 1.48(b) filed Oct. 7, 2009.
Dyax Exhibit 1049, Filed in Interference No. 105,809, Filed Aug. 19, 2011—Sambrook et al., "Molecular Cloning: A Laboratory Manual" (1989).
Dyax Exhibit 1050, Filed in Interference No. 105,809, Filed Aug. 19, 2011—Claim chart showing disclosures in the '472 patent for claim 1 of the '302 patent.
Dyax Exhibit 1051, Filed in Interference No. 105,809, Filed Aug. 19, 2011—Claim chart showing disclosure in the '472 patent for claims 2-15 of the '302 patent.
Dyax Exhibit 1052, Filed in Interference No. 105,809, Filed Aug. 19, 2011—Claim chart showing disclosures in Boder for claim 1 of the '302 patent.
Dyax Exhibit 1053, Filed in Interference No. 105,809, Filed Aug. 19, 2011—Claim chart showing disclosures in Boder for claims 2-15 of the '302 patent.
Dyax Exhibit 1054, Filed in Interference No. 105,809, Filed Aug. 19, 2011—Claim chart showing disclosures in Boder and Walhout for claim 1 of the '302 patent.
Dyax Exhibit 1055, Filed in Interference No. 105,809, Filed Aug. 19, 2011—Claim chart showing disclosures in Boder and Walhout for claim 2-15 of the '302 patent.
Dyax Exhibit 1056, Filed in Interference No. 105,809, Filed Aug. 19, 2011—An on-line document showing publication date of Methods in Enzymology, vol. 328.
Dyax Exhibit 1057, Filed in Interference No. 105,809, Filed Aug. 19, 2011—Karu et al., "Recombinant Antibody Technology" (1995).
Dyax Exhibit 1058, Filed in Interference No. 105,809, Filed Aug. 19, 2011—U.S. Appl. No. 11/593.957: Complete File History.
Dyax Exhibit 1059, Filed in Interference No. 105,809, Filed Sep. 30, 2011—U.S. Appl. No. 12/625,337: Fourth Preliminary Amendment filed Sep. 30, 2011.
Dyax Exhibit 1060, Filed in Interference No. 105,809, Filed Sep. 30, 2011—Souriau and Hudson "Recombinant antibodies for cancer diagnosis and therapy" (2001).
Dyax Exhibit 1061, Filed in Interference No. 105,809, Filed Sep. 30, 2011—Liu et al., "Rapid Construction of Recombinant DNA by the Univector Plasmid-Fusion System" (2000).
Dyax Exhibit 1062, Filed in Interference No. 105,809, Filed Sep. 30, 2011—Hua et al., "Construction of a modular yeast two-hybrid cDNA library from human EST clones for the human genome protein linkage map" (1998).
Dyax Exhibit 1063, Filed in Interference No. 105,809, Filed Sep. 30, 2011—Abbas et al., Cellular and Molecular Immunology, 4th ed., W.B. Saunders Co. (2000).
Dyax Exhibit 1064, Filed in Interference No. 105,809, Filed Sep. 30, 2011—Burke et al., "Methods in Yeast Genetics" (2000).
Dyax Exhibit 1065, Filed in Interference No. 105,809, Filed Sep. 30, 2011—U.S. Appl. No. 12/625,337: Third Preliminary Amendment and Suggestion of an Interference under 37 C.F.R. § 41.202(a) filed Jan. 24, 2011.
Dyax Exhibit 1066, Filed in Interference No. 105,809, Filed Sep. 30, 2011—Alberts et al., "Molecular Biology of The Cell Third Edition" (1994).
Dyax Exhibit 1067, Filed in Interference No. 105,809, Filed Sep. 30, 2011—U.S. Appl. No. 10/262,646, filed Sep. 30, 2002.
Dyax Exhibit 1068, Filed in Interference No. 105,809, Filed Sep. 30, 2011—U.S. Appl. No. 60/326,320, filed Oct. 1, 2001.
Dyax Exhibit 1069, Filed in Interference No. 105,809, Filed Sep. 30, 2011—Adimab's Substantive Motion 2 (for no interference-infact) filed Aug. 19, 2011.
Dyax Exhibit 1070, Filed in Interference No. 105,809, Filed Sep. 30, 2011—Marks et al., "By-passing Immunization Human Antibodies from V-gene Libraries Displayed on Phage" (1991).
Dyax Exhibit 1071, Filed in Interference No. 105,809, Filed Sep. 30, 2011—Abbas et al., Cellular and Molecular Immunology, Fourth Edition—Section III Maturation, Activation, and Regulation of Lymphocytes (2000).
Dyax Exhibit 1072, Filed in Interference No. 105,809, Filed Sep. 30, 2011—Second Declaration of Nathalie Scholler, M.D., Ph.D. dated Sep. 29, 2011.
Dyax Exhibit 1073, Filed in Interference No. 105,809, Filed Sep. 30, 2011—U.S. Appl. No. 10/262,646: Final Office Action with Restriction Requirement dated Mar. 9, 2005.
Dyax Exhibit 1074, Filed in Interference No. 105,809, Filed Sep. 30, 2011—U.S. Appl. No. 10/262,646: Response to Restriction Requirement filed Apr. 8, 2005.
Dyax Exhibit 1075, Filed in Interference No. 105,809, Filed Sep. 30, 2011—U.S. Appl. No. 12/625,337: Amendment and Response to Notice to File Missing Parts filed Aug. 17, 2010.
Dyax Exhibit 1076, Filed in Interference No. 105,809, Filed Nov. 21, 2011—Curriculum Vitae for David M. Kranz, Ph.D.
Dyax Exhibit 1077, Filed in Interference No. 105,809, Filed Nov. 21, 2011—Woods and Gietz "High-Efficiency Transformation of Plasmid DNA into Yeast", Methods in Molecular Biology, vol. 177.
Dyax Exhibit 1078, Filed in Interference No. 105,809, Filed Nov. 21, 2011—David M. Kranz, Ph.D. biography from the University of Illinois.
Dyax Exhibit 1079, Filed in Interference No. 105,809, Filed Nov. 21, 2011—US Patent Application 2001/0037016 Published Nov. 1, 2001.
Dyax Exhibit 1080, Filed in Interference No. 105,809, Filed Nov. 21, 2011—US Patent Publication No. US 2002/0026653 Published Feb. 28, 2002.
Dyax Exhibit 1081, Filed in Interference No. 105,809, Filed Nov. 21, 2011—US Patent Publication No. US 2002/0037280 Published Mar. 28, 2002.
Dyax Exhibit 1082, Filed in Interference No. 105,809, Filed Nov. 21, 2011—Alberts et al., Molecular Biology of The Cell, Forth Edition, pp. 293-294 (2001).
Dyax Exhibit 1083, Filed in Interference No. 105,809, Filed Nov. 21, 2011—Alberts et al., Molecular Biology of The Cell, Forth Edition, pp. 540-541 (2001).
Dyax Exhibit 1084, Filed in Interference No. 105,809, Filed Nov. 21, 2011—The Hena Protein-Protein Interaction Webpage print out.
Dyax Exhibit 1085, Filed in Interference No. 105,809, Filed Nov. 21, 2011—Deposition of David M. Kranz, Ph.D. dated Oct. 14, 2011.
Dyax Exhibit 1086, Filed in Interference No. 105,809, Filed Nov. 21, 2011—Deposition of Nathalie Scholler, M.D., Ph.D. dated Oct. 24, 2011.
Dyax Exhibit 1087, Filed in Interference No. 105,809, Filed Nov. 21, 2011—In-Fusion SMARTer Directional cDNA Library Construction Kit User Manual Clontech—Jun. 2011.
Dyax Exhibit 1088, Filed in Interference No. 105,809, Filed Nov. 21, 2011—US Patent Publication No. US 2003/0091995 Published May 15, 2003.
Dyax Exhibit 1089, Filed in Interference No. 105,809, Filed Nov. 21, 2011—US Patent Publication No. US 2001/0041333 Published Nov. 15, 2001.
Dyax Exhibit 1090, Filed in Interference No. 105,809, Filed Nov. 21, 2011—Sheets et al., "Efficient construction of a large nonimmune phage antibody library: The production of high-affinity human single-chain antibodies to protein antigens" (1998).
Dyax Exhibit 1091, Filed in Interference No. 105,809, Filed Nov. 21, 2011—Third Declaration of Nathalie Scholler, M.D., Ph.D. dated Nov. 20, 2011.

(56) References Cited

OTHER PUBLICATIONS

Dyax Exhibit 1092, Filed in Interference No. 105,809, Filed Nov. 21, 2011—Shusta et al., "Yeast Polypeptide Fusion Surface Display Levels Predict Thermal Stability and Soluble Secretion Efficiency" (1999).
Dyax Exhibit 1093, Filed in Interference No. 105,809, Filed Jan. 20, 2012—Boder et al., "Yeast Surface Display of a Noncovalent MHC Class II Heterodimer Complexed With Antigenic Peptide" (2005).
Dyax Exhibit 1094, Filed in Interference No. 105,809, Filed Jan. 20, 2012—Pepper et al., "A Decade of Yeast Surface Display Technology: Where Are We Now?" (2008).
Dyax Exhibit 1095, Filed in Interference No. 105,809, Filed Jan. 20, 2012—Alberts et al., Molecular Biology of The Cell, Fourth Edition (2002).
Dyax Exhibit 1096, Filed in Interference No. 105,809, Filed Jan. 20, 2012—Lin et al., "Display of a functional hetero-oligomeric catalytic antibody on the yeast cell surface" (2002).
Dyax Exhibit 1097, Filed in Interference No. 105,809, Filed Jan. 20, 2012—Hubberstey and Wildeman, "Use of interplasmid recombination to generate stable selectable markers for yeast transformation: application to studies of actin gene control" (1990).
Dyax Exhibit 1098, Filed in Interference No. 105,809, Filed Jan. 20, 2012—Dielbandhoesing et al., "Specific Cell Wall Proteins Confer Resistance to Nisin upon Yeast Cells" (1998).
Dyax Exhibit 1099, Filed in Interference No. 105,809, Filed Jan. 20, 2012—Sed1p {*Saccharomyces cerevisiae* S288c]—Protein—NCBI Reference Sequence: NP_010362.1.
Dyax Exhibit 1100, Filed in Interference No. 105,809, Filed Jan. 20, 2012—Tip1p [*Saccharomyces cerevisiae* S288c]—Protein—NCBI Reference Sequence: NP_009623.1.
Dyax Exhibit 1101, Filed in Interference No. 105,809, Filed Jan. 20, 2012—Deposition of David M. Kranz, Ph.D. dated Oct. 14, 2011.
Dyax Exhibit 1102, Filed in Interference No. 105,809, Filed Jan. 20, 2012—Tsubouchi and Roeder, "Budding yeast Hed1 down-regulates the mitotic recombination machinery when meiotic recombination is impaired" (2006).
Dyax Exhibit 1103, Filed in Interference No. 105,809, Filed Jan. 20, 2012—Sample Campaign << Adimab, Webpage from www.adimab.com/science-and-technology/technology-overview/sample campaign.
Dyax Exhibit 1104, Filed in Interference No. 105,809, Filed Jan. 20, 2012 Corporate Overview << Adimab, Webpage from www.adimab.com/about-adimab/corporate-overview.
Dyax Exhibit 1105, Filed in Interference No. 105,809, Filed Jan. 20, 2012—Manivasakam and Schiestl, High efficiency transformation of *Saccharomyces cerevisiae* by electroporation (1993).
Dyax Exhibit 1106, Filed in Interference No. 105,809, Filed Jan. 20, 2012—Kranz and Voss, "Restricted reassociation of heavy and light chains from hapten-specific monoclonal antibodies" (1981).
Dyax Exhibit 1107, Filed in Interference No. 105,809, Filed Jan. 20, 2012—Decision on Motions and Order for Patent Interference No. 104,424 dated Jul. 28, 2000.
Dyax Exhibit 1108, Filed in Interference No. 105,809, Filed Jan. 20, 2012—Stemmer, W. "DNA shuffling by random fragmentation and reassembly: In vitro recombination for molecular evolution" (1993/1994).
Dyax Exhibit 1109, Filed in Interference No. 105,809, Filed Jan. 20, 2012—Deposition of Eric T. Boder, Ph.D. dated Dec. 20, 2011.
Dyax Exhibit 1110, Filed in Interference No. 105,809, Filed Jan. 20, 2012—Second Deposition of David M. Kranz, Ph.D. dated Jan. 3, 2012.
Dyax Exhibit 1111, Filed in Interference No. 105,809, Filed Jan. 20, 2012—Second Deposition of Nathalie Scholler, M.D., Ph.D. dated Jan. 12, 2012.
Dyax Exhibit 1112, Filed in Interference No. 105,809, Filed Jan. 20, 2012—Fourth Declaration of Nathalie Scholler, M.D., Ph.D. dated Jan. 19, 2012.
Dyax Exhibit 1113, Filed in Interference No. 105,809, Filed Jan. 20, 2012—Decision of Yager Miscellaneous Motion 4, filed in Interference No. 104,718 filed Mar. 11, 2002.
Dyax Exhibit List, Filed in Interference No. 105,809, Filed Jan. 20, 2012.
Dyax Exhibit List, Filed in Interference No. 105,809, Filed Aug. 19, 2011.
Dyax Exhibit List, Filed in Interference No. 105,809, Filed Sep. 30, 2011.
Dyax List of Exhibits, Filed in Interference No. 105,809, Filed Nov. 21, 2011.
Dyax list of proposed motions, Filed in Interference No. 105,809, Filed Jun. 28, 2011.
Dyax Miscellaneous Motion 1, Filed in Interference No. 105,809, Filed Feb. 3, 2012.
Dyax Notice of Exhibits Served, Filed in Interference No. 105,809, Filed Aug. 19, 2011.
Dyax Notice of Filing of Priority Statement, Filed in Interference No. 105,809, Filed Aug. 19, 2011.
Dyax Notice of Service of Exhibits, Filed in Interference No. 105,809, Filed Jan. 20, 2012.
Dyax Notice of Service of Exhibits, Filed in Interference No. 105,809, Filed Nov. 21, 2011.
Dyax Notice of Service of Priority Statement, Filed in Interference No. 105,809, Filed Aug. 26, 2011.
Dyax Opposition 1, Filed in Interference No. 105,809, Filed Nov. 21, 2011.
Dyax Opposition 2, Filed in Interference No. 105,809, Filed Nov. 21, 2011.
Dyax Opposition 3, Filed in Interference No. 105,809, Filed Nov. 21, 2011.
Dyax Opposition 4, Filed in Interference No. 105,809, Filed Nov. 21, 2011.
Dyax Opposition 5, Filed in Interference No. 105,809, Filed Nov. 21, 2011.
Dyax Opposition 6, Filed in Interference No. 105,809, Filed Nov. 21, 2011.
Dyax Priority Statement, Filed in Interference No. 105,809, Filed Aug. 19, 2011.
Dyax Reply 1, Filed in Interference No. 105,809, Filed Jan. 20, 2012.
Dyax Reply 2, Filed in Interference No. 105,809, Filed Jan. 20, 2012.
Dyax Reply 3, Filed in Interference No. 105,809, Filed Jan. 20, 2012.
Dyax Reply 4, Filed in Interference No. 105,809, Filed Jan. 20, 2012.
Dyax Request for Oral Argument, Filed in Interference No. 105,809, Filed Feb. 3, 2012.
Dyax Responsive Motion 4, Filed in Interference No. 105,809, Filed Sep. 30, 2011.
Dyax Second Notice of Discussions, Filed in Interference No. 105,809, Filed Oct. 6, 2011.
Dyax Substantive Motion 1, Filed in Interference No. 105,809, Filed Aug. 19, 2011.
Dyax Substantive Motion 2, Filed in Interference No. 105,809, Filed Aug. 19, 2011.
Dyax Substantive Motion 3, Filed in Interference No. 105,809, Filed Aug. 19, 2011.
Ehlers, M.D., "Synapse structure: glutamate receptors connected by the shanks" Current Biol., 9(22): R848-850 (1999).
Fan, Z. and Mendelsohn, J., "Therapeutic application of anti-growth factor receptor antibodies" Curr. Opin. Oncol., 10(1):67-73 (1998).
Fan, Z. et al., "Three-dimensional structure of an Fv from a human IgM immunoglobulin" J. Mol. Biol., 228(1):188-207 (1992).
Feldhaus, M.J. et al., "Oligonucleotide-conjugated beads for transdominant genetic experiments" Nucleic Acids Research, 28(2):534-543 (2000).
Fellouse, F.A. et al., "High-throughput Generation of Synthetic Antibodies from Highly Functional Minimalist Phage-displayed Libraries" J. Mol. Biol. 373(4):924-940 (2007).
Fellouse, F.A. et al., "Molecular Recognition by a Binary Code" J. Mol, Biol. 348(5):1153-1162 (2005).
Fellouse, F.A. et al., "Synthetic antibodies from a four-amino-acid code: a dominant role for tyrosine in antigen recognition" PNAS, 101(34):12467-12472 (2004).

(56) References Cited

OTHER PUBLICATIONS

Fields, S. and Sternglanz, R., "The two-hybrid system: an assay for protein-protein interactions" Trends Genet.,10(8):286-292 (1994).
Fields. S. and Song, O., "A novel genetic system to detect protein-protein interactions" Nature, 340(6230):245-246 (1989).
Finley R.L., Jr. and Brent, R., "Interaction mating reveals binary and ternary connections between Drosophila cell cycle regulators" Proc. Natl. Acad. Sci. USA, 91(26):12980-12984 (1994).
Firth, A.E. and Patrick, W.M., "GLUE-IT and PEDEL-AA: new programmes for analyzing protein diversity in randomized libraries" Nucleic Acids Res., 36:W281-W285 (2008).
Frazer, J. K., and J. D. Capra, "Immunoglobulins: Structure and Function", in Fundamental Immunology, Fourth Edition, William E. Paul, ed., Lippincot-Raven Publishers, Philadelphia, pp. 41-43 and 51-52 (1999).
Fromont-Racine, M. et al., "Toward a functional analysis of the yeast genome through exhaustive two-hybrid screens" Nat. Genet., 16(3):277-282 (1997).
Frykman, S. and Srienc, F., "Quantitating secretion rates of individual cells: design of secretion assays" Biotechnol. & Bioeng., 59(2):214-226 (1998).
Fuh, G., "Synthetic antibodies as therapeutics" Expert Opin. Biol. Ther., 7(1):73-87 (2007).
Garcia, R.A. et al., "The neuregulin receptor ErbB-4 interacts with PDZ■containing proteins at neuronal synapses" Proc. Natl. Acad Sci USA, 97(7):3596-3601 (2000).
Gietz et al., "Improved method for high efficiency transformation of intact yeast cells" Nucleic Acids Res., 20(6):1425 (1992).
Gietz, R.D. and R.H. Schiestl, "Transforming Yeast with DNA" Methods in Molecular and Cellular Biology (Invited Chapter), 5:255-269 (1995).
Gilfillan, S. et al., "Efficient immune responses in mice lacking N-region diversity" Eur. J. Immunol., 25(11):3115-3122 (1995).
Griffiths, A.D. et al., "Human anti-self antibodies with high specificity from phage display libraries" EMBO J., 12(2):725-734 (1993).
Griffiths, A.D. et al., "Isolation of high affinity human antibodies directly from large synthetic repertoires," EMBO J., 13(14):3245-3260 (1994).
Grimes E. et al., "Achilles' heel cleavage: creation of rare restriction sites in lambda phage genomes and evaluation of additional operators, repressors and restriction/modification systems" Gene, 90(1):1-7 (1990).
Gushiken, F.C. et al., "Polymorphism of beta2-glycoprotein I at codons 306 and 316 in patients with systemic lupus erythematosus and antiphospholipid syndrome" Arthritis & Rheumatism, 42(6):1189-1193 (1999).
Hanes, J. et al., "Picomolar affinity antibodies from a fully synthetic naive library selected and evolved by ribosome display" Nat Biotechnol. 18:(12):1287-1292 (2000).
Hasan, N. and Szybalski, W., "Control of cloned gene expression by promoter inversion in vivo: construction of improved vectors with a multiple cloning site and the Ptac promoter" Gene, 56(1):145-151 (1987).
Hawkins, R.E. and Winter, G., "Cell selection strategies for making antibodies from variable gene libraries: trapping the memory pool" Eur. J. Immunol., 22(3):867-870 (1992).
He, M. and Taussig, M.J., "Antibody-ribosome-mRNA (ARM) complexes as efficient selection particles for in vitro display and evolution of antibody combining sites" Nucleic Acids Res., 25(24):5132-5134 (1997).
Heddle, R.J. and Rowley, D., "Dog Immunoglobulins, I. immunochemical characterization of dog serum, parotid saliva, colostrum, milk and small bowel fluid" Immunology, 29(1):185-195 (1975).
Hoet, R.M. et al., "Generation of high-affinity human antibodies by combining donor-derived and synthetic complementarity-determining-region diversity" Nat. Biotechnol., 23(3):344-348 (2005).
Hoet, R.M. et al., "The importance of the light chain for the epitope specificity of human anti-U1 small nuclear RNA autoantibodies present in systemic lupus erythematosus patients" Journal of Immunology,163(6):3304-3312 (1999).
Holmes, P. and Al-Rubeai, M., "Improved cell line development by a high throughput affinity capture surface display technique to select for high secretors" J. Immunol. Methods, 230(1-2):141-147 (1999).
Hoogenboom, H.R. and Winter, G., "By-passing immunisation. Human antibodies from synthetic repertoires of germline VH gene segments rearranged in vitro" J. Mol. Biol., 227(2):381-388 (1992).
Hoogenboom, H.R. et al., "Antibody phage display technology and its applications" Immunotechnology, 4(1):1-20 (1998).
Hoogenboom, H.R. et al., "Multi-subunit proteins on the surface of filamentous phage: methodologies for displaying antibody (Fab) heavy and light chains" Nucleic Acids Research, 19(15):4133-4137 (1991).
Hoogenboom, H.R., "Designing and optimizing library selection strategies for generating high-affinity antibodies" Trends Biotechnol. 15(2):62-70 (1997).
Hoshino, Y. et al., "The rational design of a synthetic polymer nanoparticle that neutralizes a toxic peptide in vivo" PNAS 109(1):33-38 (2012).
Hrncir, Z. and Chýiková et al., "[Anticardiolipin antibodies in diffuse connective tissue diseases in the IgG, IgM and IgA isotypes]" Vnitr. Lek., 36(11):1041-1049 (1990), translation (provided by USPTO) pp. 1-13 (1999).
Hua, S.B. et al., "Construction of a modular yeast two-hybrid cDNA library from human EST clones for the human genome protein linkage map" Gene, 215(1):143-152 (1998).
Hua, S.B. et al., "Minimum length sequence homology required for in vivo cloning by homologous recombination in yeast" Plasmid, 38(2):91-96 (1997).
Huang, D. and Shusta, E.V. et al., "Secretion and surface display of green fluorescent protein using the yeast *Saccharomyces cerevisiae*" Biotechnol. Prog., 21(2):349-357 (2005).
Huse, W.D. et al., "Generation of a large combinatorial library of the immunoglobin repertoire in phage lambda" Science 246(4935):1275-1281 (1989).
Huston, J.S. et al., "Protein engineering of antibody binding sites: recovery of specific activity in an anti-digoxin single-chain Fv analogue produced in *Escherichia coli*" Proc. Natl. Acad. Sci. USA 85(16):5879-5883 (1988).
Ivanov, I.I. et al., "Development of the expressed Ig CDR-H3 repertoire is marked by focusing of constraints in length, amino acid use, and charge that are first established in early B cell progenitors," J. Immunol., 174(12):7773-7780 (2005).
Jackson, K.J., et al., "Identifying highly mutated IGHD genes in the junctions of rearranged human immunoglobin heavy chain genes," J. Immunol. Methods, 324(1-2):26-37 (2007).
Jacobsson, K. and Frykberg, L., "Phage Display Shot-Gun Cloning of Ligand-Binding Domains of Prokaryotic Receptors Approaches 100% Correct Clones" BioTechniqes, 20(6):1078, 1080-1081 (1996).
Jirholt, P. et al., "Exploiting sequence space: shuffling in vivo formed complementarity determining regions into a master framework", Gene, 215(2):471-476 (1998).
Johns M. et al., "In vivo selection of sFv from phage display libraries" J. Immunol. Methods, 239(1-2):137-151 (2000).
Juul, L. et al., "The normally expressed kappa immunoglobulin light chain gene repertoire and somatic mutations studied by single-sided specific polymerase chain reaction (PCR); frequent occurrence of features often assigned to autoimmunity" Clin. Exp. Immunol., 109(1):194-203 (1997).
Kaczorowski, T. and Szybalski, W., "Genomic DNA sequencing by SPEL-6 primer walking using hexamer ligation" Gene, 223(1-2):83-91 (1998).
Kang, A.S. et al., "Linkage of recognition and replication functions by assembling combinatorial antibody Fab libraries along phage surfaces" Proc. Natl. Acad. Sci., 88(10):4363-4666 (1991).
Kieke, M.C. et al., "Isolation of anti-T cell receptor scFv mutants by yeast surface display". Protein Eng. 10(11):1303-1310 (1997).

(56) References Cited

OTHER PUBLICATIONS

Kim, S.C. et al., "Cleaving DNA at any predetermined site with adapter-primers and class-IIS restriction enzymes" Science, 240(4851):504-506 (1988).
Kim, S.C., et al., "Structural requirements for FokI-DNA interaction and oligodeoxyribonucleotide-instructed cleavage" J. Mol. Biol., 258(4):638-649 (1996).
Klein, R. et al., "Expressed human immunoglobulin kappa genes and their hypermutation" Eur. J. Immunol., 23(12):3248-3262 (1993).
Knappik, A. et al., "Fully synthetic human combinatorial antibody libraries (HuCAL) based on modular consensus frameworks and CDRs randomized with trinucleotides" J. Mol. Biol., 296(1):57-86 (2000).
Koiwai, O. et al., "Isolation and characterization of bovine and mouse terminal deoxynucleotidyltransferase cDNAs expressible in mammalian cells" Nucleic Acids Res., 14(14):5777-5792 (1986).
Kontermann, R.E. and Müller, R., "Intracellular and cell surface displayed single-chain diabodies", J. Immunol. Methods, 226(1-2):179-188 (1999).
Koob, M. and Szybalski, W., "Cleaving yeast and *Escherichia coli* genomes at a single site" Science, 250(4978):271-273 (1990).
Koob, M. et al., "Conferring new specificity upon restriction endonucleases by combining repressor-operator interaction and methylation" Gene, 74(1):165-167 (1988).
Koob, M. et al., "Conferring operator specificity on restriction endonucleases," Science, 241(4869):1084-1086 (1988).
Koob, M. et al., "RecA-Ac: single-site cleavage of plasmids and chromosomes at any predetermined restriction site" Nucleic Acids Res., 20(21):5831-5836 (1992).
Kostrub, C.F. et al., "Use of gap repair in fission yeast to obtain novel alleles of specific genes" Nucleic Acids Research, 26(20):4783-4784 (1998).
Kretzschmar, T. and von Rüden, T., "Antibody discovery: phage display" Curr. Opin. Biotechnol., 13(6):598-602 (2002).
Kur, J. et al., "A novel method for converting common restriction enzymes into rare cutters: integration host factor-mediated Achilles' cleavage (IHF-AC)" Gene, 110(1):1-7 (1992).
Lake, D.F. et al., "Generation of diverse single-chain proteins using a universal (Gly4-Ser)3 encoding oligonucleotide" BioTechniques, 19(5):700-702 (1995).
Lecrenier, N., et al., "Two-hybrid systematic screening of the yeast proteome" Bioessays. 20(1):1-5 (1998).
Lederman, S. et al., "A single amino acid substitution in a common African allele of the CD4 molecule ablates binding of the monoclonal antibody, OKT4" Mol Immunol. (11):1171-81 (1991).
Lee, C.E., et al., "Reconsidering the human immunoglobulin heavy-chain locus: 1. An evaluation of the expressed human IGHD gene repertoire" Immunogenetics, 57(12):917-925 (2006).
Lee, C.V. et al., "High-affinity human antibodies from phage-displayed synthetic Fab libraries with a single framework scaffold" J. Mol. Biol. 340(5):1073-1093 (2004).
Lee, S.Y. et al., "Microbial cell-surface display" Trends Biotechnol., 21(1):45-52 (2003).
Leonard, B. et al., "Co-expression of antibody fab heavy and light chain genes from separate evolved compatible replicons in *E. coli*" J. Immunol. Methods, 317(1-2):56-63 (2006).
Lerner, R.A. et al.,"Antibodies without immunization" Science,258(5086):1313-314 (1992).
Lezcano, N. et al., "Dual Signaling Regulated by Calcyon, a D1 Dopamine Receptor Interacting Protein" Science, 287(5458):1660-1664 (2000).
Li, C.H. et al., "beta-Endorphin omission analogs: dissociation of immunoreactivity from other biological activities" Proc Natl Acad Sci USA. 177(6):3211-3214 (1980).
Li, H. et al., "Biofuels: Biomolecular Engineering Fundamentals and Advances" Annu. Rev. Chem. Biomol. Eng. 1:19-36 (2010).
Li, N. et al., "B-Raf kinase inhibitors for cancer treatment" Current Opinion in Investigational Drugs 8(6) 452-456 (2007).

List of Exhibits, Filed in Interference No. 105,809, Filed Aug. 19, 2011.
Little, M. et al., "Generation of a large complex antibody library from multiple donors" J. Immunol Methods, 231(1-2):3-9 (1999).
Liu, Q. et al., "Rapid construction of recombinant DNA by the univector plasmid-fusion system" Methods Enzymol. 328:530-49 (2000).
Love J.C. et al., "A microengraving method for rapid selection of single cells producing antigen-specific antibodies" Nature Biotechnol. 24(6):703-707 (2006).
Lowman, H.B. and Wells, J.A., "Affinity maturation of human growth hormone by monovalent phage display" J. Mol. Biol., 234(3):564-578 (1993).
Lowman, H.B. et al., "Selecting high-affinity binding proteins by monovalent phage display" Biochemistry, 30(45):10832-10838 (1991).
Manz, R. et al., "Analysis and sorting of live cells according to secreted molecules, relocated to a cell-surface affinity matrix" Proc. Natl. Acad. Sci. USA, 92(6):1921-1925 (1995).
Marks, J.D. et al., "By-passing Immunization. Human Antibodies from V-gene Libraries Displayed on Phage" J. Mol. Biol., 222(3):581-597 (1991).
Marks, J.D. et al., "By-passing Immunization: building high affinity human antibodies by chain shuffling" Biotechnology (NY), 10(7):779-783 (1992).
Martin, A.C., "Accessing the Kabat antibody sequence database by computer" Proteins, 25(1):130-133 (1996).
Martin, A.C.and Thornton, J.M., "Structural families in loops of homologous proteins: automatic classification, modelling and application to antibodies" J. Mol. Biol., 263(5):800-815 (1996).
Marzari, R. et al., "Extending filamentous phage host range by the grafting of a heterologous receptor binding domain" Gene, 185(1):27-33 (1997).
Matsuda, F. et al., "The complete nucleotide sequence of the human immunoglobulin heavy chain variable region locus" J. Exp. Med., 188(11):2151-2162 (1998).
Mattila, P.S. et al., "Extensive allelic sequence variation in the J region of the human immunoglobulin heavy chain gene locus" Eur. J. Immunol., 9(:)2578-2582 (1995).
Mazor Y. et al., "Isolation of engineered, full-length antibodies from libraries expressed in *Escherichia coli*" Nature Biotecnol., 25(5):563-565 (2007).
McCafferty, J. et al., "Phage antibodies: filamentous phage displaying antibody variable domains" Nature, 348(6301):552-554.
Mimran, A. et al., "GCN4-Based Expression System (pGES): Translationally Regulated Yeast Expression Vectors" BioTechniques, 28(3):552-554, 556, 558-560 (2000).
Moll, J.R. et al., "Designed heterodimerizing leucine zippers with a ranger of pIs and stabilities up to 10(-15) M" Protein Science, 10(3):649-55 (2001).
Mollova, S. et al., "Visualising the immune repertoire" BMC Systems Biology, 1(S1):P30 (2007).
Mouquet, H. et al., "Enhanced HIV-1 neutralization by antibody heteroligation" PNAS Early Edition 1-6.
Mullinax, R.L. et al., "Identification of human antibody fragment clones specific for tetanus toxoid in a bacteriophage lambda immunoexpression library" Proc. Natl. Acad. Sci., 87(20):8095-8099 (1990).
Mézard, C. et al., "Recombination between similar but not identical DNA sequences during yeast transformation occurs within short stretches of identity" Cell, 70(4):659-670 (1992).
Nakamura, Y. et al., "Development of novel whole-cell immunoadsorbents by yeast surface display of the IgG-binding domain" Appl. Microbiol. Biotechnol., 57(4):500-505 (2001).
Nishigaki, K. et al., "Type II restriction endonucleases cleave single-stranded DNAs in general" Nucleic Acids Res, 13(16):5747-5760 (1985).
Notice Designating pro hac vice counsel, Filed in Interference No. 105,809, Filed Oct. 6, 2011.
Notice of 4th Preliminary Amendment in Reissue Application, Filed in Interference No. 105,809, Filed Sep. 30, 2011.
Notice of Discussions, Filed in Interference No. 105,809, Filed Aug. 12, 2011.

(56) References Cited

OTHER PUBLICATIONS

Notice of Exhibits List Filed, Filed in Interference No. 105,809, Filed Nov. 21, 2011.
Notice of Filing Continuation of Reissue Application, Filed in Interference No. 105,809, Filed Sep. 30, 2011.
Notice of Filing of Adimab Priority Statement, Filed in Interference No. 105,809, Filed Aug. 19, 2011.
Notice of Filing of Continuation Application, Filed in Interference No. 105,809, Filed Nov. 21, 2011.
Notice of Filing of Reissue Application, Filed in Interference No. 105,809, Filed Aug. 19, 2011.
Notice of Filing of Reissue of U.S. Pat. No. 7,005,503, Filed in Interference No. 105,809, Filed Nov. 21, 2011.
Notice of Filing of Reissue of U.S. Pat. No. 7,138,496, Filed in Interference No. 105,809, Filed Nov. 21, 2011.
Notice of related proceedings filed during interference, Filed in Interference No. 105,809, Filed Jun. 28, 2011.
Notice of Related Proceedings, Filed in Interference No. 105,809, Filed May 20, 2011.
Notice of Second Preliminary Amendment in Reissue Applicatio, Filed in Interference No. 105,809, Filed Aug. 19, 2011.
Notice of Service of Dyax Exhibits, Filed in Interference No. 105,809, Filed Sep. 30, 2011.
Notice of Stipulated Extension, Filed in Interference No. 105,809, Filed Sep. 2, 2011.
Notice of Stipulation of Extension—Time Period 3, Filed in Interference No. 105,809, Filed Oct. 20, 2011.
Notice of Stipulation of Extension—Time Periods 3 & 4, Filed in Interference No. 105,809, Filed Nov. 1, 2011.
Notice of Stipulation of Extension—Time Periods 4, 5 & 6, Filed in Interference No. 105,809, Filed Dec. 5, 2011.
Notice of Stipulation of Extension of Time Period 2, Filed in Interference No. 105,809, Filed Sep. 21, 2011.
Notice of Stipulation of Extension of Time Period 3, Filed in Interference No. 105,809, Filed Nov. 14, 2011.
Notice of Stipulation of Extension of Time Periods 4, 5, & 6, Filed in Interference No. 105,809, Filed Jan. 12, 2012.
Notice of Stipulation of Extension of Time Periods 5 and 6, Filed in Interference No. 105,809, Filed Jan. 24, 2012.
Oldenburg, K.R et al., "Recombination-mediated PCR-directed plasmid construction in vivo in yeast" Nucleic Acids Res, 25(2):451-452 (1997).
Onda, T. et al., "A phage display system for detection of T cell receptor-antigen interactions" Mol Immunol., 32(17-18):1387-1397 (1995).
Order BD.R. 103 Limited Transfer of Jurisdiction, Filed in Interference No. 105,809, Filed Jul. 25, 2011.
Order BD.R. 104 Authorizing Reply Declaration, Filed in Interference No. 105,809, Filed Dec. 8, 2011.
Order BD.R. 104 Regarding Adimab's Reissue Application, Filed in Interference No. 105,809, Filed Sep. 7, 2011.
Order BD.R. 104, Filed in Interference No. 105,809, Filed Jul. 21, 2011.
Order BD.R. 104-Regarding Related Applications, Filed in Interference No. 105,809, Filed Jul. 1, 2011.
Order BD.R. 109(b)Authorizing Copies of Office Records, Filed in Interference No. 105,809, Filed May 23, 2011.
Order BD.R. 121 Authorizing Motion, Filed in Interference No. 105,809, Filed Aug. 4, 2011.
Order BD.R. 121 Authorizing Motions, Filed in Interference No. 105,809, Filed Sep. 1, 2011.
Order BD.R. 121 Contingently Authorizing Responsive Motion, Filed in Interference No. 105,809, Filed Sep. 13, 2011.
Order BD.R. 121(a) Authorizing Motions, Filed in Interference No. 105,809, Filed Jul. 1, 2011.
Order BD.R. 5(a), Filed in Interference No. 105,809, Filed Sep. 27, 2011.
Ornstein, R.L. et al., "An optimized potential function for the calculation of nucleic acid interaction energies I. Base stacking" Biopolyrners, 17:2341-2360 (1978).

Panka, D.J. et al., "Variable region framework differences result in decreased or increased affinity of variant anti-digoxin antibodies" Proc. Natl. Acad. Sci. USA, 85(9):3080-3084 (1988).
Parrott, M.B. et al., "Metabolically biotinylated adenovirus for cell targeting, ligand screening, and vector purification" Mol. Ther., 8(4):688-700 (2003).
Parthasarathy, R. et al., "An immobilized biotin ligase: surface display of *Escherichia coli* BirA on *Saccharomyces cerevisiae*" Biotechnol. Prog., 21(6):1627-1631 (2005).
Pasqualini, R. and Ruoslahti, E., "Organ targeting in vivo using phage display peptide libraries" Nature, 380(6572):364-366 (1996).
Patrick, W.M. et al., "User-friendly algorithms for estimating completeness and diversity in randomized protein-encoding libraries" Protein Engineering, 16(6):451-457 (2003).
Pearson, B.M. et al., "Construction of PCR-ligated long flanking homology cassettes for use in the functional analysis of six unknown open reading frames from the left and right arms of *Saccharomyces cerevisiae* chromosome XV" Yeast, 14(4):391-399 (1998).
Persson, M.A. et al., "Generation of diverse high-affinity human monoclonal antibodies by repertoire cloning" Proc. Natl. Acad. Sci. USA, 88(6):2432-2436 (1991).
Phizicky, E.M. and Fields, S. et al., "Protein-protein interactions: methods for detection and analysis" Microbiol. Rev. 59(1):94-123 (1995).
Piatesi, A. et al., "Directed evolution for improved secretion of cancer-testis antigen NY-ESO-1 from yeast." Protein Expr. Purif., 48(2):232-42 (2006).
Pickens, L.B. et al., "Metabolic Engineering for the Production of Natural Products" Annu. Rev. Chem. Biomol. Eng. 2:211-236 (2011).
Pini, A. et al., "Design and use of a phage display library. Human antibodies with subnanomolar affinity against a marker of angiogenesis eluted from a two-dimensional gel" Journal of Biological Chemistry, 273(34):21769-21776 (1998).
Pluckthun, A., "Antibody engineering: Advances from the use of *Escherichia coli* expression systems" Biotechnology (NY) 9(6):545-551 (1991).
POA for Mr. Eric Marandett, Filed in Interference No. 105,809, Filed Oct. 6, 2011.
Podhajska A.J. and Szybalski W., "Conversion of the Fokl endonuclease to a universal restriction enzyme: cleavage of a phage M13mp7 DNA at predetermined sites," Gene, 40(2-3):175-182 (1985).
Podhajska A.J. et al., "Conferring new specificities on restriction enzymes: cleavage at any predetermined site by combining adaptor oligodexynucleotide and class-IIS enzyme" Methods in Enzymology, 216(G):303-309 (1992).
Powell, Richard and McLane, Kathryn Evans, "Construction, assembly and selection of combinatorial antibody libraries." Genetic Engineering with PCR (Horton and Tait, Eds. 1998), vol. 5 of the Current Innovations in Molecular Biol series, Horizon Scientific Press.
Prabakaran, P. et al., "Expressed antibody repertoires in human cord blood cells: 454 sequencing and IMGT/High V-QUEST analysis of germline gene usage, junctional diversity, and somatic mutations" Immunogenetics (2011).
Prabakaran, P. et al., Supplemental "Expressed antibody repertoires in human cord blood cells: 454 sequencing and IMGT/High V-QUEST analysis of germline gene usage, junctional diversity, and somatic mutations" Immunogenetics (2011).
Proba, K. et al., "Antibody scFv fragments without disulfide bonds made by molecular evolution". J Mol Biol. 275(2):245-253 (1998).
Pu, W.T. and Struhl, K., "Dimerization of leucine zippers analyzed by random selection". Nucleic Acids Res. vol. 21(18):4348-55 (1993).
Puga, A et al., "Aromatic hydrocarbon receptor interaction with the retinoblastoma protein potentiates repression of E2F-dependent transcription and cell cycle arrest" Journal Biological Chemistry, 275(4):2943-2950 (2000).
Pósfai, G. and Szybalski, W. "A simple method for locating methylated bases in DNA using class-IIS restriction enzymes," Gene, 74(1):179-181 (1988).

(56) References Cited

OTHER PUBLICATIONS

Qi, G.R. et al., "Restriction of single-stranded M13 DNA using synthetic oligonucleotides: the structural requirement of restriction enzymes," Biochem. Cell Biol. 65(1):50-55 (1986).
Rader, C and Barbas, C.F. 3rd, "Phage display of combinatorial antibody libraries" Curr. Opin. Biotechnol., 8(4):503-508 (1997).
Rajan, S. and Sidhu, S., "Simplified Synthetic Antibody Libraries" Methods in Enzymology 202 3-23 (2012).
Rakestraw, J.A. and Wittrup, K.D., "Dissertation Abstracts International", 68(1 B):43, abstract only (2006).
Rakestraw, J.A. et al., "A Flow Cytometric Assay for Screening Improved Heterologous Protein Secretion in Yeast." Biotechnol. Prog., 22(4):1200-1208 (2006).
Rauchenberger, R. et al., "Human combinatorial Fab library yielding specific and functional antibodies against the human fibroblast growth factor receptor 3" J. Biol. Chem., 278(40):38194-38205 (2003).
Raymond, C.K. et al., "General method for plasmid construction using homologous recombination" BioTechniques, 26(1):134-138, 140-141 (1999).
Real Party-in-interest, Filed in Interference No. 105,809, Filed May 20, 2011.
Redeclaration, Filed in Interference No. 105,809, Filed May 23, 2011.
Request for file copies, Filed in Interference No. 105,809, Filed May 20, 2011.
Retter, I. et al., "VBASE2, an integrative V gene database" Nucleic Acids Res., 33:D671-D674 (2005).
Rhoden, J.J. and Wittrup, K.D., "Dose Dependence of Intratumoral Perivascular Distribution of Monoclonal Antibodies" Journal of Pharmaceutical Sciences 101(2): 860-867 (2012).
Riske, F. et al., "The use of chitosan as a flocculant in mammalian cell culture dramatically improves clarification throughput without adversely impacting momoclonal antibody recovery" Journal of Biotechnology, 128:813-823 (2007).
Roitt, I. et al., "Immunoglobulins: A Family of Proteins", in Immunology, Sixth Edition, Mosby, Harcourt Publishers Limited, London, pp. 67-70 and 80 (2001).
Ruiz, M. et al., "The human immunoglobulin heavy diversity (IGHD) and joining (IGHJ) segments." Exp. Clin. lmrnunogenet, 16(3):173-184 (1999).
Ryu, D.D. and Nam, D.H., "Recent progress in biomolecular engineering" Biotechnol Prog, 16(1):2-16 (2000).
Saada, R. et al., "Models for antigen receptor gene rearrangement: CDR3 length" Immunol. Cell Biol., 85(4):323-332 (2007).
Saviranta, P. et al., "Engineering the steroid-specificity of an anti-17beta-estradiol Fab by random mutagenesis and competitive phage panning." Protein Engineering, 11(2):143-152 (1998).
Sblattero, D. and Bradbury, A., "A definitive set of oligonucleotide primers for amplifying human V regions" Immunotechnology, 3(4):271-278 (1998).
Sblattero, D. and Bradbury, A., "Exploiting recombination in single bacteria to make large phage antibody libraries" Nat. Biotechnol., 18(1):75-80 (2000).
Scaviner, D. et al., "Protein displays of the human immunoglobulin heavy, kappa and lambda variable and joining regions." Exp. Clin. Immunogenet., 16(4):234-240 (1999).
Schable, K.F. and Zachau, H.G., "The variable genes of the human immunoglobulin kappa locus" Biol. Chem. Hoppe Seyler, 374(11):1001-1022 (1993).
Schoonbroodt, S. et al., "Oligonucleotide-assisted cleavage and ligation: a novel directional DNA cloning technology to capture cDNAs. Application in the construction of a human immune antibody phage-display library" Nucleic Acids Research, 33(9):e81:2-14 (2005).
Seed, B., "Developments in expression cloning." Current Opinion in Biotechnology, 6(5):567-573 (1995).
Sheets, M.D. et al., "Efficient construction of a large nonimmune phage antibody library: The production of high-affinity human single-chain antibodies to protein antigens." Proc. Natl. Acad. Sci. USA, 95(11):6157-6162 (1998).
Shoji, H. et al., "Identification and characterization of a PDZ protein that interacts with activin type II receptors.", J.Biol. Chem., 275(8):5485-5492 (1999).
Short, M.K. et al., "Contribution of antibody heavy chain CDR1 to digoxin binding analyzed by random mutagenesis of phage-displayed Fab 26-10" J. Biol. Chem., 270(48):28541-28550 (1995).
Shusta, E.V. et al., "Directed evolution of a stable scaffold forT-cell receptor engineering" Nat. Biotechnol., 18(7):754-759 (2000).
Shusta, E.V. et al., "Yeast Polypeptide Fusion Surface Display Levels Predict Thermal Stability and Soluble Secretion Efficiency" J. Mol. Biol. 292 949-956 (1999).
Sidhu, S.S, et al., "Phage-displayed antibody libraries of synthetic heavy chain complementarity determining regions" J. Mol. Biol. 338(2):229-310 (2004).
Skerra, A., "Alternative non-antibody scaffolds for molecular recognition" Current Opin. Biotechnol. 18(4):295-304 (2007).
Smith, G.P. and Petrenko, V.A., "Phage Display" Chern. Rev., 97(2):391-410 (1997).
Soderlind, E. et al., "Domain libraries: synthetic diversity for de novo design of antibody V-regions" Gene, 160(2): 269-272 (1995).
Soderlind, E. et al., "The immune diversity in a test tube—nonimmunised antibody libraries and functional variability in defined protein scaffolds" Combinatorial Chemistry & High Throughput Screening, 4(5):409-416 (2001).
Souto-Carneiro, M.M. et al., "Characterization of the Hurnan Ig Heavy Chain Antigen Binding Complementarity Determining Region 3 Using a Newly Developed Software Algorithm, JOINSOLVER," J. Immunol., 172(11):6790-6802 (2004).
Standing Order, Filed in Interference No. 105,809, Filed May 6, 2011.
Stewart, A.K. et al., "High-frequency representation of a single VH gene in the expressed human B cell repertoire" J. Exp. Med., 177(2):409-418 (1993).
Stohl, W. and Hilbert, D.M., "The discovery and development of belimumab: The anti-BLyS-lupus connection" Nature Biology 30(1):69-77 (2012).
Suzuki, M. et al., "Light chain determines the binding property of human anti-dsDNA IgG autoantibodies" Biochem. Biophys. Res. Commun., 271(1):240-243 (2000).
Swers, J.S. et al., "Shuffled antibody libraries created by in vivo homologous recombination and yeast surface display" Nuc. Acids. Res. 32(3), e36, 1-8 (2004).
Szybalski W. and Skalka A., "Nobel prizes and restriction enzymes," Gene 4(3):181-182 (1978).
Szybalski W., "Reasons and risks to study restriction/modification enzymes form extreme thermophiles: chilly coldrooms, 13th sample, and 13-codon overlap" Gene, 112(1):1-2 (1992).
Szybalski W., "Universal restriction endonucleases: designing novel cleavage specificities by combining adaptor oligodeoxynucleotide and enzyme moieties" Gene, 40(2-3):169-173 (1985).
Szybalski, W. et al., "Class-IIS restriction enzymes—a review" Gene, 100:13-26 (1991).
Tavladoraki, P. et al., "Transgenic plants expressing a functional single-chain Fv antibody are specifically protected from virus attack" Nature, 366(6454):469-472 (1993).
Terret, N.K. (1998) "Combinational Chemistry", Oxford University Press, pp. 2-5.
Terskikh, A.V. et al., "Peptabody: A new type of high avidity binding protein" Proc. Natl. Acad., 94(5):1663-1668 (1997).
Thielking, V, et al., "Accuracy of the EcoRI restriction endonuclease: binding and cleavage studies with oligodeoxynucleotide substrates containing degenerate recognition sequences" Biochemistry, 29(19):4682-4691 (1990).
Tomlinson, I.M. et al., "The repertoire of human germline VH sequences reveals about fifty groups of VH segments with different hypervariable loops" Journal of Molecular Biology, 227(3):776-798 (1992).
Tomlinson, I.M. et al., "The structural repertoire of the human V kappa domain" EMBO J., 14(18):4628-4638 (1995).

(56) References Cited

OTHER PUBLICATIONS

Tsurushita, N. et al., "Phage display vectors for in vivo recombination of immunoglobulin heavy and light chain genes to make large combinatorial libraries" Gene, 172(1):59-63 (1996).
Ueda, M. and Tanaka, A., "Genetic immobilization of proteins on the yeast cell surface" Biotechnology Advances, 8(2):121-140 (2000).
Urlinger, S. et al., "Exploring the sequence space for tetracycline-dependent transcriptional activators: novel mutations yield expanded range and sensitivity" Proc. Natl. Acad. Sci. USA, 97(14):7963-7968 (2000).
Van Holten, R.W. and Autenrieth, S.M., "Evaluation of depth filtration to remove prion challenge from an immune globulin preparation" Vox Sanguinis 85:20-24 (2003).
Vander Vaart, J.M. et al., "Comparison of cell wall proteins of *Saccharomyces cerevisiae* as anchors for cell surface expression of heterologous proteins" Appl. Environ. Microbiol., 63(2):615-620 (1997).
Vaswani, S.K. and Hamilton, R.G., "Humanized antibodies as potential therapeutic drugs" Ann. Allergy Athma Immunol., 81(2):105-115 (1998).
Vendel, M.C. et al., "Secretion from bacterial versus mammalian cells yields a recombinant scFv with variable folding properties" Arch. Biochem. Biophys. 1-6 (2012).
Virnekas, B. et al., "Trinucleotide phosphoramidites: ideal reagents for the synthesis of mixed oligonucleotides for random mutagenesis" Nucleic Acids Res., 22(25):5600-5607 (1994).
Visintin. M. et al., "Selection of antibodies for intracellular function using a two-hybrid in vivo system.", Proc. Natl. Acad. Sci. USA 96(21):11723-11728 (1999).
Volpe, J.M. and Kepler, T.B., "Genetic correlates of autoreactivity and autoreactive potential in human Ig heavy chains" Immunome Res., 5:1 (2009).
Volpe, J.M. et al., "SoDA: Implementation of a 3D Alignment Algorithm for Inference of Antigen Receptor Recombinations," Bioinforrnatics, 22(4):438-444 (2006).
Vugmeyster Y., "Biodistribution of [125I]-Labeled Therapeutic Proteins: Application in Protein Drug Development Beyond Oncology" Journal of Pharmaceutical Sciences 99(2) 1028-1045 (2010).
Vugmeyster, Y. et al., "Complex Pharmacokinetics of a Humanized Antibody Against Human Amyloid Beta Peptide, Anti-Abeta Ab2, in Nonclinical Species" Pharm Res, 28:1696-1706 (2011).
Walhout, A.J. et al., "GATEWAY recombinational cloning: application to the cloning of large numbers of open reading frames or ORFeomes" Methods in Enzymology, 328:575-92 (2000).
Wang, Y. et al., "Many human immunoglobulin heavy-chain IGHV gene polymorphisms have been reported in error" Immunol. Cell. Biol., 86(2):111-115 (epub 2007-2008).
Weaver-Feldhaus, J.M. et al., "Yeast mating for combinatorial Fab library generation and surface display" FEBS Lett., 564(1-2):24-34 (2004).
Wentz, A.E. and Shusta, E.V., "A novel high-throughput screen reveals yeast genes that increase secretion of heterologous proteins" Appl. Environ. Microbiol., 73(4):1189-1198 (2007).
Winter G. and Milstein C., "Man-made antibodies" Nature, 349(6307):293-299 (1991).
Wörn, A. and Plückthun, A., "An intrinsically stable antibody scFv fragment can tolerate the loss of both disulfide bonds and fold correctly." FEBS Lett., 427(3):357-361 (1998).
Xu, J.L. and Davis, M.M., "Diversity in the CDR3 region of V(H) is sufficient for most antibody specificities" Immunity, 13(1):37-45 (2000).
Yang, W.P. et al., "CDR walking mutagenesis for the affinity maturation of a potent human anti-HIV-1 antibody into the picomolar range" J. Molecular Biology, 254(3):392-403 (1995).
Zemlin, M. et al., "Expressed murine and human CDR-H3 intervals of equal length exhibit distinct repertoires that differ in their amino acid composition and predicted range of structures" J. Mol. Biol. 334(4):733-749 (2003).
Zeng, Q. et al., "CD146, an epithelial-mesenchymal transition inducer, is associated with triple-negative breast cancer" PNAS Early Edition 1-6.
Zhu D.L., "Oligodeoxynucleotide-directed cleavage and repair of a single-stranded vector: a method of site-specific mutagenesis" Analytical Biochemistry, 177(1):120-124 (1989).
Zucconi, A. et al., "Domain repertoires as a tool to derive protein recognition rules" FEBS Letters, 480(1):49-54 (2000).
Bahler et al., "Clonal Salivary Gland Infiltrates Assciated with Myoepithelial Sialadenitis (Sjögren's Syndrome) Begin as Nonmalignant Antigen-Selected Expansions", Blood, 91(6):1864-1872 (1998).
Bakkus et al., "Evidence that Multiple Myeloma Ig Heavy Chain VDJ Genes Contain Somatic Mutations but Show no Intraclonal Variation", Blood, 80(9):2326-2335 (1992).
Barbas et al., "Molecular Profile of an Antibody Response to HIV-1 as Probed by Combinatorial Libraries", J. Mol. Biol., 230:812-823 (1993).
Bengten, E. et al., Channel Catfish Immunoglobulins: Repertoire and Expression, Dev. Camp. Immunol., 30:77-92 (2006).
Bruggemann, M. et al., Immunoglobulin Heavy Chain Locus of the Rat: Striking Homology to Mouse Antibody Genes, Proc. Natl. Acad. Sci. USA, 83:6075-6079 (1986).
Butler, J.E. et al., Antibody Repertoire Development in Swine, Dev. Camp. Immunol., 30:199-221 (2006).
Carroll et al., "Absence of Ig V Region Gene Somatic Hypermutation in Advanced Burkitt's Lymphoma", J. Immunol., 143(2):692-698 (1989).
Das, S. et al., Evolutionary Dynamics of the Immunoglobulin Heavy Chain Variable Region Genes in Vertebrates, NIH Public Access Author Manuscript from Immunogenetics, 60(1 ):47-55 (2008).
Davi et al., "High Frequency of Somatic Mutations in the VH Genes Expressed in Prolymphocytic Leukemia", Blood, 88(10):3953-3961 (1996).
De Genst, E. et al., Antibody Repertoire Development in Camelids, Dev. Camp. Immunol., 30:187-198 (2006).
Decision—Dyax Response to Order to Show Cause—Bd.R. 41.125(c) in Patent Interference No. 105,809, Dec. 30, 2013.
Decision on Motions in Patent Interference No. 105,809, Nov. 2, 2012.
DiPietro et al., Limited number of immunoglobulin VH regions expressed in the mutant rabbit 'Alicia', Eur. J. Immunol., 20:1401-1404 (1990).
Dirkes, G. et al., Sequence and Structure of the Mouse IgH DQ52 5' Region, Immunogenetics, 40:379 (1994).
Dooley, H. et al., Antibody Repertoire Development in Cartilaginous Fish, Dev. Camp. Immunol., 30:43-56 (2006).
Esposito et al., "Phage display of a human antibody against Clostridium tetani toxin", Gene, 148:167-168 (1994).
Friedman, M. L. et al., Neonatal VH, D, and JH, Gene Usage in Rabbit B Lineage Cells, Immunol., 152:632-641 (1994).
Gerondakis, S. et al., Immunoglobulin JH Rearrangement in aT-cell Line Reflects Fusion to the DH Locus at a Sequence Lacking the Nonamer Recognition Signal, Immunogenetics, 28:255-259 (1998).
Ghaffari, S.H. et al., Structure and Genomic Organization of a Second Cluster of Immunoglobulin Heavy Chain Gene Segments in the Channel Catfish, J. Immunol., 162:1519-1529 (1999).
Gu, H. et al., B Cell Development Regulated by Gene Rearrangement: Arrest of Maturation by Membrane-Bound D11 Protein and Selection of DH Element Reading Frames, Cell, 65:47-54 (1991 ).
Hayman, J. R. et al., Heavy Chain Diversity Region Segments of the Channel Catfish: Structure, Organization, Expression and Phylogenetic Implications, J. Immunol, 164:1916-1924 (2000).
Hoogenboom et al., "By-passing Immunisation Human Antibodies from Synthetic Repertoires of Germline VH Gene Segments Rearranged in Vitro", J. Mol. Biol., 227:381-388 (1992).
Huang et al., "A Majority of Ig H Chain cDNA of Normal Human Adult Blood Lymphocytes Resembles cDNA for Fetal Ig and Natural Autoantibodies", J. Immunol., 151:5290-5300 (1993).
Ivanovski et al., "Somatic Hypermutation, Clonal Diversity, and Preferential Expression of the VH 51p/VL kv325 Immunoglobin

(56) References Cited

OTHER PUBLICATIONS

Gene Combination in Hepatitis C Virus-Associated Immunocytomas", Blood, 91(7):2433-2442 (1998).
Jenne, C. N. et al., Antibody Repertoire Development in the Sheep, Dev. Camp. Immunol., 30:165-174 (2006).
Judgment—Bd.R. 127 in Patent Interference No. 105,809, Dec. 30, 2013.
Kurosawa, Y. et al., Identification of D Segments of Immunoglobulin Heavy-Chain Genes and Their Rearrangement in T Lymphocytes, Nature, 290:565-570 (1981).
Letter from Michael T. Siekman to Brenda H. Jarrell, dated Nov. 13, 2012.
Lieber et al., "Lymphoid V(D)J recombination: Nucleotide insertion at signal joints as well as coding joints", Proc. Natl. Acad. Sci. USA, 85:8588-8592 (1988).
Lieber, M.R., "Site-specific recombination in the immune system", FASEB J., 5:2934-2944 (1991) Liu et al., "Normal Human IgD+IgM− Germinal Center B Cells can Express up to 80 Mutations in the Variable Region of their IgD Transcripts", Immunity, 4:603-613 (1996).
Link, J. M. et al., The Rhesus Monkey Immunoglobulin /GHD Germline Repertoire, Immunogenetics, 54:240-250 (2002).
Liu et al., "Normal Human IgD+IgM− Germinal Center B Cells can Express up to 80 Mutations in the Variable Region of their IgD Transcripts", Immunity, 4:603-613 (1996).
Lundqvist, M. L. et al., Immunoglobulins of the Non-Galliform Birds: Antibody Expression and Repertoire in the Duck, Dev. Camp. Immunol., 30:93-100 (2006).
Mage, R. G. et al., B Cell and Anitbody Repertoire Development in Rabbits: The Requirement of Gut-Associated Lymphoid Tissues, Dev. Camp. Immunol., 30:137-153 (2006).
Malecek, K. et al., Somatic Hypermutation and Junctional Diversification at Ig Heavy Chain Loci in the Nurse Shark, J. Immunol., 175:81 05-8115 (2005).
Matolcsy et al., "Molecular Characterization of IgA− and/or IgG-Switched Chronic Lymphocytic Leukemia B Cells", Blood, 89(5):1732-1739 (1997).
McCafferty et al., "Phage antibodies: filamentous phage displaying antibody variable domains", Nature, 348:552-554 (1990).
McIntosh et al., "Analysis of Immunoglobulin Gk Antithyroid Peroxidase Antibodies from Different Tissues in Hashimoto's Thyroiditis", J. Clin. Endocrinol. Metab., 82(11):3818-3825 (1997).
Mouquet et al., "Enhanced HIV-1 neutralization by antibody heteroligation", PNAS, published on line before printing, Jan. 4, 2012, doi:10.1073/pnas.1120059109.
Nguyen, V. K. et al., Camel Heavy-Chain Antibodies: Diverse Germline VHH and Specific Mechanisms Enlarge the Antigen-binding Repertoire, EMBO J, 19:(5)921-930 (2000).
Nissim et al., "Antibody fragments from a 'single pot' phage display library as immunochemical reagents", The EMBO Journal, 13(3):692-698 (1994).
Osbourn, J.K., et al., Directed selection of MIP-1 alpha neutralizing CCR5 antibodies from phage display human antibody library, Nat. Biotech. 16:778-781 (1998).
Ratcliffe, M.J.H. et al., Antibodies, Immunoglobulin Genes and the Bursa of Fabricius in Chicken B Cell Development, Dev. Comp. Immunol., 30:101-118 (2006).
Sahota et al., "Ig VH Gene Mutational Patterns Indicate Different Tumor Cell Status in Human Myeloma and Monoclonal Gammopathy of Undetermined Significance", Blood, 87(2):746-755 (1996).
Shimizu, T. et al., Biased Reading Frames on Pre-Existing DH—JH Coding Joints and Preferential Nucleotide Insertions at VH—DJH Signal Joints of Excision Products of Immunoglobulin Heavy Chain Gene Rearrangements, EMBO J., 11 :(13)4869-4875 (1992).
Shimoda et al., "Natural polyreactive immunoglobulin A antibodies produced in mouse Peyer's patches", Immunology, 97:9-17 (1999).
Shojaei, F. et al., Unusually Long Germline DH Genes Contribute to Large Sized CDR3H in Bovine Antibodies, Mol. Immunol., 40:61-67 (2003).

Solem, S.T. et al., Antibody Repertoire Development in Teleosts—A Review with Emphasis on Salmonids and Gadus morhua L, Dev. Camp. Immunol., 30:57-76 (2006).
Wagner, B., Immunoglobulins and Immunoglobulin Genes of the Horse, Dev. Camp. Immunol., 30:155-164 (2006).
Welschof et al., "Amino acid sequence based PCR primers for amplification of rearranced human heavy and light chain immunoglobulin variable region genes", J. Immunol. Meth., 179:203-214 (1995).
Wen et al., "T cells recognize the VH complementarity-determining region 3 of the idiotypic protein of B cell non-Hodgkin's lymphoma", Eur. J. Immunol., 27:1043-1047 (1997).
Winkler et al., "Analysis of immunoglobulin variable region genes from human IgG anti-DNA hybridomas", Eur. J. Immunol., 22:1719-1728 (1992).
Winter, Greg, "Synthetic human antibodies and a strategy for protein engineering", FEBS Letters, 430:92-94 (1998).
Xu et al., "Diversity in the CDR3 Region of VH is Sufficient for Most Antibody Specificities", Immunity, 13:37-45 (2000).
Ye, J., The Immunoglobulin /GHD Gene Locus in C57BL/6 Mice, Immunogenetics, 56:399-404 (2004).
Zeng et al., "CD146, an epithelial-mesenchymal transition inducer, is associated with triple-negative breast cancer", published on line before print Dec. 30, 2011, doi:1010.1073/pnas.1111053108.
Zhang, Y., et al., Selection of active scFv to G-protein-coupled receptor CCR5 using surface antigen-mimicking peptides, Biochem. 43:12575-12584 (2004).
Zhao, Y. et al., The Bovine Antibody Repertoire, Dev. Camp. Immunol., 30:175-186 (2006).
Conzelmann, A. et al., Myoinositol gets incorporated into numerous membrane glycoproteins of *Saccharomyces cerevisiae*; incorporation is dependent on phosphomannomutase (sec53), EMBO Journal, 9(3):653-661 (1990).
Duffy, S. et al., Site-Specific, Enzymatic Biotinylation of Recombinant Proteins in Spodoptera frugiperda Cells Using Biotin Acceptor Peptides, Analytical Biochemistry, 262:122-128 (1998).
Frieman, M. and Cormack, BP, Multiple sequence signals determine the distribution of glycosylphosphatidylinositol proteins between the plasma membrane and cell wall in *Saccharamyces cerevisiae*, Microbiology, 150(Pt 10):3105-3114 (2004).
Futcher, AB and Cox, BS, Maintenance of the 2 microns circle plasmid in populations of *Saccharomyces cerevisiae*, Journal of Bacteriology, 154(2):612-622 (1983).
Griffin, TJ., et al., Complementary profiling of gene expression at the transcriptome and proteome levels in *Saccharomyces cerevisiae*, Molecular & Cellular Proteomics, 1(4):323-333 (2002).
Hamada, K. et al., Amino acid sequence requirement for efficient incorporation of glycosylphosphatidylinositol-associated proteins into the cell wall of *Saccharomyces cerevisiae*, Journal of Biological Chemistry, 273(41):26946-26953 (1998).
Holliger, P. and Hudson, PJ, Engineered antibody fragments and the rise of single domains, Nature Biotechnology, 23(9):1126-1136 (2005).
Hollinger, P. et al., "Diabodies": small bivalent and bispecific antibody fragments, Proceedings of the National Academy of Science USA, 90(14):6444-6448 (1993).
Jayaram, M. et al., The yeast plasmid 2mu circle enclodes components required for its high copy propagation, Cell, 34(1):95-104 (1983).
Jones, PT. et al., Replacing the complementarity-determining regions in a human antibody with those from a mouse, Nature, 321(6069):522-525 (1986).
Kabat, E. et al., Sequences of Proteins of Immunological Interest, 5th Edition, Public Health Service, National Institutes of Health, Bethesda, MD, 647-669 (1991).
Kaufman, Randal J., Selection and Coamplification of Heterologous Genes in Mammalian Cells, Methods in Enzymology, 185:537-566 (1991).
Kaufman, Randal J., Vectors Used for Expression in Mammalian Cells, Methods in Enzymology, 185:487-511 (1991).
Keown, WA et al., Methods for introducing DNA into mammalian cells, Methods in Enzymology, 185:527-537 (1990).

(56) References Cited

OTHER PUBLICATIONS

Kohler, G. and Milstein, C., Continuous cultures of fused cells secreting antibody of predefined specificity, Nature, 256(5517):495-497 (1975).

Kok, J., Genetics of the proteolytic system of lactic acid bacteria, FEMS Microbiology Reviews, 7(1-2):15-42 (1990).

Lewin, Roger, The universal constructor set, New Scientist, 1746:30-33 (1990).

Murray, JA et al., Antagonistic controls regulate copy number of the yeast 2 mu plasmid, EMBO Journal, 6(13):4205-4212 (1987).

Muyldermans, S. et al., Sequence and structure of VH domain from naturally occurring camel heavy chain immunoglobulins lacking light chains, Protein Engineering, 7(9):1129-1135 (1994).

Pluckthun, A., Antibodies from *Escherichia coli*, The Pharmacology of Monoclona Antibodies, 113:268-315 (1994).

Presta, Leonard G., Antibody engineering, Current Opinion in Biotechnology, 3:395-3999 (1992).

Riechmann, L. et al., Reshaping human antibodies for therapy, Nature, 332:323-327 (1988).

Silverman, J. et al., Multivalent avimer proteins evolved by exon shuffling of a family of human receptor domains, Nature Biotechnology, 23(12):1556-1561 (2005).

Struhl, K. et al., High-frequency transformation of yeast: autonomous replication of hybrid DNA molecules, Proceedings of the National Academy of Science USA, 76(3):1035-1039 (1979).

Ward, ES. et al., Binding activities of a repertoire of single immunoglobulin variable domains secreted from *Escherichia coli*, Nature, 341(6242):544-546 (1989).

Boder, E. and Wittrup, K., Yeast Surface Display for Directed Evolution of Protein Expression, Affinity, and Stability, Methods In Enzymology, 328:430-444 (2000).

Boder, E. and Wittrup, K., Yeast Surface Display for Directed Evolution of Protein Expression, Affinity, and Stability, Methods In Enzymology, Abstract Only (2000).

Rakestraw, A. and Wittrup, K., Contrasting Secretory Processing of Simultaneously Expressed Heterologous Proteins in *Saccharomyces cerevisiae*, Biotechnology and Bioengineering, 93(5):895-905 (2006).

\* cited by examiner

Figure 1 CDRs in the variable regions of a non-human antibody
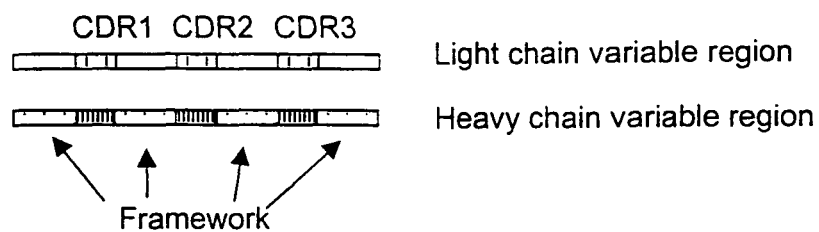
Figure 2 Graft of non-human CDRs into a human antibody framework
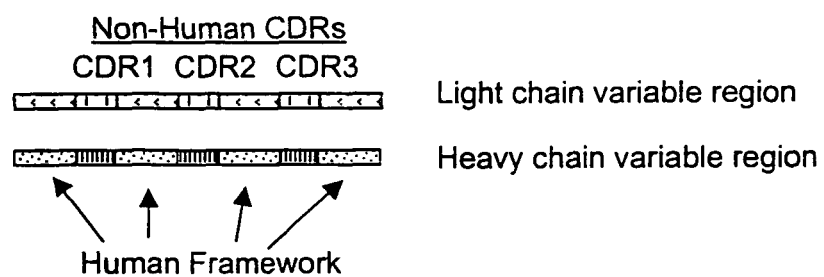

FIGURE 3

Sequence of DP47 [SEQ ID NO: 1]

GAGGTGCAGCTGTTGGAGTCTGGGGGAGGCTTGGTACAGCCTGGGGGGTCCCTGAGACT
CTCCTGTGCAGCCTCTGGATTCACCTTTAGCAGCTATGCCATGAGCTGGGTCCGCCAGG
CTCCAGGGAAGGGGCTGGAGTGGGTCTCAGCTATTAGTGGTAGTGGTGGTAGCACATAC
TACGCAGACTCCGTGAAGGGCCGGTTCACCATCTCCAGAGACAATTCCAAGAACACGCT
GTATCTGCAAATGAACAGCCTGAGAGCCGAGGACACGGCCGTATATTACTGTGCAAAG
A

Sequence of DPK22 [SEQ ID NO: 2]

GAAATTGTGTTGACGCAGTCTCCAGGCACCCTGTCTTTGTCTCCAGGGGAAAGAGCCAC
CCTCTCCTGCAGGGCCAGTCAGAGTGTTAGCAGCAGCTACTTAGCCTGGTACCAGCAGA
AACCTGGCCAGGCTCCCAGGCTCCTCATCTATGGTGCATCCAGCAGGGCCACTGGCATC
CCAGACAGGTTCAGTGGCAGTGGGTCTGGGACAGACTTCACTCTCACCATCAGCAGACT
GGAGCCTGAAGATTTTGCAGTGTATTACTGTCAGCAGTATGGTAGCTCACCTCC

FIGURE 4

A. Variable Regions of Mouse Monoclonal Anti-IL-8 Antibody (Murine IL-8 Ab)

Murine V_H DNA Sequence [SEQ ID NO:4]:

CAGGTCCAGTTGCAGCAGTCTGGAGCTGAGTCGGTAAGGCCTGGGACTTCAGTGAAGATATCCTGC
AAGGCTTCTGGCTACACCTTCACTAACTACTGGCTAGGTTGGGTAAAGCAGAGGCCTGGACATGGA
CTTGAGTGGATTGGAGATATTTACCCTGGAGGTGGTTATACTAACTACAATGAGAAGTTCAAGGAC
AAGGCCACACTGACAACAGACACATCCTCCAGCACTGCCTACATGCAGCTCAGTAGCCTGACATCT
GATGACTCTGCTGTCTATTTCTGTGCAAGGGACTACGGTAGTAGGTACTACTTTGACTACTGGGGC
CAAGGCACCACTCTCACAGTCTCCTCA

Murine V_H Amino Acid Sequence [SEQ ID NO:5]:

QVQLQQSGAESVRPGTSVKISCKASGYTFTNYWLGWVKQRPGHGLEWIGDIYPGGGYTNYNEKFKDKATLT
TDTSSSTAYMQLSSLTSDDSAVYFCARDYGSRYYFDYWGQGTTLTVSS

Murine V_L DNA Sequence [SEQ ID NO:6]:

GATATCCAGATGACACAGACTACATCCTCCCTGTCTGCCTCTCTGGGAGACAGAGTCACCATCAGTT
GCAGGGCAAGTCAGGACATTAGCAATTTTTTAAACTGGTATCAGCAGAAACCAGATGGAACTGTTAA
ACTCCTGATCTACTACACATCAAGATTACACTCAGGAGTCCCATCAAGGTTCAGTGGCAGTGGGTCT
GGAACAGATTATTCTCTCACCATTAGCAACCTGGAACAAGAAGATATTGCCACTTACTTTTGCCAAC
AGGGTAACACGCTGTGGACGTTCGGTGGAGGCACCAAGCTGGAAATCAAACGG

Murine V_L Amino Acid Sequence [SEQ ID NO:7]:
DIQMTQTTSSLSASLGDRVTISCRASQDISNFLNWYQQKPDGTVKLLIYYTSRLHSGVPSRFSGSGSGTDY
SLTISNLEQEDIATYFCQQGNTLWTFGGGTKLEIKR

B. Variable Regions of Human Antibodies That are Highly Homologous to Murine IL-8 Ab Human V_H Amino Acid Sequence of Human antibody Kabat Entry No: 037656
[SEQ ID NO:8]:
QVQLLESGAELVRPGASVKISCKASGYAFSSSWMNWVKQRPGQGLEWIGRIYPGDGDTNYNGKFKEAATLT
ADKSSSTAYMQLSSLTSVDSAVYSCARSEYWGNYWAMDYWGQGTTVT Human V_L Amino Acid Sequence of Human antibody Kabat Entry No: 039682
[SEQ ID NO:9]:
DIQMTQSPSSLSASVGDRVTITCRASQSISSYLNWYQQKPGKAPKLLIYAASSLQSGVPSRFSGSGSGTDF
TLTISSLQPEDFATYYCQQSYSTLTFGGGTKVEIKR Figure 5A Alignment of V$_H$ of Murine IL-8 Ab (HB-9647) and V$_H$ of a Human Antibody (Kabat Entry No: 037656)

| # | Hu | Mu | # | Hu | Mu | # | Hu | Mu |
|---|----|----|---|----|----|---|----|----|
| 1 | GLN | GLN | 46 | GLU | GLU | 87 | SER | SER |
| 2 | VAL | VAL | 47 | TRP | TRP | 88 | ALA | ALA |
| 3 | GLN | GLN | 48 | ILE | ILE | 89 | VAL | VAL |
| 4 | LEU | LEU | 49 | GLY | GLY | 90 | TYR | TYR |
| 5 | LEU | gln | 50 | ARG | asp | 91 | SER | phe |
| 6 | GLU | gln | 51 | ILE | ILE | 92 | CYS | CYS |
| 7 | SER | SER | 52 | TYR | TYR | 93 | ALA | ALA |
| 8 | GLY | GLY | 52A | PRO | PRO | 94 | ARG | ARG |
| 9 | ALA | ALA | 52B | --- | --- | 95 | SER | asp |
| 10 | GLU | GLU | 52C | --- | --- | 96 | GLU | tyr |
| 11 | LEU | ser | 53 | GLY | GLY | 97 | TYR | gly |
| 12 | VAL | VAL | 54 | ASP | gly | 98 | TRP | ser |
| 13 | ARG | ARG | 55 | GLY | GLY | 99 | GLY | arg |
| 14 | PRO | PRO | 56 | ASP | tyr | 100 | ASN | tyr |
| 15 | GLY | GLY | 57 | THR | THR | 100A | TYR | TYR |
| 16 | ALA | thr | 58 | ASN | ASN | 100B | TRP | phe |
| 17 | SER | SER | 59 | TYR | TYR | 100C | ALA | --- |
| 18 | VAL | VAL | 60 | ASN | ASN | 100D | MET | --- |
| 19 | LYS | LYS | 61 | GLY | glu | 100E | --- | --- |
| 20 | ILE | ILE | 62 | LYS | LYS | 100F | --- | --- |
| 21 | SER | SER | 63 | PHE | PHE | 100G | --- | --- |
| 22 | CYS | CYS | 64 | LYS | LYS | 100H | --- | --- |
| 23 | LYS | LYS | 65 | GLU | asp | 100I | --- | --- |
| 24 | ALA | ALA | 66 | ALA | lys | 100J | --- | --- |
| 25 | SER | SER | 67 | ALA | ALA | 100K | --- | --- |
| 26 | GLY | GLY | 68 | THR | THR | 101 | ASP | ASP |
| 27 | TYR | TYR | 69 | LEU | LEU | 102 | TYR | TYR |
| 28 | ALA | thr | 70 | THR | THR | 103 | TRP | TRP |
| 29 | PHE | PHE | 71 | ALA | thr | 104 | GLY | GlY |
| 30 | SER | thr | 72 | ASP | ASP | 105 | GLN | GLN |
| 31 | SER | asn | 73 | LYS | thr | 106 | GLY | GLY |
| 32 | SER | tyr | 74 | SER | SER | 107 | THR | THR |
| 33 | TRP | TRP | 75 | SER | SER | 108 | THR | THR |
| 34 | MET | leu | 76 | SER | SER | 109 | VAL | leu |
| 35 | ASN | gly | 77 | THR | THR | 110 | THR | THR |
| 35A | --- | --- | 78 | ALA | ALA | 111 | | val |
| 35B | --- | --- | 79 | TYR | TYR | 112 | | ser |
| 36 | TRP | TRP | 80 | MET | MET | 113 | | ser |
| 37 | VAL | VAL | 81 | GLN | GLN | | | |
| 38 | LYS | LYS | 82 | LEU | LEU | | | |
| 39 | GLN | GLN | 82A | SER | SER | | | |
| 40 | ARG | ARG | 82B | SER | SER | | | |
| 41 | PRO | PRO | 82C | LEU | LEU | | | |
| 42 | GLY | GLY | 83 | THR | THR | | | |
| 43 | GLN | his | 84 | SER | SER | | | |
| 44 | GLY | GLY | 85 | VAL | asp | | | |
| 45 | LEU | LEU | 86 | ASP | ASP | | | |

☐ Kabat CDRs

Chothia CDRs

Figure 5B Alignment of $V_L$ of Murine IL-8 Ab (HB-9647) and $V_L$ of a Human Antibody (Kabat Entry No: 039682)

| # | Hu | Mu | # | Hu | Mu | # | Hu | Mu |
|---|---|---|---|---|---|---|---|---|
| 1 | ASP | ASP | 40 | PRO | PRO | 85 | THR | THR |
| 2 | ILE | ILE | 41 | GLY | asp | 86 | TYR | TYR |
| 3 | GLN | GLN | 42 | LYS | gly | 87 | TYR | phe |
| 4 | MET | MET | 43 | ALA | thr | 88 | CYS | CYS |
| 5 | THR | THR | 44 | PRO | val | 89 | GLN | GLN |
| 6 | GLN | GLN | 45 | LYS | LYS | 90 | GLN | GLN |
| 7 | SER | thr | 46 | LEU | LEU | 91 | SER | gly |
| 8 | PRO | thr | 47 | LEU | LEU | 92 | TYR | asn |
| 9 | SER | SER | 48 | ILE | ILE | 93 | SER | thr |
| 10 | SER | SER | 49 | TYR | TYR | 94 | THR | leu |
| 11 | LEU | LEU | 50 | ALA | tyr | 95 | LEU | trp |
| 12 | SER | SER | 51 | ALA | thr | 95A | --- | --- |
| 13 | ALA | ALA | 52 | SER | SER | 95B | --- | --- |
| 14 | SER | SER | 53 | SER | arg | 95C | --- | --- |
| 15 | VAL | leu | 54 | LEU | LEU | 95D | --- | --- |
| 16 | GLY | GLY | 55 | GLN | his | 95E | --- | --- |
| 17 | ASP | ASP | 56 | SER | SER | 95F | --- | --- |
| 18 | ARG | ARG | 57 | GLY | GLY | 96 | --- | --- |
| 19 | VAL | VAL | 58 | VAL | VAL | 97 | THR | THR |
| 20 | THR | THR | 59 | PRO | PRO | 98 | PHE | PHE |
| 21 | ILE | ILE | 60 | SER | SER | 99 | GLY | GLY |
| 22 | THR | ser | 61 | ARG | ARG | 100 | GLY | GLY |
| 23 | CYS | CYS | 62 | PHE | PHE | 101 | GLY | GLY |
| 24 | ARG | ARG | 63 | SER | SER | 102 | THR | THR |
| 25 | ALA | ALA | 64 | GLY | GLY | 103 | LYS | LYS |
| 26 | SER | SER | 65 | SER | SER | 104 | VAL | leu |
| 27 | GLN | GLN | 66 | GLY | GLY | 105 | GLU | GLU |
| 27A | --- | --- | 67 | SER | SER | 106 | ILE | ILE |
| 27B | --- | --- | 68 | GLY | GLY | 106A | --- | --- |
| 27C | --- | --- | 69 | THR | THR | 107 | LYS | LYS |
| 27D | --- | --- | 70 | ASP | ASP | 108 | ARG | ARG |
| 27E | --- | --- | 71 | PHE | tyr | | | |
| 27F | --- | --- | 72 | THR | ser | | | |
| 28 | SER | asp | 73 | LEU | LEU | | | |
| 29 | ILE | ILE | 74 | THR | THR | | | |
| 30 | SER | SER | 75 | ILE | ILE | | | |
| 31 | SER | asn | 76 | SER | SER | | | |
| 32 | TYR | phe | 77 | SER | asn | | | |
| 33 | LEU | LEU | 78 | LEU | LEU | | | |
| 34 | ASN | ASN | 79 | GLN | glu | | | |
| 35 | TRP | TRP | 80 | PRO | gln | | | |
| 36 | TYR | TYR | 81 | GLU | GLU | | | |
| 37 | GLN | GLN | 82 | ASP | ASP | | | |
| 38 | GLN | GLN | 83 | PHE | ile | | | |
| 39 | LYS | LYS | 84 | ALA | ALA | | | |

☐ Kabat CDRs

Chothia CDRs

Figure 6 Cloning process for humanization of Ab by two-hybrid method
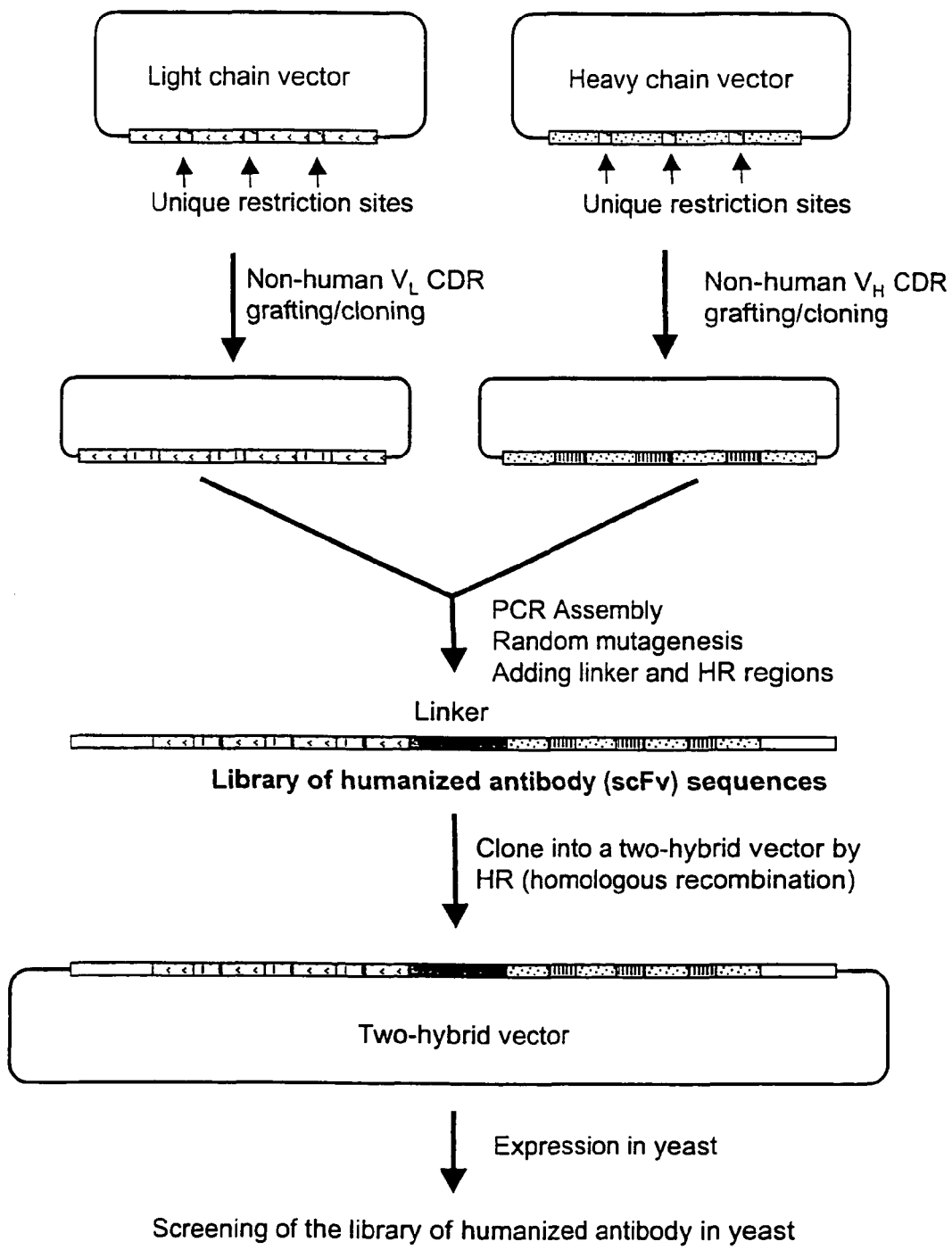

Figure 7 Humanization of antibody retaining non-human CDR3
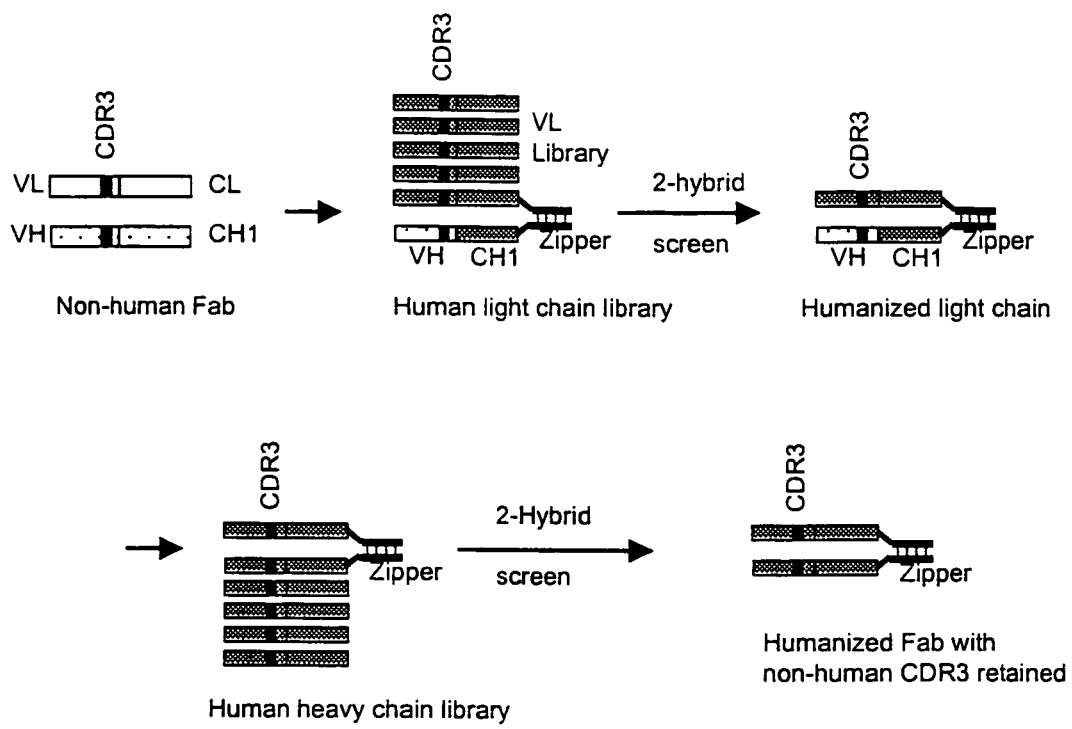

Figure 8 Humanization by double chain Fab approach
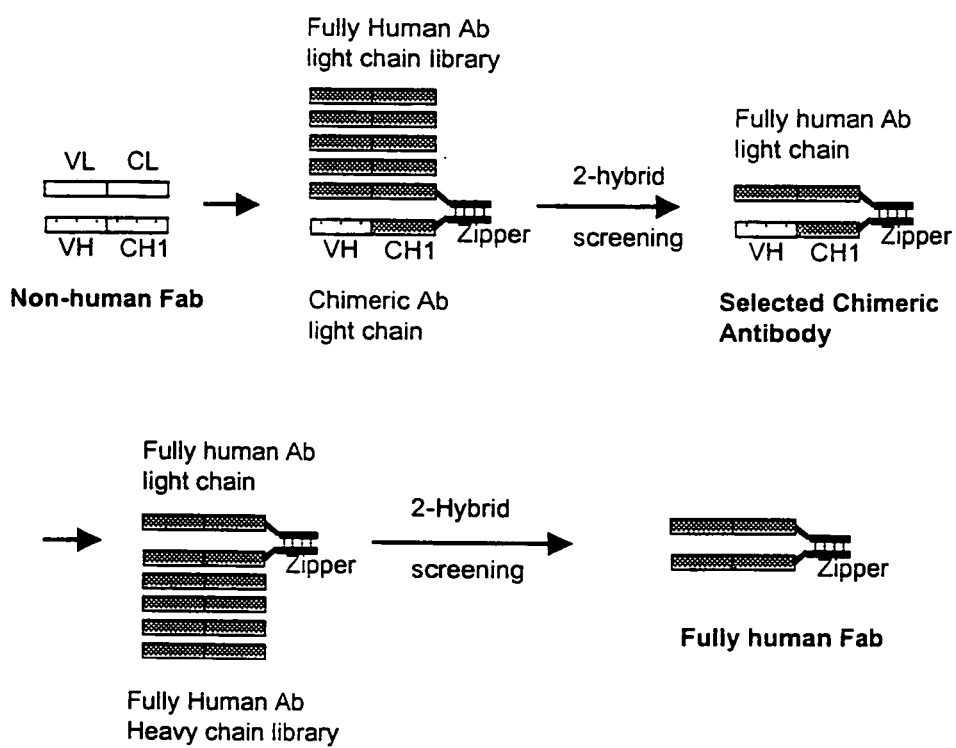

Figure 11 Selection of Humanized Antibody Through Ribosome Display

Figure 12 Selection of Humanized Antibody Through mRNA Display

Screening in yeast by mating and isolating high affinity clones

HIGH THROUGHPUT GENERATION AND AFFINITY MATURATION OF HUMANIZED ANTIBODY

CROSS-REFERENCE

This application is a continuation application of Ser. No. 10/460,595, filed Jun. 11, 2003, now abandoned which claims the priority benefit of U.S. Provisional Application No. 60/403,296 filed Aug. 12, 2002, which are incorporated herein by reference in their entirety and to which applications we claim priority under 35 USC §120.

FIELD OF THE INVENTION

This invention relates to compositions, methods and kits for generating libraries of humanized antibodies for the screening of antibody with high affinity toward specific target antigens and reduced immunogenicity in human, and, more particularly, for generation and affinity maturation of the humanized antibody in a high throughput and automated manner. DESCRIPTION OF RELATED ART Antibodies are a diverse class of molecules. Delves, P. J. (1997) "Antibody production: essential techniques", New York, John Wiley & Sons, pp. 90-113. It is estimated that even in the absence of antigen stimulation a human makes at least 1015 different antibody molecules—its Permian antibody repertoire. The antigen-binding sites of many antibodies can cross-react with a variety of related but different antigenic determinants, and the Permian repertoire is apparently large enough to ensure that there will be an antigen-binding site to fit almost any potential antigenic determinant, albeit with low affinity.

Structurally, antibodies or immunoglobulins (Igs) are composed of one or more Y-shaped units. For example, immunoglobulin G (IgG) has a molecular weight of 150 kDa and consists of just one of these units. Typically, an antibody can be proteolytically cleaved by the proteinase papain into two identical Fab (fragment antigen binding) fragments and one Fc (fragment crystallizable) fragment. Each Fab contains one binding site for antigen, and the Fc portion of the antibodies mediates other aspects of the immune response.

A typical antibody contains four polypeptides-two identical copies of a heavy (H) chain and two copies of a light (L) chain, forming a general formula $H_2L_2$. Each L chain is attached to one H chain by a disulfide bond. The two H chains are also attached to each other by disulfide bonds. Papain cleaves N-terminal to the disulfide bonds that hold the H chains together. Each of the resulting Fabs consists of an entire L chain plus the N-terminal half of an H chain; the Fc is composed of the C-terminal halves of two H chains. Pepsin cleaves at numerous sites C-terminal to the inter-H disulfide bonds, resulting in the formation of a divalent fragment [F(ab')] and many small fragments of the Fc portion. IgG heavy chains contain one N-terminal variable ($V_H$) plus three C-terminal constant ($C_H1$, $C_H2$ and $C_H3$) regions. Light chains contain one N-terminal variable ($V_L$) and one C-terminal constant ($C_L$) region each. The different variable and constant regions of either heavy or light chains are of roughly equal length (about 110 amino residues per region). Fabs consist of one $V_L$, $V_H$, $C_H1$, and $C_L$ region each. The $V_L$ and $V_H$ portions contain hypervariable segments (complementarity-determining regions or CDR) that form the antibody combining site.

The $V_L$ and $V_H$ portions of a monoclonal antibody have also been linked by a synthetic linker to form a single chain protein (scFv) which retains the same specificity and affinity for the antigen as the monoclonal antibody itself Bird, R. E., et al. (1988) "Single-chain antigen-binding proteins" Science 242:423-426. A typical scFv is a recombinant polypeptide composed of a $V_L$ tethered to a $V_H$ by a designed peptide, such as $(Gly_4\text{-}Ser)_3$, that links the carboxyl terminus of the VL to the amino terminus of the VH sequence. The construction of the DNA sequence encoding a scFv can be achieved by using a universal primer encoding the $(Gly_4\text{-}Ser)_3$ linker by polymerase chain reactions (PCR). Lake, D. F., et al. (1995) "Generation of diverse single-chain proteins using a universal (Gly4-Ser)3 encoding oligonucleotide" Biotechniques 19:700-702.

The mammalian immune system has evolved unique genetic mechanisms that enable it to generate an almost unlimited number of different light and heavy chains in a remarkably economical way by joining separate gene segments together before they are transcribed. For each type of Ig chain—κ light chains, λ light chains, and heavy chain—there is a separate pool of gene segments from which a single peptide chain is eventually synthesized. Each pool is on a different chromosome and usually contains a large number of gene segments encoding the V region of an Ig chain and a smaller number of gene segments encoding the C region. During B cell development a complete coding sequence for each of the two Ig chains to be synthesized is assembled by site-specific genetic recombination, bringing together the entire coding sequences for a V region and the coding sequence for a C region. In addition, the V region of a light chain is encoded by a DNA sequence assembled from two gene segments—a V gene segment and short joining or J gene segment. The V region of a heavy chain is encoded by a DNA sequence assembled from three gene segments—a V gene segment, a J gene segment and a diversity or D segment.

The large number of inherited V, J and D gene segments available for encoding Ig chains makes a substantial contribution on its own to antibody diversity, but the combinatorial joining of these segments greatly increases this contribution. Further, imprecise joining of gene segments and somatic mutations introduced during the V-D-J segment joining at the pre-B cell stage greatly increases the diversity of the V regions.

After immunization against an antigen, a mammal goes through a process known as affinity maturation to produce antibodies with higher affinity toward the antigen. Such antigen-driven somatic hypermutation fine-tunes antibody responses to a given antigen, presumably due to the accumulation of point mutations specifically in both heavy-and light-chain V region coding sequences and a selected expansion of high-affinity antibody-bearing B cell clones.

Great efforts have been made to mimic such a natural maturation of antibodies against various antigens, especially antigens associated with diseases such as autoimmune diseases, cancer, AIDS and asthma. In particular, phage display technology has been used extensively to generate large libraries of antibody fragments by exploiting the capability of bacteriophage to express and display biologically functional protein molecule on its surface. Combinatorial libraries of antibodies have been generated in bacteriophage lambda expression systems which may be screened as bacteriophage plaques or as colonies of lysogens (Huse et al. (1989) Science 246: 1275; Caton and Koprowski (1990) Proc. Natl. Acad. Sci. (U.S.A.) 87: 6450; Mullinax et al (1990) Proc. Natl. Acad. Sci. (U.S.A.) 87: 8095; Persson et al. (1991) Proc. Natl. Acad. Sci. (U.S.A.) 88: 2432). Various embodiments of bacteriophage antibody display libraries and lambda phage expression libraries have been described (Kang et al. (1991) Proc. Natl. Acad. Sci. (U.S.A.) 88: 4363; Clackson et al. (1991) Nature 352: 624; McCafferty et al. (1990) Nature 348: 552; Burton et al. (1991) Proc. Natl. Acad. Sci. (U.S.A.) 88: 10134; Hoogenboom et al. (1991) Nucleic Acids Res. 19: 4133; Chang et al. (1991) J. Immunol. 147: 3610; Breitling et al. (1991) Gene 104: 147; Marks et al. (1991) J. Mol. Biol. 222: 581; Barbas et al. (1992) Proc. Natl. Acad. Sci. (U.S.A.) 89: 4457; Hawkins and Winter (1992) J. Immunol. 22: 867; Marks et al. (1992) Biotechnology 10: 779; Marks et al. (1992) J. Biol. Chem 267: 16007; Lowman et al (1991) Biochemistry 30: 10832; Lerner et al. (1992) Science 258: 1313). Also see review by Rader, C. and Barbas, C. F. (1997) "Phage display of combinatorial antibody libraries" Curr. Opin. Biotechnol. 8:503-508.

Various scFv libraries displayed on bacteriophage coat proteins have been described. Marks et al. (1992) Biotechnology 10: 779; Winter G and Milstein C (1991) Nature 349: 293; Clackson et al. (1991) op.cit.; Marks et al. (1991) J. Mol. Biol. 222: 581; Chaudhary et al. (1990) Proc. Natl. Acad. Sci. (USA) 87: 1066; Chiswell et al. (1992) TIBTECH 10: 80; and Huston et al. (1988) Proc. Natl. Acad. Sci. (USA) 85: 5879.

Generally, a phage library is created by inserting a library of a random oligonucleotide or a cDNA library encoding antibody fragment such as $V_L$ and $V_H$ into gene 3 of M13 or fd phage. Each inserted gene is expressed at the N-terminal of the gene 3 product, a minor coat protein of the phage. As a result, peptide libraries that contain diverse peptides can be constructed. The phage library is then affinity screened against immobilized target molecule of interest, such as an antigen, and specifically bound phages are recovered and amplified by infection into *Escherichia coli* host cells. Typically, the target molecule of interest such as a receptor (e.g., polypeptide, carbohydrate, glycoprotein, nucleic acid) is immobilized by covalent linkage to a chromatography resin to enrich for reactive phage by affinity chromatography) and/or labeled for screen plaques or colony lifts. This procedure is called biopanning. Finally, amplified phages can be sequenced for deduction of the specific peptide sequences. During the inherent nature of phage display, the antibodies displayed on the surface of the phage may not adopt its native conformation under such in vitro selection conditions as in a mammalian system. In addition, bacteria do not readily process, assemble, or express/secrete functional antibodies.

Transgenic animals such as mice have been used to generate fully human antibodies by using the XENOMOUSE™ technology developed by companies such as Abgenix, Inc., Fremont, Calif. and Medarex, Inc. Annandale, N.J. Strains of mice are engineered by suppressing mouse antibody gene expression and functionally replacing it with human antibody gene expression. This technology utilizes the natural power of the mouse immune system in surveillance and affinity maturation to produce a broad repertoire of high affinity antibodies. However, the breeding of such strains of transgenic mice and selection of high affinity antibodies can take a long period of time. Further, the antigen against which the pool of the human antibody is selected has to be recognized by the mouse as a foreign antigen in order to mount immune response; antibodies against a target antigen that does not have immunogenicity in a mouse may not be able selected by using this technology. In addition, there may be a regulatory issue regarding the use of transgenic animals, such as transgenic goats (developed by Genzyme Transgenics, Framingham, Mass.) and chickens (developed by Geneworks, Inc., Ann Arbor, Mich.), to produce antibody, as well as safety issues concerning containment of transgenic animals infected with recombinant viral vectors.

Antibodies and antibody fragments have also been produced in transgenic plants. Plants, such as corn plants (developed by Integrated Protein Technologies, St. Louis, Mo.), are transformed with vectors carrying antibody genes, which results in stable integration of these foreign genes into the plant genome. In comparison, most microorganisms transformed with plasmids can lose the plasmids during a prolonged fermentation. Transgenenic plant may be used as a cheaper means to produce antibody in large scales. However, due to the long growth circles of plants screening for antibody with high binding affinity toward a target antigen may not be efficient and feasible for high throughput screening in plants.

Currently, the most efficient way of generation of non-human antibody with high specificity and affinity is through using the hybridoma technology to produce monoclonal antibody against a specific antigen. The hybridoma technology invented by Milstein and Kohler revolutionized the industry of mass producing "custom-built" antibodies in vitro. Basically, a hybridoma is generated by fusing rodent antibody producing cells with immortal tumor cells (myelomas) from the bone marrow of mice. A hybridoma has the cancer cell's ability to reproduce almost indefinitely, as well as the immune cell's ability to secrete antibodies. The hybridomas producing antibodies of a determined antigen specificity and required affinity were selected, expand in clonal size and mass-produce antibodies of a single type, i.e. monoclonal antibodies.

Compared to polyclonal antibodies produced from the serum of animals, monoclonal antibody generated in hybridoma is superior in terms of antigen selectivity, specificity and binding affinity. Owing to these superior advantages associated with monoclonal antibodies, they have been hailed as "magic bullets" that could be used to specifically target diseased cells or tissues.

Although monoclonal antibodies (mAbs) generated from hybridoma technology have proved to be immensely useful scientific research and diagnostic tools, they have had a limited success in human therapy. Although murine antibodies had exquisite specificity for therapeutic targets, they did not always trigger the appropriate human effector's systems of complement and Fc receptors. More importantly, the major limitation in the clinical use of rodent monoclonal antibodies is an antiglobulin response during therapy. Miller et al. (1983) Blood 62:988-995; and Schroff al. (1985) Cancer Res. 54:879-885. The patient's immune system normally cuts short the therapeutic window, as murine antibodies are recognized by a human anti-mouse antibody immune response (HAMA). Similar to serum therapy where antisera used to neutralize pathogen in acute diseases and also prophylactically leads to "serum sickness", the patient treated with rodent mAbs in multiple doses invariably raises an immune response to the mAbs, manifesting similar symptoms to serum sickness and violent enough to endanger life. This response can occur within two weeks of the initiation of treatment and precludes long-term therapy. Efforts have been made to raise human mAbs against therapeutic targets through immortalization of human antibody-producing cells. The endeavors face various practical and ethical problems, such as the difficulties with preparation of human hybridomas that are unstable and secrete low levels of mAbs of the IgM class with low affinity.

To produce therapeutic antibodies with high binding affinity, reduced immunogenicity (HAMA response), increased half-life in the human body and adequate recruitment of effectors functions (i.e. the ability to summon help from the body's own natural defense), people in the art have combined the techniques of monoclonal antibody production and recombinant DNA technology to overcome the problem associated with rodent monoclonal antibodies. Besides direct generation of fully human antibody as described above, another popular approach is to humanize rodent monoclonal antibody.

The technique of rodent antibody humanization takes advantage of the modular nature of antibody functions. It is based on the assumption that it's possible to convert a rodent, e.g., mouse, monoclonal antibody into one that has some human segments but still retains its original antigen binding specificity. Such a chimeric antibody is humanized in a sense that the mainframe of the antibody has human sequence whereas the antigen binding site have sequences derived from the counterparts of the mouse monoclonal antibody.

Initially, the mouse Fc fragment was replaced with a human sequence because the mouse Fc functions poorly as an effector of immunological responses in humans; and it is also the most likely fragment to elicit the production of human antibodies. To diminish immunogenicity and to introduce human Fc effector capabilities; the DNA coding sequences for the Fv regions of both the light and heavy chains of a human immunoglobulin were substituted for the FvDNA sequences for the light and heavy chains from a specific mouse monoclonal antibody. LoBuglio et al. (1989) Proc. Natl. Acad. Sci. USA 86:4220-4224. This replacement of Fv coding regions can be accomplished by using oligonucleotides and in vitro DNA replication or by using subclonal segments. The DNA constructs for both chimeric chains were cloned into an expression vector and transfected into cultured B lymphocytes from which the chimeric antibody was collected.

Later the humanizing of mouse and rat monoclonal antibodies has been taken one step further than the formation of chimeric molecule described above by substituting into human antibodies on the CDRs of the rodent antibodies, a process called "CDR grafting". Queen et al. (1989) Proc. Natl. Acad. Sci. USA 86: 10029-10033. It was believed that such a "reshaped" human antibodies have antigen binding affinities similar to those of the original rodent monoclonal antibodies and yet has a reduced immunogenicity when used as a therapeutic agent in the clinic. Currently, CDR grafting is the most frequently used strategy for the humanization of murine mAbs. In this approach the six CDR loops comprising the antigen-binding site of the murine mAb are grafted into corresponding human framework regions. However pure CDR-grafting often yields humanized antibodies with much lower affinity (Jones et al. (1986) Nature 321:522-525), in some instances as much as 10-fold or more, especially when the antigen is a protein (Verhoeyen et al. (1988) Science 239:1534-1536). Such an antibody with reduced affinity is undesirable in that 1) more of the humanized antibody would have to be administered into a patient at higher cost and greater risk of adverse effects; 2) lower affinity antibody may have poorer biological functions, such as complement lysis, antibody-dependent cellular cytotoxicity, or virus neutralization. Riechmann et al. (1988) Nature 332: 323-327.

To search for humanized antibody with higher affinity, Queen et al. have used computer modeling software to guide the humanization of promising murine antibodies. U.S. Pat. No. 5,693,762. The structure of a specific antibody is predicted based on computer modeling and the few key amino acids in the framework are predicted to be necessary to retain the shape, and thus the binding specificity, of the CDRs. These few key murine amino acids are substituted into a human antibody framework along with the murine CDRs. As a result, the humanized antibody includes about 90% human sequence. The humanized antibody designed by computer modeling is tested for antigen binding. Experimental results such as binding affinity are fed back to the computer modeling process to fine-tune the structure of the humanized antibody. The redesigned antibody can then be tested for improved biological functions. Such a reiterate fine tuning process can be labor intensive and unpredictable.

SUMMARY OF THE INVENTION

The present invention provides compositions, methods, and kits for efficiently generating and screening humanized antibody with high affinity against a specific antigen. One feature of the present invention is that a library of humanized antibody is generated by mutagenizing a chimeric antibody template that combines human antibody framework and antigen binding sites of a non-human antibody.

Alternatively, the library of humanized antibody is generated by grafting essential antigen-recognition segment(s) of the non-human antibody into the corresponding position(s) of each member of a human antibody library. This library of humanized antibody is then screened for high affinity binding toward a specific antigen in vivo in organism such as yeast or in vitro using techniques such as ribosome display or mRNA display.

The specific antigen used in the screening can be the one against which the non-human antibody is originally elicited, or an antigen with similar structural features or biological function. In addition, the library of humanized antibody may be used in screening for high affinity antibody against an antigen that is structurally and/or functionally different from the antigen against which the non-human antibody is originally elicited.

These selection processes can be performed to select antibody having higher affinity in antigen binding but lower immunogenecity than rodent monoclonal antibody. The overall process can be efficiently performed in a high throughput and automated manner, thus mimicking the natural process of antibody affinity maturation.

BRIEF DESCRIPTION OF FIGURES

FIG. 1 illustrates the variable regions of the heavy chain and light chain of a non-human antibody to be humanized. The CDR regions between the framework of this antibody are labeled as CDR1, CDR2, and CDR3 sequentially from the N-terminus to the C-terminus.

FIG. 2 illustrates an example of a chimeric antibody having non-human CDRs 1-3 grafted into a human antibody framework.

FIG. 3 shows the DNA sequences of a consensus $V_H$ (DP47) and a consensus $V_L$ (DPK22) of human antibody germline sequences.

FIG. 4A shows the DNA and amino acid sequences of $V_H$ and $V_L$ of a mouse monoclonal anti-interleukin-8 antibody (Murine IL-8 Ab).

FIG. 4B shows the amino acid sequences of $V_H$ of human antibody Kabat Entry No: 037656 and VL of human antibody Kabat Entry No: 039682 which share high sequence homology to $V_H$ and $V_L$ of Murine IL-8 Ab in FIG. 4A, respectively.

FIG. 5A shows alignment of $V_H$ of murine IL-8 Ab shown in FIG. 4A and $V_H$ of human antibody Kabat Entry No: 037656 shown in FIG. 4B.

FIG. 5B shows alignment of $V_L$ of murine IL-8 Ab shown in FIG. 4A and $V_L$ of human antibody Kabat Entry No: 039682 shown in FIG. 4B.

FIG. 6 illustrates an embodiment of the method for generating, expressing, and screening in yeast a library of humanized antibody into which the CDRs of non-human antibody are grafted.

FIG. 7 illustrates an embodiment of the method for generating, expressing, and screening in yeast a library of humanized antibody into which CDR3 of non-human antibody is grafted.

FIG. 8 illustrates an embodiment of the method for generating, expressing, and screening in yeast a library of fully human antibody, which is directed by $V_H$ of a non-human antibody.

DETAILED DESCRIPTION OF THE INVENTION

Figure 9:
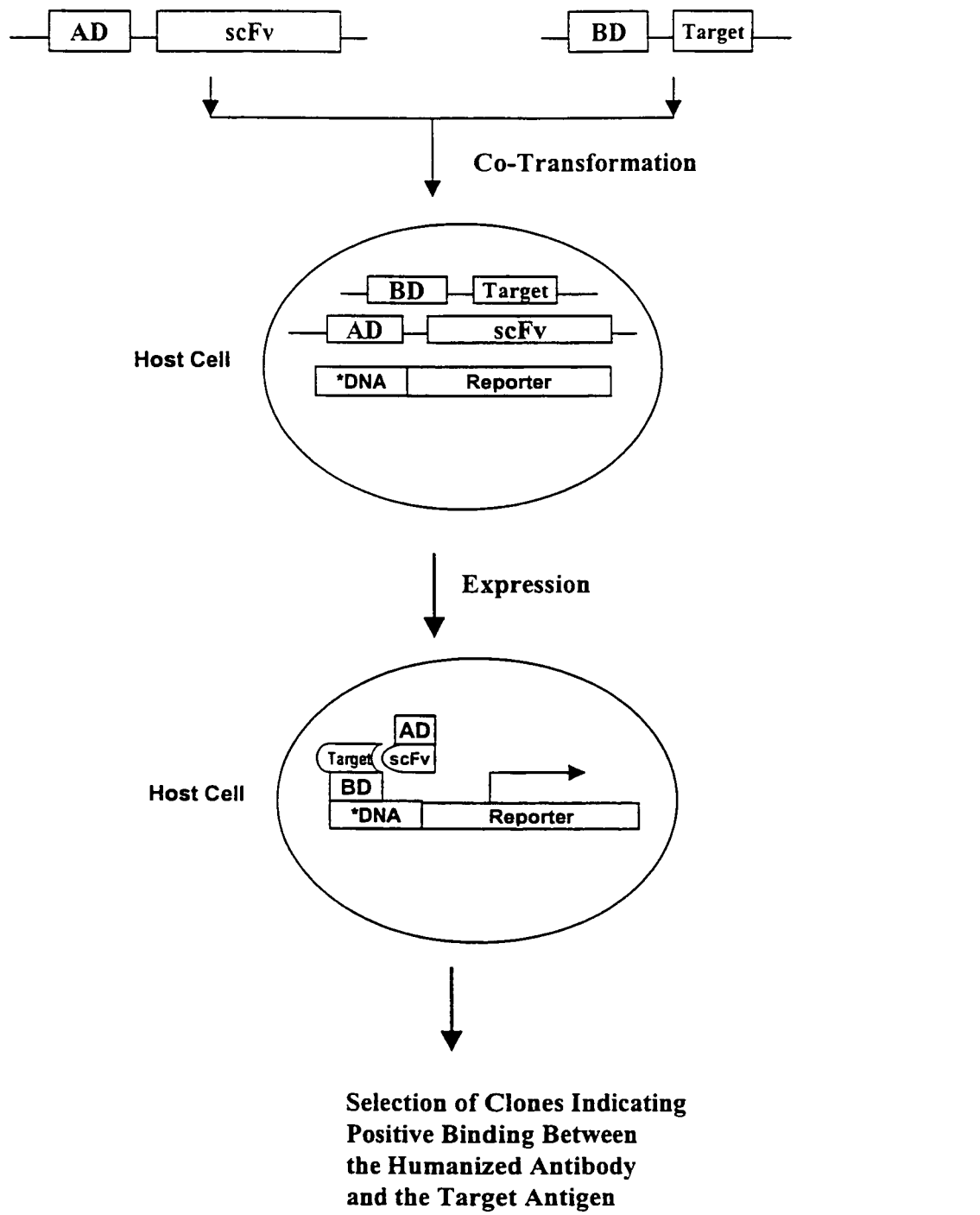
FIG. 9 illustrates an embodiment of the method for selecting humanized single-chain antibody (scFv) against a target protein in a two-hybrid system where the expression vectors carrying the AD and BD domains are co-transformed or sequentially transformed into yeast.

The present invention provides novel methods for efficiently generating and screening humanized antibody with high affinity against a specific antigen. Compared to approaches that use stepwise tailoring and designing of individual humanized antibody in silicon (i.e. computer modeling), the humanization process according to the present invention is performed in vitro or in vivo and screened directly against the target antigen. Therefore, the present approach is more robust and more directly mimics the natural process of antibody affinity maturation in vertebrates. By using the methods of the present invention, non-human antibody can be humanized not only without loss in antigen-binding affinity but also with improved affinity and other biological functions. The whole process of antibody humanization and affinity maturation can be performed in a high throughput manner.

In one aspect of the present invention, a method is provided for humanizing a non-human antibody by mutagenesis. The method comprises: constructing a chimeric antibody sequence by combining a human antibody framework sequence with one or more non-human antibody segments that are essential for affinity binding to a target antigen against which the non-human antibody is elicited; mutagenizing the chimeric antibody sequence to produce a library of humanized antibody sequences.

In another aspect of the present invention, a method is provided for humanizing a non-human antibody by grafting non-human antibody segments into a library of human antibody sequences. The method comprises: grafting one or more non-human antibody segments into a library of human antibody framework sequences to produce a library of humanized antibody sequences. The non-human antibody segments grafted are essential for affinity binding to a target antigen against which the non-human antibody is elicited.

The library of humanized antibody sequences are expressed in vitro or in vivo to produce a library of humanized antibodies which can be screened for high affinity bind to a target antigen. In one embodiment, the library of humanized antibody sequences is expressed in vivo and screened against the target antigen in yeast, preferably in a yeast two-hybrid system. In another embodiment, the library of humanized antibody sequences is expressed and screened in vitro against the target antigen, preferably by ribosome display.

It should be noted that the specific antigen used in the screening can be the one against which the non-human antibody is originally elicited, or an antigen with similar structural features or biological function.

These selection processes can be performed to select antibody having higher affinity in antigen binding but lower immunogenecity than rodent monoclonal antibody. In contrast to the approach using computer modeling of individually humanized antibody and subsequent experimental screening, the overall process of the present invention can be efficiently performed in a high throughput and automated manner, thus mimicking the natural process of antibody affinity maturation.

The present invention provides methods for producing and screening humanized antibody with high affinity and specificity. The methods are efficient, comprehensive and complementary.

First, the method of producing and screening an antibody library in yeast is an efficient and economical way to screen for humanized antibodies in a much shorter period of time. In addition, production of the library of humanized antibody sequence can be carried out in a high throughput manner in yeast by exploiting the intrinsic genetic property of yeast—homologous recombination at an extremely high level of efficiency. This process will be described in details in Section 2 below.

The fast proliferation rate of yeast cells and ease of handling makes a process of "molecular evolution" dramatically shorter than the natural process of antibody affinity maturation in a mammal. Therefore, humanized antibody repertoire can be produced and screened directly in yeast cells at a much lower cost and higher efficiency than prior processes such as the painstaking, stepwise "humanization" of monoclonal murine antibodies isolated by using the conventional hybridoma technology (a "protein redesign") or the XENOMOUSE™ technology.

According to the "protein redesign" approach, murine monoclonal antibodies of desired antigen specificity are modified or "humanized" in vitro in an attempt to reshape the murine antibody to resemble more closely its human counterpart while retaining the original antigen-binding specificity. Riechmann et al. (1988) Nature 332:323-327. This humanization demands extensive, systematic and reiterate computer engineering and experimental validation of the murine antibody, which could take months, if not years.

In addition, this approach can bear the risk of empirical guessing or wrong prediction based on sequence comparison and structural modeling.

In comparison, by using the method of the present invention, humanized antibodies with perhaps even higher affinity to a specified antigen than the original non-human antibody can be screened and isolated directly from yeast cells without going through reiterate site-by-site computer engineering and experimental validation. The library of humanized antibody can diversified by site-directed or random mutagenesis and directly screened against the target antigen in vivo in yeast or via ribosome display in vitro. The selected humanized antibody can be further mutagenized and screened again for higher affinity binder to the same target antigen. This reiterate process mimics the natural process of antibody maturation in vertebrates.

Further, by using the method of the present invention, many requisite steps in the traditional construction of cDNA libraries can be eliminated. For example, the time-consuming and labor-intensive steps of ligation and recloning of cDNA libraries into expression vectors can be eliminated by direct recombination or "gap-filling" in yeast through general homologous recombination and/or site-specific recombination. Throughout the whole process of humanized antibody library construction, the DNA fragments encoding antibody heavy chain and light chain are directly incorporated into a linearized yeast expression vector via homologous recombination without the recourse to extensive recloning.

Moreover, the library of humanized antibody can also be screened against an array of antigens to identify those which bind to a specific antigen in the array with the highest affinity.

In addition, by using the method of present inventions, multiple humanized antibody may be selected against the same target antigen. In clinical therapeutic applications, if the one of these antibodies elicits an anti-idiotypic response in the patient, another one from the same group of antibodies can be used to substitute the idiotypic one, thus allowing the therapy to continue without ablating the therapeutic efficacy.

Second, the methods are more comprehensive than the XENOMOUSE™ technology. The XENOMOUSE™ technology has been used to generate fully human antibodies with high affinity by creating strains of transgenic mice that produce human antibodies while suppressing the endogenous murine Ig heavy- and light-chain loci. However, the breeding of such strains of transgenic mice and selection of high affinity antibodies can take a long period of time. The antigen against which the pool of the human antibody is selected has to be recognized by the mouse as a foreign antigen in order to mount immune response; and antibodies against a target antigen that does not have immunogenicity in a mouse may not be able to be selected by using this technology.

In contrast, by using the method of the present invention, libraries of humanized antibody can not only be generated in yeast cells more efficiently and economically, but also be screened against virtually any protein or peptide target regardless of its immunogenicity. According to the present invention, any protein/peptide target can be expressed as a fusion protein with a DNA-binding domain (or an activation domain) of a transcription activator and selected against the library of antibody in a yeast-2-hybrid system.

Third, the methods provided by the present invention are complementary. On one hand, a yeast two-hybrid system can be used to screen for high affinity humanized antibody against any protein antigen expressed intracellularly. On the other hand, a ribosome display method can be used to display the library of humanized antibody on the surface of ribosomes and screened for virtually any ligand. Since the ribosome display is performed by in vitro translation of mRNA encoding the library of humanized antibody in a cell lysate, the library of humanized antibody bound to the ribosomes can be screened against any ligand immobilized on a substrate. The immobilized ligand can be a small molecule, a peptide, a protein, and a nucleic acid.

The preferred embodiments of the methods for generation and affinity maturation of humanized antibody are described as follows.

1. Generation of a Library of Humanized Antibody

The present invention provides methods for generating a library of humanized antibody that can be used for screening for antibody with high affinity toward a specific antigen. The humanized antibodies in the library contain a human framework and essential antigen binding segment(s) derived from a non-human antibody, such as a mouse or rat antibody. The following are examples of how to generate such a library of humanized antibody 1) Construction of a Library of Humanized Antibody by Creating a Chimeric Antibody by Grafting Essential Antigen Recognition Segments of a Non-Human Antibody into a Single Human Antibody Framework, and Mutagenizing the Chimeric Antibody In this embodiment, the library of humanized antibody sequences is constructed by grafting sequences encoding essential antigen-bind segments (e.g., CDRs) of a non-human antibody (e.g., a mouse monoclonal antibody) into the sequence encoding a single human antibody framework. Through this grafting process, a chimeric antibody sequence is created to encode a chimeric antibody including both human and non-human antibody sequences. The chimeric antibody sequence is mutagenized to produce a library of humanized antibody sequences.

FIG. 1 illustrates the variable regions of the heavy chain and light chain of a non-human antibody. As illustrated by FIG. 1, the segments that most likely determine the antigen-binding affinity of the non-human antibody are CDR regions, including CDR 1, CDR2, and CDR3 located in the variable regions of the heavy chain and light chain. The rest of the sequences of the variable regions of the heavy chain and light chain constitute the framework sequences of the antibody.

FIG. 2 illustrates the variable regions of the heavy chain and light chain of a chimeric antibody. The sequences encoding the CDR regions of a non-human antibody (as shown in FIG. 1) are grafted into the variables regions of a human antibody by replacing the human CDRs in their corresponding positions. As a result, a chimeric antibody sequence is created, including both human and non-human antibody sequences.

In this chimeric antibody the human antibody framework sequence serves as a framework to accommodate the non-human CDRs and provides structural support for global folding of the antibody structure. The human framework sequence may be chosen based on various criteria.

For example, a fixed human antibody framework sequence may be used to provide the structural support for the chimeric antibody. In this case, a single vector containing the chosen human antibody framework can be created to accept all non-human CDRs, generating humanized antibodies with similar expression and performance.

The fixed human antibody framework sequence may be derived from natural human antibodies, such as framework "NEW" (Saul F A et al. "Preliminary refinement and structural analysis of the Fab fragment from human immunoglobulin NEW at 2.0 A resolution" *J Biol Chem* (1978) 253(2): 585-597; and Riechmann et al. "Reshaping human antibodies for therapy." *Nature* (1988) 332: 323-327) for the heavy chain and framework "REI" (Epp et al. "Crystal and molecular structure of a dimer composed of the variable portions of the Bence-Jones protein REI." *Eur J Biochem.* (1974) 45(2):513-524; and Riechmann et al. "Reshaping human antibodies for therapy." *Nature* (1988) 332: 323-327) for the light chain. Although these human antibodies are well characterized, using the frameworks from particular human antibodies for humanization may run a risk of somatic mutation that creates immunogenic epitopes.

In a preferred embodiment, the frameworks from human antibody consensus sequences where idiosyncratic somatic mutations have been "evened out" are used to provide the human antibody frameworks of the present invention. Kabat et al. "Sequences of Proteins of Immunological Interest" Fifth Edition. (1991) NIH Publication No. 91-3242; and Kolbinger F, Saldanha J, Hardman N and Bendig M "Humanization of a mouse anti-human IgE antibody: a potential therapeutic for IgE-mediated allergies" *Prot. Engng.* (1993) 6: 971-980.

In another preferred embodiment, the human framework sequence is derived from consensus human germline sequences. Human antibodies are assembled from 51 different functional $V_H$ germ line genes and 70 different functional $V_L$ segments (40 Vκ and 30 Vλ). However, one $V_H$ (DP47, its DNA SEQ ID NO: 1) and one Vκ (DPK22, its DNA SEQ ID NO: 2) dominate the functional repertoire (Kirkham, P. M. et al. (1992) *EMBO J.* 11:603-609). FIG. 3 shows the DNA sequences of DP47 and DPK22.

These two germ line gene segments are used as frameworks for CDR grafting. The gene sequences are examined for all possible restriction endonuclease sites, which could be introduced without changing the corresponding amino acid sequences. Cleavage sites are chosen that are located close to the CDR and framework borders and are unique. The resulting gene fragments are assembled from overlapping oligonucleotides on alternating strands by overlap-extension PCR. By cloning these synthesized gene fragments into appropriate vectors, two modular cassettes are generated into which any either heavy chain or light chain CDRs can be easily inserted. The donor CDRs will be individually amplified by PCR using primers that introduce restriction sites compatible to those in the framework cassettes. The CDRs will then be grafted into the frameworks by restriction digestion and ligation.

For example, mouse monoclonal antibody against interleukin-8 (Murine IL-8 Ab, ATCC No: HB-9647, Yoshimura et al. (1989) "Three forms of monocyte-derived neutrophil chemotactic factor (MDNCF) distinguished by different lengths of the amino-terminal sequence" Mol. Immunol. 26: 87-93; and Sylvester et al. (1990) "Secretion of neutrophil attractant/activation protein by lipopolysaccharide-stimulated lung macrophages determined by both enzyme-linked immunosorbent assay and N-terminal sequence analysis" Am. Rev. Respir. Dis. 141: 683-688.) may be humanized by grafting its CDR regions into a human antibody framework such as DP47 for heavy chain and DPK22 for light chain, respectively. FIG. 4A shows the DNA and amino acid sequences of $V_H$ and $V_L$ of Murine IL-8 Ab (murine $V_H$: DNA [SEQ ID NO: 4] and protein [SEQ ID NO: 5]; and murine $V_L$: DNA [SEQ ID NO: 6] and protein [SEQ ID NO: 7]. The resulting chimeric antibody may be mutagenized throughout the variable region to produce a library of humanized antibodies which are then screened for antibodies with high affinity toward a specific target, such as IL-8.

Alternatively, the CDRs of the non-human antibody may be grafted into a human framework through a homology match. In another word, amino acid sequences of human antibody framework sequences are searched for best homology with that of the non-human antibody to be humanized. The homology may be searched within an appropriate database of either human antibodies or human germline sequences. Ideally, the human antibody chosen should share the highest percentage identity with the non-human antibody in the length of the CDRs and the canonical residue. Once the framework sequences of the human antibody are chosen, the humanized $V_H$ and $V_L$ genes are assembled from overlapping oligonucleotides by overlap-extension PCR.

For example, the amino acid sequence of the Murine IL-8 Ab described above may be aligned with human antibody frameworks within a human antibody database, such as the Kabat database of human antibody. FIG. 4B shows the amino acid sequences of $V_H$ of a human antibody against CD19 (Kabat Entry No: 037656, Bejcek et al. (1995) "Development and characterization of three recombinant single chain antibody fragments (scFvs) directed against the CD19 antigen" Cancer Res. 55:2346-51) within the Kabat database which shares a high percentage identity (85.5%) with the Murine IL-8 Ab in the framework regions. FIG. 4B also shows the amino acid sequences of $V_L$ of a human antibody against the dominant epitope of the group A *Streptococcal carbohudrate*, N-acetyl-beta-D-glucosamine, (Kabat Entry No: 039682, Adderson et al. (1998) "Molecular analysis of polyreactive monoclonal antibodies from *rheumatic carditis*: human anti-N-acetylglucosamine/anti-myosin antibody V region genes" J Immunol. 161:2020-31) within the Kabat database which shares a high percentage identity (80.2%) with the Murine IL-8 Ab in the framework regions.

FIGS. 5A and 5B show amino acid sequence alignments of $V_H$ and $V_L$ of the Murine IL-8 Ab (HB-9647) with $V_H$ of human antibody Kabat Entry No: 037656 and $V_L$ of human antibody Kabat Entry No: 039682 in the framework region, respectively. Amino acid residues that are not homologous to those of the Murine IL-8 Ab in the framework regions are in bold.

As shown in FIG. 5A, CDR regions designated by Kabat in $V_H$ region are framed in boxes (CDR1, aa 31-35B; CDR2, aa 50-65; and CDR3, aa 95-102) while those designated by Chothia are highlighted in gray areas (CDR1, aa 26-32; CDR2, aa 52-56; and CDR3, aa 95-102).

As shown in FIG. 5B, CDR regions designated by Kabat in $V_L$ region are framed in boxes (CDR1, aa 24-34; CDR2, aa 50-56; and CDR3, aa 89-97) while those designated by Chothia are highlighted in gray areas (CDR1, aa 24-34; CDR2, aa 50-56; and CDR3, aa 89-96).

As shown in FIG. 5A, $V_H$ of human antibody Kabat Entry No: 037656 shares a very high sequence homology (85.5%) with that of the Murine IL-8 Ab in the framework region of $V_H$. As shown in FIG. 5B, $V_L$ of human antibody Kabat Entry No: 039682 shares a very high sequence homology (80.2%) with that of the Murine IL-8 Ab in the framework region of $V_L$. Thus, the frameworks of $V_H$ of human antibody Kabat Entry No: 037656 and $V_L$ of human antibody Kabat Entry No: 039682 can serve as the frameworks to accommodate the CDR regions of the Murine IL-8 Ab in $V_H$ and $V_L$ regions, respectively. Preferably, the CDR sequences that are selected to be grafted into the human framework are the maximized CDR sequences including both Kabat and Chothia CDRs. For the Murine IL-8 Ab, the CDRs to be grafted into the frameworks of $V_H$ of human antibody Kabat Entry No: 037656 and $V_L$ of human antibody Kabat Entry No: 039682 are as follows:

For $V_H$, CDR1, aa 26-35B; CDR2, aa 50-65; and CDR3, aa 95-102.

For $V_L$, CDR1, aa 24-34; CDR2, aa 50-56; and CDR3, aa 89-97.

The resulting chimeric antibody may be mutagenized throughout the variable region to produce a library of humanized antibodies which are then screened for antibodies with high affinity toward a specific target, such as IL-8.

The humanized $V_H$ and $V_L$ genes that combines the human framework sequence and the non-human CDRs of the heavy chain and light chain, respectively, may cloned into an expression vector or into two expression vectors separately. In this design, the $V_H$ and $V_L$ genes can be expressed to form a double chain chimeric antibody (dcFv).

Alternatively, the humanized $V_H$ and $V_L$ genes may be assembled by PCR to form a single chain chimeric antibody (scFv). Specifically, the $V_H$ and $V_L$ gene fragments generated above are assembled into a single fragment by PCR which adds a linker between $V_H$ and $V_L$. A typical linker region for a single chain antibody is 4 tandem repeats of (GlyGlyGlyGlySer) [SEQ ID NO: 3].

During the PCR assembly, mutagenesis is introduced into the single chain chimeric antibody sequence. For example, error-prone PCR can be used in this process to incorporate random mutations throughout the reading frames in both the heavy chain and light chain of the chimeric antibody sequence. As a result, a library of humanized antibody sequences is constructed.

FIG. 6 illustrates an example of the method for constructing a library of humanized antibody sequences contained in a yeast expression vector. As illustrated in FIG. 6, the framework sequences of a human light chain and a heavy chain are separately contained in a cloning vector (e.g, pUC19). CDR sequences from a non-human antibody are grafted into the framework sequence at the individual, unique restriction sites in the corresponding positions of the human CDR regions. These chimeric heavy chain and light chain sequences contained in the cloning vectors are assembled by PCR in the presence of a linker sequence to form a chimeric scFv fragment. During the PCR assembly process random mutagenesis is also performed to introduce mutations into the chimeric scFv. As a result, a library of humanized antibody sequences is generated.

As illustrated in FIG. 6, the PCR primers are designed to include sequences flanking the chimeric scFv that can facilitate subsequent homologous recombination of the scFv into a yeast expression vector. The library of humanized antibody sequences generated by PCR assembly is then cloned into a yeast expression vector, such as a yeast two-hybrid vector containing an activation domain (e.g, pACT2, Clontech, Palo Alto, Calif.). The two-hybrid vector is linearized with a single restriction enzyme in the multiple cloning site (MCS). The library of humanized antibody may then be co-transformed with the linearized vector into a competent yeast strain. The successful homologous recombination should generate a library of mutagenzied scFvs fused with the activation domain. High affinity mutants can be isolated from this library in a yeast two-hybrid screening. The process of yeast homologous recombination and two-hybrid screening is described in more details in Section 2.

2) Construction of a Library of Yeast Expression Vectors Containing Humanized Antibody Sequences by Grafting Essential Antigen Recognition Segments of a Non-Human Antibody into a Library of Human Antibody Sequences.

In this embodiment, the library of humanized antibody sequences is constructed by grafting sequences encoding essential antigen recognition segments (e.g., CDRs) of a non-human antibody (e.g., a mouse monoclonal antibody) into the framework sequences of a library of human antibody sequences. Through this grafting process, a library of chimeric antibody sequences is created to encode a library of chimeric antibodies including both human and non-human antibody sequences. Such a library of chimeric antibody sequences is cloned into a yeast expression vector to generate a library of yeast expression vectors containing humanized antibody sequences.

This humanization strategy involves two selection steps for the sequential humanization of the light chain and the Fd fragment of the heavy chain. Throughout these selections the only preserved sequences in the variable domains are two of the six CDRs, LCDR3 of $V_L$ and HCDR3 of $V_H$. FIG. 7 illustrates an example of the method of constructing a library of humanized antibody sequences containing only CDR3 regions of the non-human antibody.

In the first step, the light chain of the non-human antibody is humanized by incorporating the non-human LCDR3 sequence into a library of human antibody $V_L$ sequences. Degenerate PCR primers are used to amplify the fragment encoding framework 1 (FR1) through framework 3 (FR3) from a human antibody library. By overlap-extension PCR, this fragment is then fused with a PCR fragment encoding the LCDR3 of the non-human antibody coupled to FR4 of human Vκ and the human Cκ domain. The FR4 of the human antibody can be chosen based on homology to the non-human FR4; and changes in this region should have little effect on the affinity. This process generates a library of human light chain that contains the LCDR3 of the non-human antibody. These PCR fragments can be cloned into a yeast two-hybrid vector containing the activation domain (AD).

A chimeric heavy chain Fd fragment can be generated by fusing the non-human $V_H$ with human $C_H1$ and cloned into the same two-hybrid vector. A zipper or bundle domain (described in detail below) may be fused to VH and VL of the chimeric antibody to facilitate assembly of these two fragments in yeast. By using the yeast two-hybrid screening method (described in detail in Section 2), chimeric Fab with high affinity toward the target antigen can be selected.

In the second step, the heavy chain of the non-human antibody is humanized by incorporating the non-human HCDR3 sequence into a library of human antibody $V_H$ sequences (FIG. 7). Following a similar procedure to that in step 1, a library of human Fd fragment that contain the HCDR3 of the non-human antibody can constructed. These fragments are then cloned into the yeast two-hybrid vector containing the humanized light chain selected from step 1. A second round of screening will lead to the selection of humanized Fab with high affinity toward to the target antigen.

In this preferred embodiment, a yeast two-hybrid vector containing an activation domain (e.g., pACT2, Clontech, Palo Alto, Calif.) is modified to express Fab fragment, each composed of a chimeric heavy chain and a chimeric light chain from the libraries described above. In the Fab fragment, one or more human constant regions (Cκ of the light chain and CH1 of the heavy chain) are included to stabilize the Fab of the selection steps through intermolecular interactions between the two matching human constant regions.

Alternatively, $V_H$ and $V_L$ can be expressed as fusion proteins with a zipper domain or a bundle domain to facilitate assembly of $V_H$ and $V_L$ to form a stable Fab.

A zipper domain is a protein or peptide structural motif that interacts with each other through non-covalent interactions such as coiled-coil interactions and brings other proteins fused with the zipper domains into close proximity. Examples of zipper domains include, but are not limited to, leucine zippers (or helix-loop-helix, also called bHLHzip motif) formed between the nuclear oncoproteins Fos and Jun (Kouzarides and Tiff (1989) "Behind the Fos and Jun leucine zipper' Cancer Cells 1: 71-76); leucine zippers formed between proto-oncoproteins Myc and Max (Luscher and Larsson (1999) "The basic region/helix-loop-helix/leucine zipper domain of Myc proto-oncoproteins: function and regulation" Oncogene 18:2955-2966); zipper motifs from adhesion proteins such as N-terminal domain of neural cadherin (Weis (1995) "Cadherin structure: a revealing zipper" 3:425-427); zipper-like structural motifs from collagen triple helices or cartilage oligomeric matrix proteins (Engel and Prockop "The zipper-like folding of collagen triple helices and the effects of mutations that disrupt the zipper" Annu. Rev. Biophys. Biophys. Chem. 20:137-152; and Terskikh et al. (1997) "Peptabody": a new type of high avidity binding protein" Proc. Natl. Acad. Sci. USA 94:1663-1668).

The zipper domain may be fused to the N- or C- terminus of the humanized antibody $V_H$ or $V_L$, preferably at the C-terminus of the subunits. For example, the leucine zipper domain derived from the oncoprotein Jun can be expressed as a fusion protein with $V_H$ whereas the leucine zipper domain derived from the oncoprotein Fos can be expressed as another fusion protein with $V_L$. Since the Jun and Fos leucine zipper domains can bind to each other with high affinity, the antibody heavy chain and light chain fused with Jun and Fos zipper, respectively, can be brought into close proximity and form a heterodimer upon binding between these two zipper domains.

It is believed that by adding a zipper domain near the termini of the subunits, the intermolecular interactions between the two subunits should be enhanced through non-covalent interactions (e.g. hydrophobic interactions), thus further stabilizing the assembly of Fab formed by the humanized $V_H$ and $V_L$. Moreover, fusing a zipper domain derived from nuclear protein such as Jun and Fos to $V_H$ and $V_L$ may facilitate efficient transportation of $V_H$ and $V_L$ to the nucleus where the Fab formed between the $V_H$ and $V_L$ performs desired functions such as transcriptional activation of a reporter gene.

As used herein, a "bundle domain" refers to a protein or peptide structural motif that can interact with itself to form a homo-polymer such as a homopentalmer. The bundle domains bring the protein complex together by polymerization through non-covalent interactions such as coiled-coil interactions. It is believed that polymerization of the $V_H$ and $V_L$ should enhance the avidity of the Fab to their binding target through multivalent binding.

For example, the coiled-coil assembly domain of the cartilage oligomeric matrix protein (COMP) may serve as a bundle domain. The N-terminal fragment of rat COMP comprises residue 20-83. This fragment can form pentamers sinillar to the assembly domain of the native protein. The fragment adopts a predominantly alpha-helical structure. Efimov et al. (1994) "The thrombospondin-like chains of cartilage oligomeric matrix protein are assembled by a five-stranded alpha-helical bundle between residues 20 and 83" FEBS Lett. 341:54-58.

The coiled-coil domain of the nudE gene of the filamentous fungus *Aspergillu nidulans* or the gene encoding the nuclear distribution protein RO11 of *Neurospora crassa* may also serve a bundle domain. The product of the nudE gene, NUDE, is a homologue of the RO11 protein. The N-terminal coiled-coil domain of the NUDE protein is highly conserved; and a similar coiled-coil domain is present in several putative human proteins and in the mitotic phosphoprotein 43 (MP43) of *X laevis*. Efimov and Morris (2000) "The LIS1-related NUDF protein of *Aspergillus nidulans* interacts with the coiled-coil domain of the NUDE/RO11 protein" J. Cell Biol. 150:681-688.

In addition, the coiled-coil segments or fribritin encoded by bacteriophage T4 may also serve as a bundle domain. The bacteriophage T4 late gene wac (Whisker's antigen control) encodes a fibrous protein which forms a collar/whiskers complex. Analysis of the 486 amino acid sequence of fibritin reveals three structural components: a 408 amino acid region that contains 12 putative coiled-coil segments with a canonical heptad (a-b-c-d-e-f-g)n substructure where the "a" and "d" positions are preferentially occupied by apolar residues, and the N and C-terminal domains (47 and 29 amino acid residues, respectively). The alpha-helical segments are separated by short "linker" regions, variable in length, that have a high proportion of glycine and proline residues. Co-assembly of full-length fibritin and the N-terminal deletion mutant, as well as analytical centrifugation, indicates that the protein is a parallel triple-standard alpha-helical coiled-coil. The last 18 C-terminal residues of fibritin are required for correct trimerisation of gpwac monomers in vivo. Efimov et al. (1994) "Fibritin encoded by bacteriophage T4 gene wac has a parallel triple-stranded alpha-helical coiled-coiled structure" J. Mol. Biol. 242:470-486.

3) Construction of a Library of Fully Human Antibody Sequences Directed by Essential Antigen Recognition Segment(s) of a Non-Human Antibody In this embodiment, a library of fully human antibody sequences is constructed by a directed selection from two separate pools of fully human antibody light chain and heavy chain sequences. The selection is directed toward a chimeric antibody heavy chain comprising essential antigen recognition segments (e.g., $V_H$ or CDRs of the heavy chain) of a non-human antibody and a human framework sequence such as a constant region of a human antibody. The light chains from human antibody gene pool and the chimeric heavy chain are expressed and assembled in vivo to form a library of chimeric Fab. This library of double chain Fab containing the chimeric light chain is selected against the original antigen against which the non-human antibody is elicited. The fully human light chain(s) of the chimeric Fab(s) selected in this process is then matched with a pool of fully human antibody heavy chain sequences to form a library of fully human antibody sequences. This library is screened against the original antigen again to select for those fully human antibodies with high affinity toward the original antigen. As a result, the selected antibody is not only fully human but also may have potentially higher affinity toward the antigen than the original non-human antibody. This fully human antibody should have the advantage of being less immunogenic than a chimeric antibody which includes partially human and partially non-human sequences.

The cDNA gene pool for the heavy chain or light chain of fully human antibody may generated by using the methods known in the art. Sambrook, J., et al. (1989) Molecular Cloning: a laboratory manual. Cold Spring Harbor Laboratory, Cold Spring Harbor, N.Y.; and Ausubel, F. M. et al. (1995) Current Protocols in Molecular Biology" John Wiley & Sons, New York.

Total RNA may be isolated from sources such as the white cells (mainly B cells) contained in peripheral blood supplied by unimmunized humans, or from human fetal spleen and lymph nodes. First strand cDNA synthesis may be synthesized performed by using methods known in the art, such as those described by Marks et al. Marks et al. (1991) Eur. J. Immunol. 21:985-991.

FIG. 8 illustrates an example of the method for constructing a library of fully human antibody sequences. The library construction is directed by essential antigen recognition segments (e.g., $V_H$) of a non-human antibody. According to this method, the process of humanizing a non-human antibody involves two steps of sequential humanization and library screening.

In the first step, the light chain of a non-human antibody is humanized. A library of chimeric antibody sequences is constructed with a bias toward a non-human $V_H$. As illustrated in FIG. 8, $V_H$ of the non-human antibody to be humanized is linked to the human constant domain 1 of the heavy chain, CH1, to form a chimeric antibody heavy chain. A library of human Vλ and Vκ (or CDRS) is linked to the human constant domain of the light chain, CL, in a yeast two-hybrid vector. This library of human antibody light chain sequences can be expressed to generate a library of chimeric Fabs by assembling with the chimeric heavy chain expressed from a separate vector in yeast. Alternatively, the library of human antibody light chain and the chimeric heavy chain may be expressed from separate expression cassettes in the same yeast vector. The assembly of these two chains may be facilitated by using "zipper" domains such as the Jun/Fos pair that are fused to the terminus of the heavy chain and light chain, respectively. The assembly of antibody fragments by zipper domains is described in details in Section 2 below.

As also illustrated in FIG. 8, the library of chimeric antibody is screened in a yeast two hybrid system against the original antigen against which the non-human antibody is elicited. The selected chimeric antibody is a chimeric Fab with non-human $V_H$ and the rest of human origin.

Second, the chimeric heavy chain in the selected chimeric antibody is humanized to form a fully human Fab with a human light chain. As illustrated in FIG. 8, a library of human $V_H$ (or CDRs) is linked to the human constant domain 1 of the heavy chain, CH1, in the yeast two-hybrid vector. The light chain of the selected chimeric antibody from the first step is expressed from a separate expression cassette and form a library of fully human Fabs by assembling with the library of human heavy chains ($V_H$+$C_H$1). This library of fully human Fabs is again subjected to a yeast two-hybrid screening against the The fully human Fab selected may be further linked to $C_H2$ and $C_H3$ at the C-terminus of the $C_H1$ domain, thereby resulting in a full length, fully human antibody.

2. Screening the Library of Humanized Antibodies in Yeast

1) Yeast Expression Vector

The library of humanized antibody sequences produced above can be cloned into a yeast expression vector for expression and screening in yeast.

The yeast expression vector is based on a yeast plasmid, especially one from *Saccharomyces cerevisiae*. After transformation of yeast cells, the exogenous DNA encoding humanized sequences are uptaken by the cells and subsequently expressed by the transformed cells.

More preferably, the expression vector may be a yeast-bacteria shuttle vector which can be propagated in either *Escherichia coli* or yeast Struhl, et al. (1979) Proc. Natl. Acad. Sci. 76:1035-1039. The inclusion of *E. coli* plasmid DNA sequences, such as pBR322, facilitates the quantitative preparation of vector DNA in *E. coli*, and thus the efficient transformation of yeast.

The types of yeast plasmid vector that may serve as the shuttle may be a replicating vector or an integrating vector. A replicating vector is yeast vector that is capable of mediating its own maintenance, independent of the chromosomal DNA of yeast, by virtue of the presence of a functional origin of DNA replication. An integrating vector relies upon recombination with the chromosomal DNA to facilitate replication and thus the continued maintenance of the recombinant DNA in the host cell. A replicating vector may be a 2μ-based plasmid vector in which the origin of DNA replication is derived from the endogenous 2μ plasmid of yeast. Alternatively, the replicating vector may be an autonomously replicating (ARS) vector, in which the "apparent" origin of replication is derived from the chromosomal DNA of yeast. Optionally, the replicating vector may be a centromeric (CEN) plasmid which carries in addition to one of the above origins of DNA replication a sequence of yeast chromosomal DNA known to harbor a centromere.

The vectors may be transformed into yeast cells in a closed circular form or in a linear form. Transformation of yeast by integrating vectors, although with inheritable stability, may not be efficient when the vector is in a close circular form (e.g. 1-10 transformants per ug of DNA). Linearized vectors, with free ends located in DNA sequences homologous with yeast chromosomal DNA, transforms yeast with higher efficiency (100-1000 fold) and the transforming DNA is generally found integrated in sequences homologous to the site of cleavage. Thus, by cleaving the vector DNA with a suitable restriction endonuclease, it is possible to increase the efficiency of transformation and target the site of chromosomal integration. Integrative transformation may be applicable to the genetic modification of brewing yeast, providing that the efficiency of transformation is sufficiently high and the target DNA sequence for integration is within a region that does not disrupt genes essential to the metabolism of the host cell.

ARS plasmids, which have a high copy number (approximately 20-50 copies per cell) (Hyman et al., 1982), tend to be the most unstable, and are lost at a frequency greater than 10% per generation. However, the stability of ARS plasmids can be enhanced by the attachment of a centromere; centromeric plasmids are present at 1 or 2 copies per cell and are lost at only approximately 1% per generation.

In a preferred embodiment, the expression vector for expressing the library of humanized antibody is based on the 2μ plasmid. The 2μ plasmid is known to be nuclear in cellular location, but is inherited in a non-Mendelian fashion. Cells that lost the 2μ plasmid have been shown to arise from haploid yeast populations having an average copy number of 50 copies of the 2μ plasmid per cell at a rate of between 0.001% and 0.01% of the cells per generation. Futcher & Cox (1983) J. Bacteriol. 154:612. Analysis of different strains of *S. cerevisiae* has shown that the plasmid is present in most strains of yeast including brewing yeast. The 2μ plasmid is ubiquitous and possesses a high degree of inheritable stability in nature.

The 2μ plasmid harbors a unique bidirectional origin of DNA replication which is an essential component of all 2μ-based vectors. The plasmid contains four genes, REP1, REP2, REP3 and FLP which are required for the stable maintenance of high plasmid copy number per cell. Jaysram et al. (1983) Cell 34:95. The REP1 and REP2 genes encode trans-acting proteins which are believed to function in concert by interacting with the REP3 locus to ensure the stable partitioning of the plasmid at cell division. In this respect, the REP3 gene behaves as a cis acting locus which effects the stable segregation of the plasmid, and is phenotypically analogous to a chromosomal centromere. An important feature of the 2µ plasmid is the presence of two inverted DNA sequence repeats (each 559 base-pairs in length) which separate the circular molecule into two unique regions. Intramolecular recombination between the inverted repeat sequences results in the inversion of one unique region relative to the other and the production in vivo of a mixed population of two structural isomers of the plasmid, designated A and B. Recombination between the two inverted repeats is mediated by the protein product of a gene called the FLP gene, and the FLP protein is capable of mediating high frequency recombination within the inverted repeat region. This site specific recombination event is believed to provide a mechanism which ensures the amplification of plasmid copy number. Murray et al. (1987) EMBO J. 6:4205.

The expression vector may also contain an *Escherichia coli* origin of replication and *E. coil* antibiotic resistance genes for propagation and antibiotic selection in bacteria. Many *E. coli* origins are known, including ColE1, pMB1 and pBR322, The ColE origin of replication is preferably used in this invention. Many *E. coli* drug resistance genes are known, including the ampicillin resistance gene, the chloramphenoicol resistance gene and the tetracycline resistance gene. In one particular embodiment, the ampicillin resistance gene is used in the vector.

The transformants that carry the humanized antibody sequences may be selected by using various selection schemes. The selection is typically achieved by incorporating within the vector DNA a gene with a discernible phenotype. In the case of vectors used to transform laboratory yeast, prototrophic genes, such as LEU2, URA3 or TRP1, are usually used to complement auxotrophic lesions in the host. However, in order to transform brewing yeast and other industrial yeasts, which are frequently polyploid and do not display auxotrophic requirements, it is necessary to utilize a selection system based upon a dominant selectable gene. In this respect replicating transformants carrying 2µ-based plasmid vectors may be selected based on expression of marker genes which mediate resistance to: antibiotics such as G418, hygromycin B and chloramphenicol, or otherwise toxic materials such as the herbicide sulfometuron methyl, compactin and copper.

2) Homologous Recombination in Yeast

The library of yeast expression vectors described above can be constructed using a variety of recombinant DNA techniques. In a preferred embodiment, the library of yeast expression vectors containing a library of humanized antibody sequences are constructed by exploiting the inherent ability of yeast cells to facilitate homologous recombination at an extremely high efficiency. The mechanism of homologous recombination in yeast and its applications is briefly described below.

Yeast *Saccharomyces cerevisiae* has an inherited genetic machinery to carry out efficient homologous recombination in the cell. This mechanism is believed to benefit the yeast cells for chromosome repair purpose and traditionally also called gap repair or gap filling. By this mechanism of efficient gap filling, mutations can be introduced into specific loci of the yeast genome. For example, a vector carrying the mutant gene contains two sequence segments that are homologous to the 5' and 3' open reading frame (ORF) sequences of the gene that is intended to be interrupted or mutated. The plasmid also contains a positive selection marker such as a nutritional enzyme allele, such as ura3, or an antibiotic resistant marker such as Geneticine (g418) that are flanked by the two homologous segments. This plasmid is linearized and transformed into the yeast cells. Through homologous recombination between the plasmid and the yeast genome at the two homologous recombination sites, a reciprocal exchange of the DNA content occurs between the wild type gene in the yeast genome and the mutant gene (including the selection marker gene) that are flanked by the two homologous sequence segments. By selecting for the positive nutritional marker, surviving yeast cells will loose the original wild type gene and will adopt the mutant gene. Pearson B M, Hernando Y, and Schweizer M, (1998) Yeast 14: 391-399. This mechanism has also been used to make systematic mutations in all 6,000 yeast genes or ORFs for functional genomics studies. Because the exchange is reciprocal, similar approach has been used successfully for cloning yeast genomic fragments into plasmid vector. Iwasaki T, Shirahige K, Yoshikawa H, and Ogasawara N, Gene 1991, 109 (1): 81-87.

By using homologous recombination in yeast, gene fragments or synthetic oligonucleotides can also be cloned into a plasmid vector without a ligation step. In this application, a targeted gene fragment is usually obtained by PCR amplification (or by using the conventional restriction digestion out of an original cloning vector). Two short fragment sequences that are homologous to the plasmid vector are added to the 5' and 3' of the target gene fragment in the PCR amplification. This can be achieved by using a pair of PCR primers that incorporate the added sequences. The plasmid vector typically includes a positive selection marker such as nutritional enzyme allele such as ura3, or an antibiotic resistant marker such as geneticin (g418). The plasmid vector is linearized by a unique restriction cut in between the sequence homologies that are shared with the PCR-amplified target, thereby creating an artificial gap at the cleavage site. The linearized plasmid vector and the target gene fragment flanked by sequences homologous to the plasmid vector are co-transformed into a yeast host strain. The yeast recognizes the two stretches of sequence homologies between the vector and target fragment, and facilitates a reciprocal exchange of DNA contents through homologous recombination at the gap. As the consequence, the target fragment is automatically inserted into the vector without ligation in vitro.

There are a few factors that may influence the efficiency of homologous recombination in yeast. The efficiency of the gap repair is correlated with the length of the homologous sequences flanking both the linearized vector and the targeted gene. Preferably, a minimum of 30 base pairs may be required for the length of the homologous sequence, and 80 base pairs may give a near-optimized result. Hua, S. B. et al. (1997) "Minimum length of sequence homology required for in vitro cloning by homologous recombination in yeast" Plasmid 38:91-96. In addition, the reciprocal exchange between the vector and gene fragment is strictly sequence-dependent, i.e. not causing frame shift in this type of cloning. Therefore, such a unique characteristic of the gap-repair cloning assures insertion of gene fragments with both high efficiency and precision. The high efficiency makes it possible to clone two or three targeted gene fragments simultaneously into the same vector in one transformation attempt. Raymond K., Pownder T. A., and Sexson S. L., (1999) Biotechniques 26: 134-141. The nature of precision sequence conservation through homologous recombination makes it possible to clone targeted genes in question into expression or fusion vectors for direct function examinations. So far many functional or diagnostic applications have been reported using homologous recombination. El-Deiry W. W., et al., Nature Genetics1: 45-49, 1992 (for p53), and Ishioka C., et al., PNAS, 94: 2449-2453, 1997 (for BRCA1 and APC).

A library of gene fragments may also be constructed in yeast by using homologous recombination. For example, a human brain cDNA library can be constructed as a two-hybrid fusion library in vector pJG4-5. Guidotti E., and Zervos A. S. (1999) "In vivo construction of cDNA library for use in the yeast two-hybrid systems" Yeast 15:715-720. It has been reported that a total of 6,000 pairs of PCR primers were used for amplification of 6,000 known yeast ORFs for a study of total yeast genomic protein interaction. Hudson, J. Jr, et al. (1997) Genome Res. 7:1169-1173. Uetz et al. conducted a comprehensive analysis of protein-protein interactions in Saccharomyces cerevisiae. Uetz et al. (2000) Nature 403:623-627. The protein-protein interaction map of the budding yeast was studied by using a comprehensive system to examine two-hybrid interactions in all possible combinations between the yeast proteins. Ito et al. (2000) Proc. Natl. Acad. Sci. USA. 97:1143-1147. The genomic protein linkage map of Vaccinia virus was studied by McCraith S., Holtzman T., Moss B., and Fields, S. (2000) Proc. Natl. Acad. Sci. USA 97: 4879-4884.

In a preferred embodiment, the library of humanized antibody sequences constructed in Section 1 is introduced into a yeast expression vector by homologous recombination performed directly in yeast cells. The expression vector containing an AD domain may be any vector engineered to carry the coding sequence of the AD domain.

According to this embodiment, the expression vector is preferably a yeast vector such as pGAD10 (Feiloter et al. (1994) "Construction of an improved host strain for two hybrid screening" Nucleic Acids Res. 22: 1502-1503), pACT2 (Harper et al (1993) "The p21 Cdk-interacting protein Cip1 is a protein inhibitor of G1 cyclin-dependent kinase" Cell 75:805-816), and pGADT7 ( "Matchmaker Gal4 two hybrid system 3 and libraries user manual" (1999), Clontech PT3247-1, supplied by Clontech, Palo Alto, Calif.).

Also according to this embodiment, the flanking sequences that are added to the 5' and 3'-terminus of scFv sequences (or each of the heavy chain and light chain for the double chain approach) in the library. The flanking sequence is preferably between about 30-120 bp in length, more preferably between about 40-90 bp in length, and most preferably between about 45-55 bp in length.

When the library of humanized antibody sequences is inserted into an expression vector containing an AD domain, it is preferred that the reading frame of the humanized antibody sequence is conserved with upstream AD reading frame.

Depending on the cloning expression vector used, additional features such as affinity tags and unique restriction enzyme recognition sites may be added to the expression for the convenience of detection and purification of the inserted humanized antibody sequences. Examples of affinity tags include, but are not limited to, a polyhistidine tract, polyarginine, glutathione-S-transferase (GST), maltose binding protein (MBP), a portion of staphylococcal protein A (SPA), and various immunoaffinity tags (e.g. protein A) and epitope tags such as those recognized by the EE (Glu-Glu) antipeptide antibodies.

Optionally, expression of the library of humanized antibody sequences may be under the transcriptional control of an inducible promoter. One example of such an expression vector is available from Clontech, pBRIDGE® (catalog No. 6184-1). The expression vector, pBRIDGE®, contains one expression unit that controls expression of a Gal 4 BD domain and another expression unit that includes an inducible promoter Pmat25. Tirode, E. et al. (1997) J. Biol. Chem. 272:22995-22999.

The linearized vector DNA may be mixed with equal or excess amount of the inserts of humanized antibody sequences generated in Section 1. The linearized vector DNA and the inserts are co-transformed into host cells, such as competent yeast cells. Recombinant clones may be selected based on survival of cells in a nutritional selection medium or based on other phenotypic markers. Either the linearized vector or the insert alone may be used as a control for determining the efficiency of recombination and transformation.

Other homologous recombination systems may be used to generate the library of expression vectors of the present invention. For example, the recombination between the library of humanized antibody sequences and the recipient expression vector may be facilitated by site-specific recombination.

The site-specific recombination employs a site-specific recombinase, an enzyme which catalyzes the exchange of DNA segments at specific recombination sites. Site-specific recombinases present in some viruses and bacteria, and have been characterized to have both endonuclease and ligase properties. These recombinases, along with associated proteins in some cases, recognize specific sequences of bases in DNA and exchange the DNA segments flanking those segments. Landy, A. (1993) Current Opinion in Biotechnology 3:699-707.

A typical site-specific recombinase is CRE recombinase. CRE is a 38-kDa product of the cre (cyclization recombination) gene of bacteriophage P1 and is a site-specific DNA recombinase of the Int family. Sternberg, N. et al. (1986) J. Mol. Biol. 187: 197-212. CRE recognizes a 34-bp site on the P1 genome called loxp (locus of X-over of P1) and efficiently catalyzes reciprocal conservative DNA recombination between pairs of loxp sites. The loxp site [SEQ ID NO: 1] consists of two 13-bp inverted repeats flanking an 8-bp nonpalindromic core region. CRE-mediated recombination between two directly repeated loxp sites results in excision of DNA between them as a covalently closed circle. Cre-mediated recombination between pairs of loxp sites in inverted orientation will result in inversion of the intervening DNA rather than excision. Breaking and joining of DNA is confined to discrete positions within the core region and proceeds on strand at a time by way of transient phophotyrosine DNA-protein linkage with the enzyme.

The CRE recombinase also recognizes a number of variant or mutant lox sites relative to the loxp sequence. Examples of these Cre recombination sites include, but are not limited to, the loxB, loxL and loxR sites which are found in the E. coli chromosome. Hoess et al. (1986) Nucleic Acid Res. 14:2287-2300. Other variant lox sites include, but are not limited to, loxB, loxL, loxR, loxP3, loxP23, loxΔ86, loxΔ117, loxP511, and loxC2.

Examples of the non-CRE recombinases include, but are not limited to, site-specific recombinases include: att sites recognized by the Int recombinase of bacteriophage λ e.g. att1, att2, att3, attP, attB, attL, and attR) the FRT sites recognized by FLP recombinase of the 2pi plasmid of Saccharomyces cerevisiae, the recombination sites recognized by the resolvase family, and the recombination site recognized by transposase of Bacillus thruingiensis.

Subsequent analysis may also be carried out to determine the efficiency of homologous recombination that results in correct insertion of the humanized antibody sequences into the expression vector. For example, PCR amplification of the inserts of the humanized antibody sequences directly from the selected yeast clone may reveal how many clones are recombinant. Libraries with minimum of 90% recombinant clones are preferred. The same PCR amplification of selected clones may also reveal the insert size. Although a small fraction of the library may contain double or triple inserts, the majority (>90%) is preferably to have a single insert with the expected size.

To verify sequence diversity of the inserts in the selected clones, PCR amplification product with the correct size of insert may be fingerprinted with frequent digesting restriction enzymes. From a gel electrophoresis pattern, it may be determined whether the clones analyzed are of the same identity or of the distinct or diversified identity. The PCR products may also be sequenced directly to reveal the identity of inserts and the fidelity of the cloning procedure and to prove the independence and diversity of the clones.

3) Yeast Two-Hybrid Screening

The present invention also provides methods for screening a library of humanized antibody against a target antigen. The target antigen may be the original antigen against which the non-human antibody is elicited. In this case, the humanized antibody selected is truly "humanized" from the original non-human antibody. Alternatively, the target antigen against which the library of humanized antibody is screened may be an antigen different from the original antigen. For example, the antigen may be an isoform in the same family of proteins as the original antigen. Through this process, a humanized antibody with high binding affinity to a new target antigen can be selected without first obtaining a non-human antibody against this new target antigen.

The library of humanized antibody is screened against the target antigen in a yeast two-hybrid system. The two-hybrid system is a selection scheme designed to screen for polypeptide sequences which bind to a predetermined polypeptide sequence present in a fusion protein. Chien et al. (1991) Proc. Natl. Acad. Sci. (USA) 88: 9578). This approach identifies protein-protein interactions in vivo through reconstitution of a transcriptional activator. Fields and Song (1989) Nature 340: 245), the yeast Gal 4 transcription protein. The method is based on the properties of the yeast Gal 4 protein, which consists of separable domains responsible for DNA-binding and transcriptional activation. Polynucleotides encoding two hybrid proteins, one consisting of the yeast Gal 4 DNA-binding domain (BD) fused to a polypeptide sequence of a known protein and the other consisting of the Gal4 activation domain (AD) fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacZ, HIS3) which is operably linked to a Gal4 binding site.

Typically, the two-hybrid method is used to identify novel polypeptide sequences which interact with a known protein. Silver and Hunt (1993) Mol. Biol. Rep. 17: 155; Durfee et al. (1993) Genes Devel. 7; 555; Yang et al. (1992) Science 257: 680; Luban et al. (1993) Cell 73: 1067; Hardy et al. (1992) Genes Devel. 6; 801; Bartel et al. (1993) Biotechniques 14: 920; and Vojtek et al. (1993) Cell 74: 205. The two-hybrid system was used to detect interactions between three specific single-chain variable fragments (scFv) and a specific antigen. De Jaeger et al. (2000) FEBS Lett. 467: 316-320. The two-hybrid system was also used to screen against cell surface proteins or receptors such as receptors of hematopoietic super family in yeast. Ozenberger, B. A., and Young, K. H. (1995) "Functional interaction of ligands and receptors of hematopoietic superfamily in yeast" Mol Endocrinol. 9:1321-1329.

Variations of the two-hybrid method have been used to identify mutations of a known protein that affect its binding to a second known protein Li and Fields (1993) FASEB J. 7: 957; Lalo et al. (1993) Proc. Natl. Acad. Sci. (USA) 90: 5524; Jackson et al. (1993) Mol. Cell. Biol. 13; 2899; and Madura et al. (1993) J. Biol. Chem. 268: 12046.

Two-hybrid systems have also been used to identify interacting structural domains of two known proteins or domains responsible for oligomerization of a single protein. Bardwell et al. (1993) Med. Microbiol. 8: 1177; Chalraborty et al. (1992) J. Biol. Chem. 267: 17498; Staudinger et al. (1993) J. Biol. Chem. 268: 4608; and Milne G T; Weaver D T (1993) Genes Devel. 7; 1755; Iwabuchi et al. (1993) Oncogene 8; 1693; Bogerd et al. (1993) J. Virol. 67: 5030).

Variations of two-hybrid systems have been used to study the in vivo activity of a proteolytic enzyme. Dasmahapatra et al. (1992) Proc. Natl. Acad. Sci. (USA) 89: 4159. Alternatively, an $E.$ $coli$/BCCP interactive screening system was used to identify interacting protein sequences (i.e., protein sequences which heterodimerize or form higher order heteromultimers). Germino et al. (1993) Proc. Natl. Acad. Sci. (U.S.A.) 90: 933; and Guarente L (1993) Proc. Natl. Acad. Sci. (U.S.A.) 90: 1639.

Typically, selection of binding protein using a two-hybrid method relies upon a positive association between two Gal4 fusion proteins, thereby reconstituting a functional Gal4 transcriptional activator which then induces transcription of a reporter gene operably linked to a Gal4 binding site. Transcription of the reporter gene produces a positive readout, typically manifested either (1) as an enzyme activity (e.g., β-galactosidase) that can be identified by a colorimetric enzyme assay or (2) as enhanced cell growth on a defined medium (e.g., HIS3 and Ade 2). Thus, the method is suited for identifying a positive interaction of polypeptide sequences, such as antibody-antigen interactions.

False positives clones that indicate activation of the reporter gene irrespective of the specific interaction between the two hybrid proteins, may arise in the two-hybrid screening. Various procedures have developed to reduce and eliminate the false positive clones from the final positives. For example, 1) prescreening the clones that contains the target vector and shows positive in the absence of the two-hybrid partner (Bartel, P. L., et al. (1993) "Elimination of false positives that arise in using the two-hybrid system" BioTechniques 14:920-924); 2) by using multiple reporters such as His3, β-galactosidase, and Ade2 (James, P. et al. (1996) "Genomic libraries and a host strain designed for highly efficient two-hybrid selection in yeast" Genetics 144:1425-1436); 3) by using multiple reporters each of which is under different GAL 4-responsive promoters such as those in yeast strain Y190 where each of the His 3 and β-Gal reporters is under the control of a different promoter Gal 1 or Gal 10, but both response to Gal 4 signaling (Durfee, T., et al (1993) "The retinoblastoma protein associates with the protein phosphatase type 1 catalytic subunit" Genes Devel. 7:555-569); and 4) by post-screening assays such as testing isolates with target consisting of GAL 4-BD alone.

In addition, the false positive clones may also be eliminated by using unrelated targets to confirm specificity. This is a standard control procedure in the two-hybrid system which can be performed after the library isolate is confirmed by the above-described 1)-4) procedures. Typically, the library clones are confirmed by co-transforming the initially isolated library clones back into the yeast reporter strain with one or more control targets unrelated to the target used in the original screening. Selection is conducted to eliminate those library clones that show positive activation of the reporter gene and thus indicate non-specfic interactions with multiple, related proteins.

The present invention provides efficient methods for screening a library of humanized antibody contained in a library of expression vectors for their affinity binding to a specific antigen.

According to the present invention, the method comprises:

expressing a library of humanized antibodies in yeast cells;

expressing a specific target protein in the yeast cells expressing the humanized antibodies; and selecting those yeast cells in which a reporter gene is expressed, the expression of the reporter gene being activated by binding of the humanized antibody to the target protein.

According to the method, the diversity of the library of humanized antibody is preferably between $10^2$-$10^8$, more preferably between $10^4$-$10^8$, and most preferably between $10^5$-$10^8$.

According to the embodiment, the target protein is expressed as a fusion and screened against the library of humanized antibody. Thus, the step of expressing the library of humanized antibody may include transforming a library of expression vectors encoding the library of humanized antibody into the yeast cells which contain a reporter construct comprising the reporter gene. The report gene expression is under transcriptional control of a transcription activator comprising an activation domain and a DNA binding domain.

Each of the expression vectors comprises a humanized antibody sequence (e.g., scFv, heavy chain or light chain) fused with either the activation domain or the DNA binding domain of the transcription activator.

Optionally, the step of expressing the target protein includes transforming a target expression vector into the yeast cells simultaneously or sequentially with the library of humanized expression vectors encoding humanized antibody. The target expression vector comprises a second transcription sequence encoding either the activation domain AD or the DNA binding domain BD of the transcription activator which is not expressed by the library of humanized antibody expression vectors; and a target sequence encoding the target protein or peptide.

FIG. 9 illustrates a flow diagram of a preferred embodiment of the above described method. As illustrated in FIG. 9, the sequence library containing scFv is fused with an AD domain upstream, the AD-scFv vectors. The coding sequence of the target protein (labeled as "Target") is contained in another expression vector and fused with a BD domain, forming the BD-Target vector.

The AD-scFv vector and the BD-Target vector may be co-transformed into a yeast cell by using method known in the art. Gietz, D. et al. (1992) "Improved method for high efficiency transformation of intact yeast cells" Nucleic Acids Res. 20:1425. The construct carrying the specific DNA binding site and the reporter gene (labeled as "Reporter") may be stably integrated into the genome of the host cell or transiently transformed into the host cell. Upon expression of the sequences in the expression vectors, the library of protein complexes comprising AD-scFv, undergo protein folding in the host cell and adopt various conformations. Some of the AD-scFv fusion protein complexes may bind to the Target protein expressed by the BD-Target vector in the host cell, thereby bringing the AD and BD domains to a close proximity in the promoter region (i.e., the specific DNA binding site) of the reporter construct and thus reconstituting a functional transcription activator composed of the AD and BD domains. As a result, the AD activates the transcription of the reporter gene downstream from the specific DNA binding site, resulting in expression of the reporter gene, such as the lacZ reporter gene. Clones showing the phenotype of the reporter gene expression are selected, and the AD-scFv vectors are isolated. The coding sequences for scFv are identified and characterized.

Alternatively, the steps of expressing the library of humanized antibody and expressing the target fusion protein includes causing mating between first and second populations of haploid yeast cells of opposite mating types.

The first population of haploid yeast cells comprises a library of expression vectors encoding the library of humanized antibody. Each of the expression vector comprises a first transcription sequence encoding either the activation domain AD or the DNA binding domain BD of the transcription activator and a scFv encoding an humanized antibody.

The second population of haploid yeast cells comprises a target expression vector. The target expression vector comprises a second transcription sequence encoding either the activation domain AD or the DNA binding domain BD of the transcription activator which is not expressed by the library of tester expression vectors; and a target sequence encoding the target protein or peptide. Either the first or second population of haploid yeast cells comprises a reporter construct comprising the reporter gene whose expression is under transcriptional control of the transcription activator.

In this method, the haploid yeast cells of opposite mating types may preferably be α and a type strains of yeast. The mating between the first and second populations of haploid yeast cells of α and a-type strains may be conducted in a rich nutritional culture medium.

Figure 10:
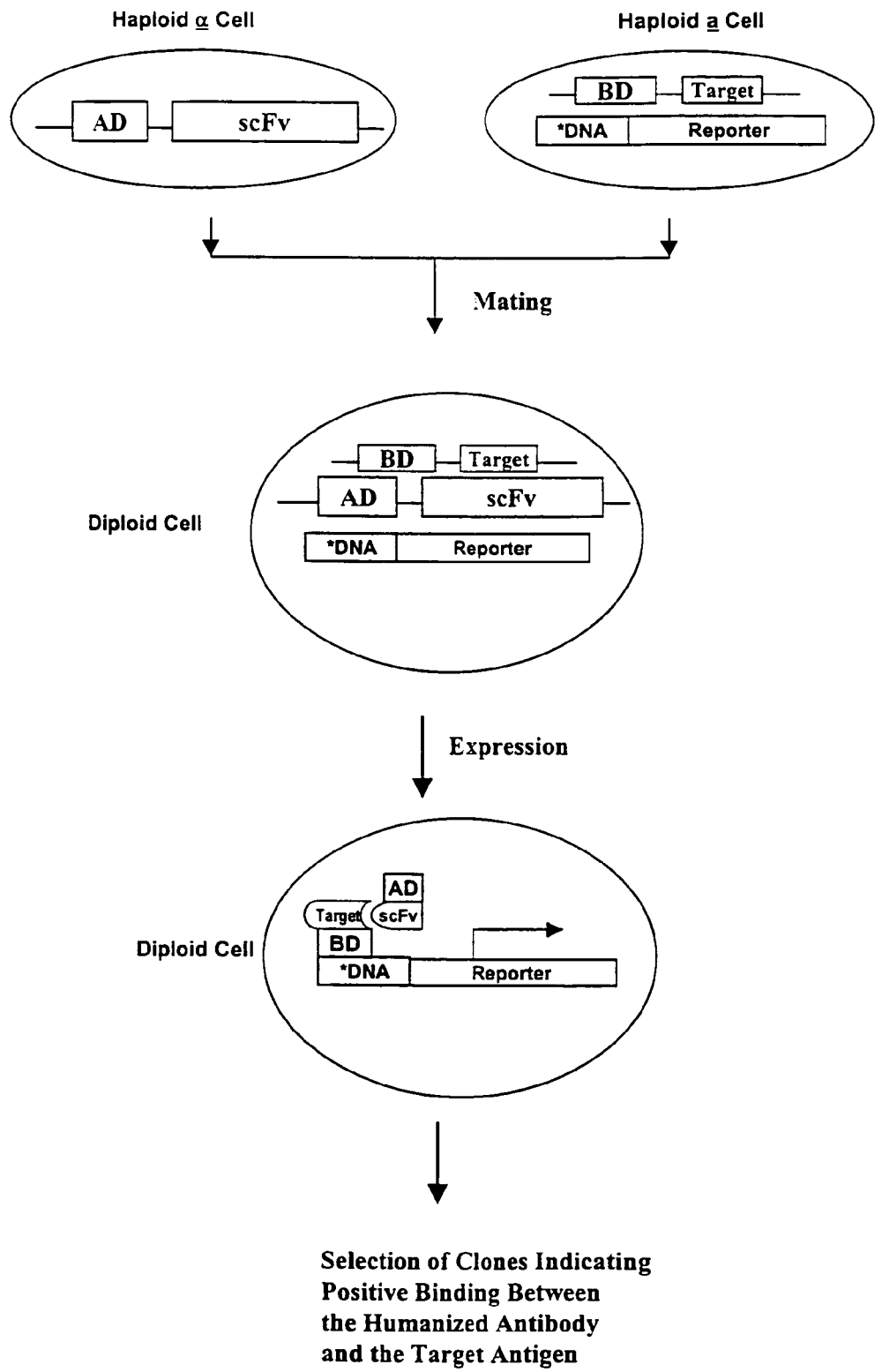
FIG. 10 illustrates an embodiment of the method for selecting humanized single-chain antibody (scFv) against a target protein in a two-hybrid system where the expression vectors carrying the AD and BD domains are introduced into diploid yeast cells via mating between two haploid yeast strains of opposite mating types.

FIG. 10 illustrates a flow diagram of a preferred embodiment of the above described method. As illustrated in FIG. 10, the sequence library containing a scFv fused with an AD domain upstream, the AD-scFv vectors. The library of the AD-scFv vectors are transformed into haploid yeast cells such as the a type strain of yeast.

The coding sequence of the target protein (labeled as "Target") is contained in another expression vector and fused with a BD domain, forming the BD-Target vector. The BD-Target vector is transformed into haploid cells of opposite mating type of the haploid cells containing the AD-scFv vectors, such as the α type strain of yeast. The construct carrying the specific DNA binding site and the reporter gene (labeled as "Reporter") may be transformed into the haploid cells of either the type a or type α strain of yeast.

The haploid cells of the type a and type α strains of yeast are mated under suitable conditions such as low speed of shaking in liquid culture, physical contact in solid medium culture, and rich medium such as YPD. Bendixen, C. et al. (1994) "A yeast mating-selection scheme for detection of protein-protein interactions", Nucleic Acids Res. 22: 1778-1779. Finley, Jr., R. L. & Brent, R. (1994) "Interaction mating reveals lineary and ternery connections between Drosophila cell cycle regulators", Proc. Natl. Acad. Sci. USA, 91:12980-12984. As a result, the AD-scFv, the BD- Target expression vectors and the Reporter construct are taken into the parental diploid cells of the a and type α strain of haploid yeast cells.

Upon expression of the sequences in the expression vectors in the parental diploid cells, the library of protein complexs formed between AD-scFv, labeled as the AD-scFv fusion protein, undergo protein folding in the host cell and adopt various conformations. Some of the AD-scFv protein complexes may bind to the Target protein expressed by the BD-Target vector in the parental diploid cell, thereby bringing the AD and BD domains to a close proximity in the promoter region (i.e., the specific DNA binding site) of the reporter construct and thus reconstituting a functional transcription activator composed of the AD and BD domains. As a result, the AD activates the transcription of the reporter gene downstream from the specific DNA binding site, resulting in expression of the reporter gene, such as the lacZ reporter gene. Clones showing the phenotype of the reporter gene expression are selected, and the AD-scFv vectors are isolated. The coding sequences for scFv are identified and characterized.

A wide variety of reporter genes may be used in the present invention. Examples of proteins encoded by reporter genes include, but are not limited to, easily assayed enzymes such as β-galactosidase, α-galactosidase, luciferase, β-glucuronidase, chloramphenicol acetyl transferase (CAT), secreted embryonic alkaline phosphatase (SEAP), fluorescent proteins such as green fluorescent protein (GFP), enhanced blue fluorescent protein (EBFP), enhanced yellow fluorescent protein (EYFP) and enhanced cyan fluorescent protein (ECFP); and proteins for which immunoassays are readily available such as hormones and cytokines. The expression of these reporter genes can also be monitored by measuring levels of mRNA transcribed from these genes.

When the screening of the humanized antibody library is conducted in yeast cells, certain reporter(s) are of nutritional reporter which allows the yeast to grow on the specific selection medium plate. This is a very powerful screening process, as has been shown by many published papers. Examples of the nutritional reporter include, but are not limited to, His3, Ade2, Leu2, Ura3, Trp1 and Lys2. The His3 reporter is described in Bartel, P. L. et al. (1993) "Using the two-hybrid system to detect protein-protein interactions", in Cellular interactions in Development: A practical approach, ed. Hastley, D. A., Oxford Press, pages 153-179. The Ade2 reporter is described in Jarves, P. et al. (1996) "Genomic libraries and a host strain designed for highly efficient two-hybrid selection in yeast" Genetics 144:1425-1436.

For example, the library of humanized antibody expression vectors may be transformed into haploid cells of the α mating type of yeast strain. The plasmid containing the sequence encoding the target protein fused with a BD domain is transformed into haploid cells of the a mating type of yeast strain.

Equal volume of AD-scFv library-containing yeast stain (α-type) and the BD-target-containing yeast strain (a-type) are inoculated into selection liquid medium and incubated separately first. These two cultures are then mixed and allowed to grow in rich medium such as 1xYPD and 2xYPD. Under the rich nutritional culture condition, the two haploid yeast strains will mate and form diploid cells. At the end of this mating process, these yeast cells are plated into selection plates. A multiple-marker selection scheme may be used to select yeast clones that show positive interaction between the antibodies in the library and the target. For example, a scheme of SD/-Leu-Trp-His-Ade may be used. The first two selections (Leu-Trp) are for markers (Leu and Trp) expressed from the AD-Antibody library and the BD-Target vector, respectively. Through this dual-marker selection, diploid cells retaining both BD and AD vectors in the same yeast cells are selected. The latter two markers, His-Ade, are used to screen for those clones that express the reporter gene from parental strain, presumably due to affinity binding between the antibodies in the library and the target.

After the screening by co-transformation, or by mating screening as described above, the putative interaction between the target antigen with the humanized antibody encoded by the library clone isolates can be further tested and confirmed in vitro or in vivo.

In vitro binding assays may be used to confirm the positive interaction between the humanized expressed by the clone isolate and the target protein or peptide (e.g. the target antigen). For example, the in vitro binding assay may be a "pull-down" method, such as using GST (glutathione S-transferase)-fused target antigen as matrix-binding protein, and with in vitro expressed library clone isolate that are labeled with a radioactive or non-radioactive group. While the target antigen is bound to the matrix through GST affinity substrate (glutathione-agarose), the library clone isolate will also bind to the matrix through its affinity with the target antigen. The in vitro binding assay may also be a co-immuno-precipitation (Co-IP) method using two affinity tag antibodies. In this assay, both the target antigen and the library clone isolate are in vitro expressed fused with peptide tags, such as HA (haemaglutinin A) or Myc tags. The gene probe is first immuno-precipitated with an antibody against the affinity peptide tag (such as HA) that the target gene probe is fused with. Then the second antibody against a different affinity tag (such as Myc) that is fused with the library clone isolate is used for reprobing the precipitate.

In vivo assays may also be used to confirm the positive interaction between the humanized antibody expressed by the clone isolate and the target antigen. For example, a mammalian two-hybrid system may serve as a reliable verification system for the yeast two-hybrid library screening. In this system, the target antigen and the library clone are fused with Gal 4 DNA-binding domain or a mammalian activation domain (such as VP-16) respectively. These two fusion proteins under control of a strong and constitutive mammalian promoter (such as CMV promoter) are introduced into mammalian cells by transfection along with a reporter responsive to Gal 4. The reporter can be CAT gene (chlorophenical acetate transferase) or other commonly used reporters. After 2-3 days of transfection, CAT assay or other standard assays will be performed to measure the strength of the reporter which is correlated with the strength of interaction between the target antigen and the library clone isolate.

According to the present invention, other yeast two-hybrid systems may be employed, including but not limited to SOS-RAS system (SRS), Ras recruitment system (RRS), and ubiquitin split system. Brachmann and Boeke (1997) "Tag games in yeast: the two-hybrid system and beyond" Current Opinion Biotech. 8:561-568. In these non-conventional yeast two-hybrid systems, the first or second polypeptide subunit may further comprise a signaling domain for screening the library of the protein complexes based these non-conventional two-hybrid methods. Examples of such signaling domain includes but are not limited to a Ras guanyl nucleotide exchange factor (e.g. human SOS factor), a membrane targeting signal such as a myristoylation sequence and farnesylation sequence, mammalian Ras lacking the carboxy-terminal domain (the CAAX box), and a ubiquitin sequence.

SRS and RRS systems are alternative two-hybrid systems for studying protein-protein interaction in cytoplasm. Both systems use a yeast strain with temperature-sensitive mutation in the cdc25 gene, the yeast homologue of human Sos (hSos). This protein, a guanyl nucleotide exchange factor, binds and activates Ras, that triggers the Ras signaling pathway. The mutation in the cdc25 protein is temperature sensitive; the cells can grow at 25° C. but not at 37° C. In the SRS system, this cdc25 mutation is complemented by the hSos gene product to allow growth at 37° C., providing that the hSos protein is localized to the membrane via a protein-protein interaction (Aronheim et al. 1997, Mol. Cel. Biol. 17:3094-3102). In the RRS system, the mutation is complemented by a mammalian activated Ras with its CAAX box at its carboxy terminus upon recruitment to the plasma membrane via protein-protein interaction (Broder et al, 1998, Current Biol. 8:1121-1124).

3. Screening of a Library of Humanized Antibody by Ribosome Display

The present invention also provides methods for screening a library of humanized antibody against a specific target antigen via ribosome display in vitro.

Ribosome display is a form of protein display for in vitro selection against a target ligand. In this system, mRNA encoding the tester protein (e.g. an antibody) and the translated tester protein are associated through the ribosome complex, also called an antibody-ribosome-mRNA (ARM) complex. He and Taussig (1997) Nucleic Acid Research 25:5132-5134. The principle behind this approach is that single chain antibody can be functionally produced in an in vitro translation system (e.g. rabbit reticulocyte lysate), and in the absence of a stop codon, individual nascent proteins remain associated with their corresponding mRNa as stable ternary polypeptide-ribosome-mRNA complexes in such a cell-free system.

Figure 11:
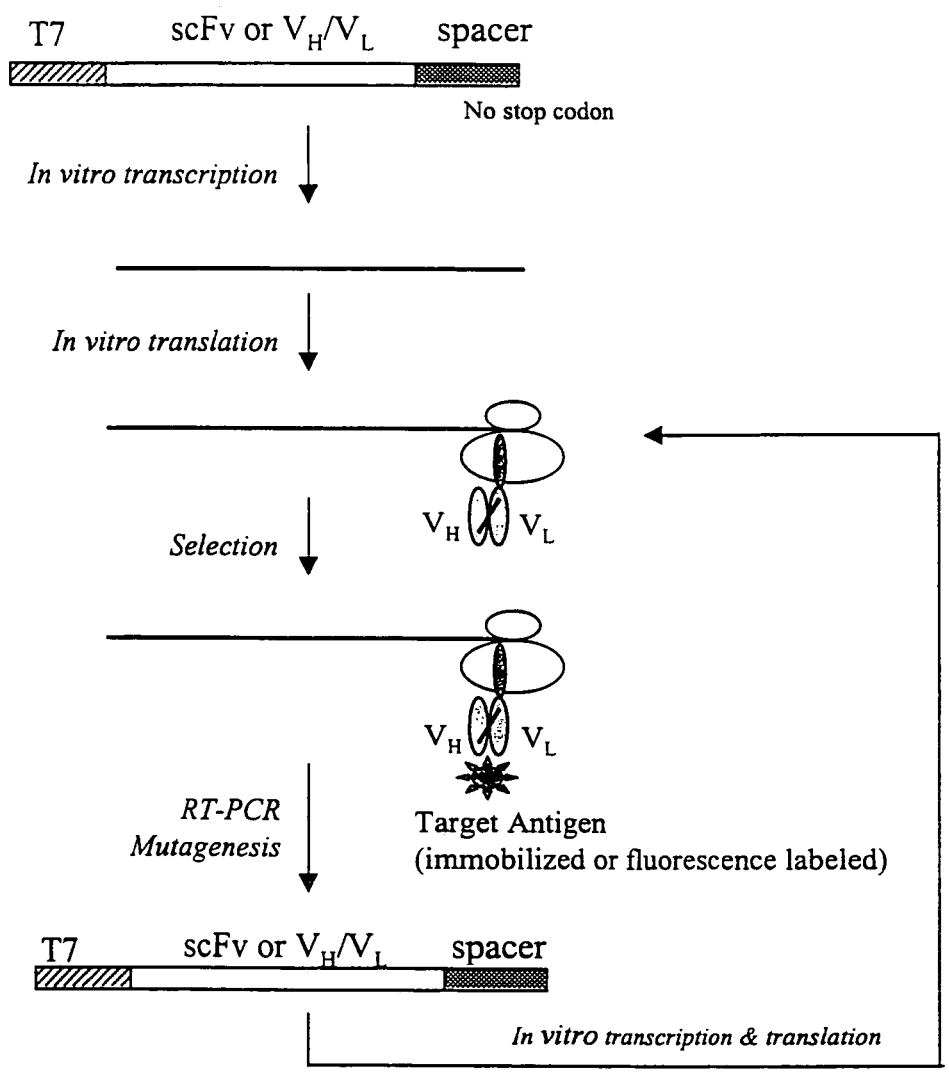
FIG. 11 illustrates an embodiment of the method for selecting humanized antibody against a target antigen through ribosome display.

FIG. 11 illustrates a method of the present invention used for screening the library of humanized antibody sequences constructed in Section 1 in the ARM system. As illustrated in FIG. 11, each member of the library of humanized antibody sequences for ribosome display includes a bacterial phage T7 promoter and protein synthesis initiation sequence attached to the 5' end of the cDNA encoding the antibody (e.g., scFv, $V_H$ or $V_L$) and no stop codon in the 3' end. Because the cDNA pool is depleted of the stop codon, when the mRNA is transcribed from the cDNA and is subject to in vitro translation, the mRNA will still be attached to the ribosome and mRNA, forming the ARM complex. The library of humanized antibody that is translated from the cDNA gene pool and displayed on the surface of the ribosome can be screened against a specific target antigen. The in vitro transcription and translation of this library may be carried out in rabbit reticulocyte lysate in the presence of methionine at 30° C. by using the commercially available systems, such as TNT T7 Quick Coupled Transcription/Translation System (Promega, Madison, Wis.).

The specific target antigen may be any molecule, including, but not limited to, biomacromolecules such as protein, DNA, RNA, polycarbohydrate or small molecules such as peptide, organic compound and organometallic complexes. Preferably, the target antigen is immobilized to a solid substrate, such as a chromatography resin by covalent linkage to enrich for those ribosomes with high affinity humanized antibody attached. By affinity chromatography, the ribosomes with high affinity humanized antibody attached are isolated. The mRNA encoding the high affinity humanized antibody is recovered from the isolated ARM complexes and subject to reverse transcriptase (RT)/PCR to synthesize and amplify the cDNA of the selected antibody. This completes the first cycle of the panning process for antibody isolation and its coding sequence characterization.

Such a panning process may be repeated until humanized antibody with desirably affinity is isolated. Specifically, the sequence encoding the selected humanized antibody in the first cycle may be mutagenized to generate a secondary library of humanized antibody sequences which are subject to another cycle of ribosome display panning. The mutagenesis may be carried out simultaneously in the RT/PCR step, which not only synthesizes the cDNA but also mutagenizes the cDNA randomly, e.g., by error-prone PCR. This secondary library of humanized antibody sequences are then transcribed and translated in vitro following similar steps for the first round of selection. The library of humanized antibody displayed on the ARM complexes are subject to the second round of screening against the same target antigen to select for humanized antibody with higher affinity than the one(s) selected from the first round of selection. The whole panning process can be reiterated to produce humanized antibody with perhaps much higher affinity than the original non-human antibody from which the first library of humanized antibody is derived.

4. Screening of a Library of Humanized Antibody by mRNA Display

The present invention also provides methods for screening a library of humanized antibody against a specific target antigen via mRNA display in vitro.

Similar to ribosome display described above, mRNA display is a form of protein display for in vitro selection against a target ligand. In this system, mRNA encoding the tester protein (e.g. an antibody) and the translated tester protein are associated through covalent linkage. Keefe and Szostak (2001) "Functional proteins from a random-sequence library" Nature 410:715-718; Wilson et al. (2001) "The use of mRNA display to select high-affinity protein-binding peptides" Proc Natl Acad Sci USA 98:3750-3755; Cho et al. (2000) "Constructing high complexity synthetic libraries of long ORFs using in vitro selection" J Mol Biol. 297:309-319; and Roberts and Szostak (1997) "RNA-peptide fusions for the in vitro selection of peptides and proteins" Proc Natl Acad Sci U S A. 94:12297-12302. The in vitro translated protein is covalently linked at its C-terminus to the 3' end of its encoding mRNA by a peptidyl acceptor linker such as the antibiotic puromycin. Specifically, in the translation reaction, puromycin enters the "A" site of ribosomes and forms a covalent bond with the nascent peptide at the C-terminus. Such a covalently associated mRNA-protein complex can be selected for its binding affinity toward a target ligand in vitro. After RT-PCR cDNA encoding the binding protein can be amplified and identified.

Figure 12:
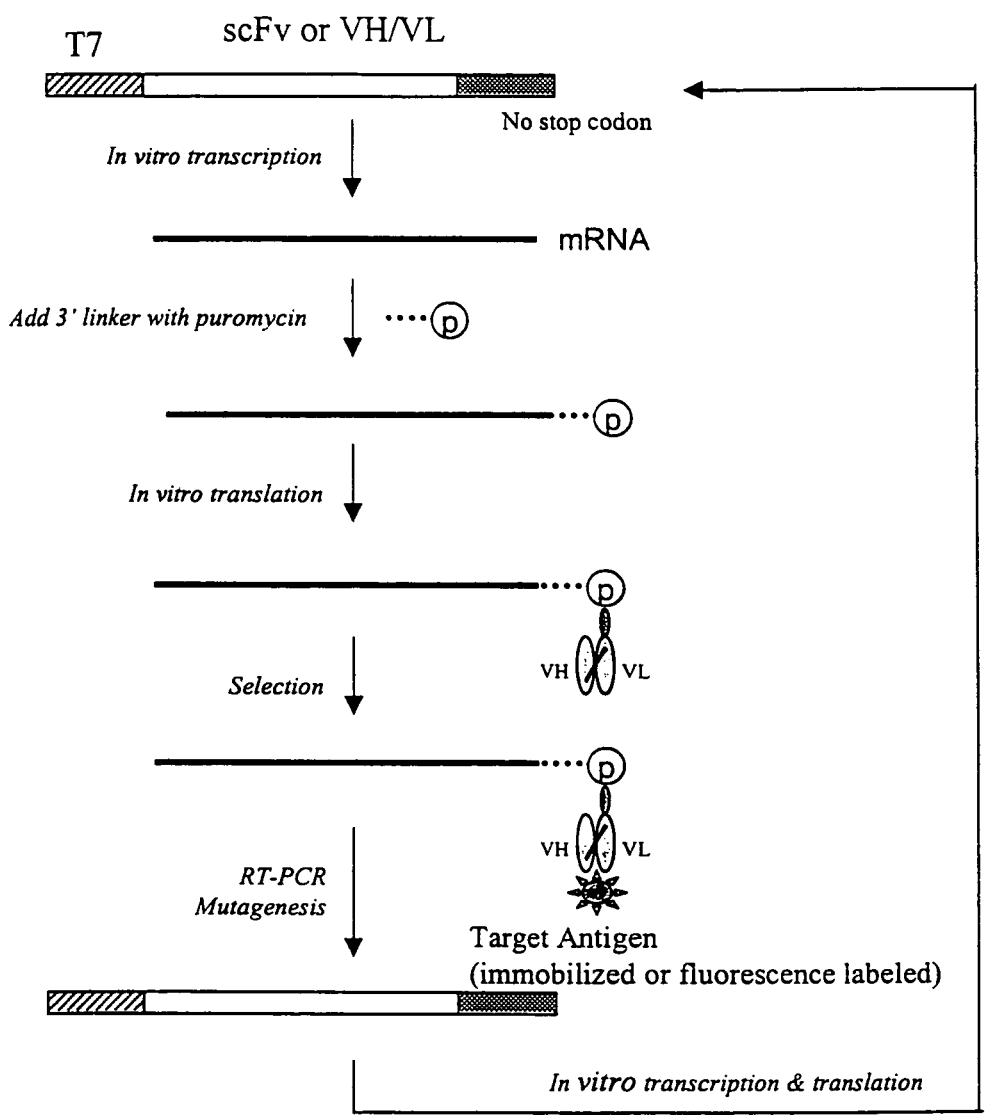
FIG. 12 illustrates an embodiment of the method for selecting humanized antibody against a target antigen through mRNA display.

FIG. 12 illustrates a method of the present invention used for screening the library of humanized antibody sequences constructed in Section 1 via mRNA display. As illustrated in FIG. 12, each member of the library of humanized antibody sequences for mRNA display includes a bacterial phage T7 promoter and protein synthesis initiation sequence attached to the 5' end of the cDNA encoding the antibody (e.g., scFv, $V_H$ or $V_L$) and no stop codon in the 3' end. A peptidyl acceptor linker such as puromycin is added to the in vitro transcribed mRNA library to react with the 3'-end of the mRNA. The in vitro transcription and translation of this library may be carried out in rabbit reticulocyte lysate in the presence of methionine at 30° C. by using the commercially available systems, such as TNT T7 Quick Coupled Transcription/Translation System (Promega, Madison, Wis.).

The nascent protein translated from the 3'-end modified mRNA pool reacts with puromycin at its C-terminus to form the covalently bound mRNA-antibody complex.

Still referring to FIG. 12, the library of antibody displayed linked to its encoding mRNA can be screened against a specific target antigen.

The specific target antigen may be any molecule, including, but not limited to, biomacromolecules such as protein, DNA, RNA, polycarbohydrate or small molecules such as peptide, organic compound and organometallic complexes. Preferably, the target antigen is immobilized to a solid substrate, such as a chromatography resin by covalent linkage to enrich for those ribosomes with high affinity humanized antibody attached. By affinity chromatography, the mRNA-antibody complexes with high affinity toward the target antigen are isolated. The mRNA encoding the high affinity humanized antibody is recovered from the isolated mRNA-Antibody complexes and subject to reverse transcriptase (RT)/PCR to synthesize and amplify the cDNA of the selected antibody. This completes the first cycle of the panning process for antibody isolation and its coding sequence characterization.

Such a panning process may be repeated until humanized antibody with desirably affinity is isolated. Specifically, the sequence encoding the selected humanized antibody in the first cycle may be mutagenized to generate a secondary library of humanized antibody sequences which are subject to another cycle of ribosome display panning. The mutagenesis may be carried out simultaneously in the RT/PCR step, which not only synthesizes the cDNA but also mutagenizes the cDNA randomly, e.g., by error-prone PCR. This secondary library of humanized antibody sequences are then transcribed and translated in vitro following similar steps for the first round of selection. The library of humanized antibody displayed on the mRNA-Antibody complexes are subject to the second round of screening against the same target antigen to select for humanized antibody with higher affinity than the one(s) selected from the first round of selection. The whole panning process can be reiterated to produce humanized antibody with perhaps much higher affinity than the original non-human antibody from which the first library of humanized antibody is derived.

5. Mutagenesis of the Humanized Antibody Leads Positively Selected Against a Target Antigen—Affinity Maturation As described above, humanized antibody leads, such as scFv or dsFv, can be identified through selection of the primary library carrying humanized antibody against a specific target antigen. The coding sequences of these humanized antibody leads may be mutagenized in vitro or in vivo to generated a secondary library more diverse than these leads. The mutagenized leads can be selected against the target antigen again in vivo following similar procedures described for the selection of the primary library carrying humanized antibody. Such mutagenesis and selection of primary humanized antibody leads effectively mimics the affinity maturation process naturally occurring in a mammal that produces antibody with progressive increase in the affinity to the immunizing antigen.

The coding sequences of the humanized antibody leads may be mutagenized by using a wide variety of methods. Examples of methods of mutagenesis include, but are not limited to site-directed mutagenesis, error-prone PCR mutagenesis, cassette mutagenesis, random PCR mutagenesis, DNA shuffling, and chain shuffling.

Site-directed mutagenesis or point mutagenesis may be used to gradually the humanized antibody sequences in specific regions. This is generally accomplished by using oligonucleotide-directed mutagenesis. For example, a short sequence of an antibody lead may be replaced with a synthetically mutagenized oligonucleotide in either the heavy chain or light chain region or both. The method may not be efficient for mutagenizing large numbers of humanized antibody sequences, but may be used for fine toning of a particular lead to achieve higher affinity toward a specific target protein.

Cassette mutagenesis may also be used to mutagenize the humanized antibody sequences in specific regions. In a typical cassette mutagenesis, a sequence block, or a region, of a single template is replaced by a completely or partially randomized sequence. However, the maximum information content that can be obtained may be statistically limited by the number of random sequences of the oligonucleotides. Similar to point mutagenesis, this method may also be used for fine toning of a particular lead to achieve higher affinity toward a specific target protein.

Error-prone PCR, or "poison" PCR, may be used to the humanized antibody sequences by following protocols described in Caldwell and Joyce (1992) PCR Methods and Applications 2:28-33. Leung, D. W. et al. (1989) Technique 1: 11-15. Shafikhani, S. et al. (1997) Biotechniques 23:304-306. Stemmer, W. P. et al. (1994) Proc. Natl. Acad. Sci. USA 91:10747-10751.

Figure 13:
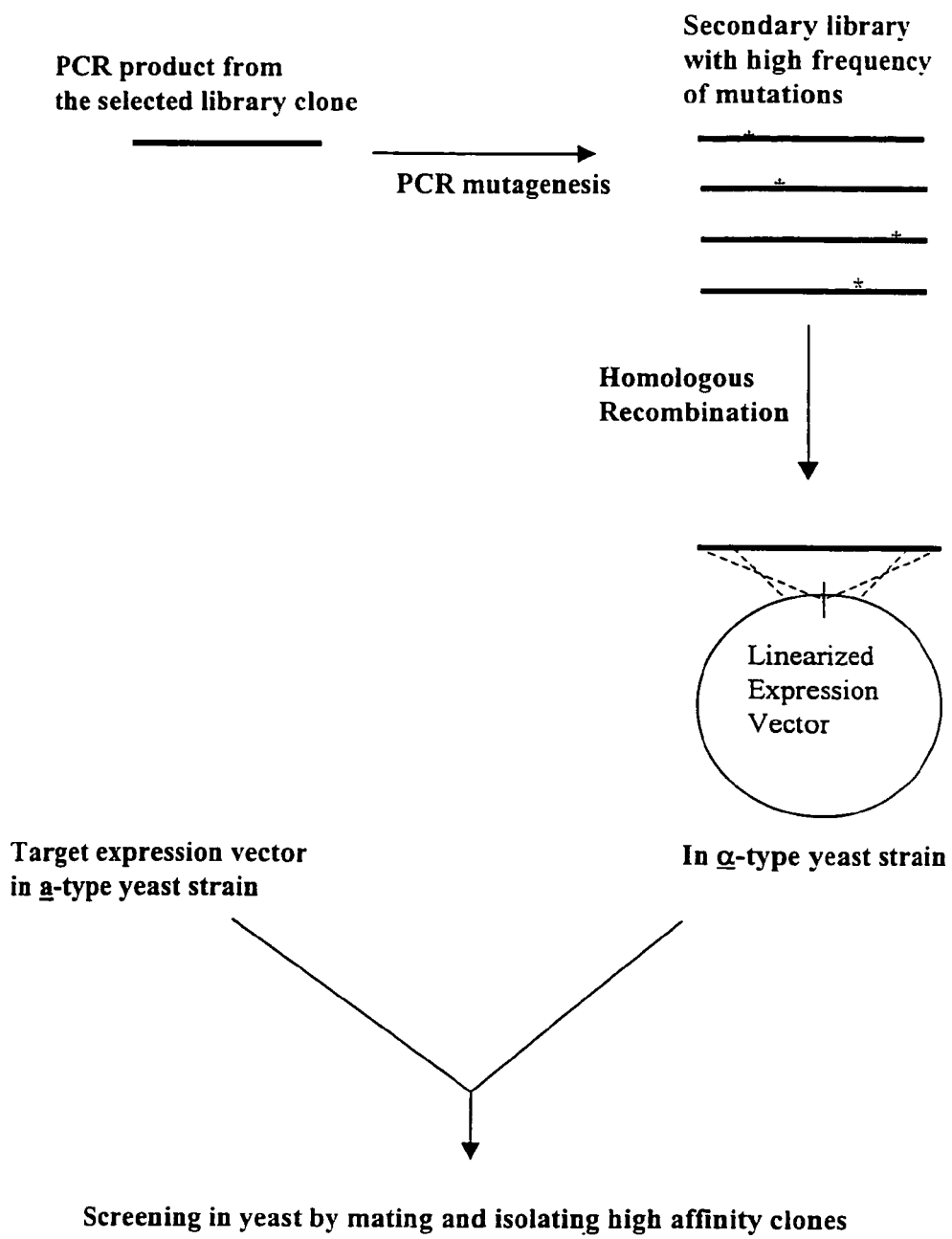
FIG. 13 illustrates an embodiment of the method used for mutagenesis and further screening of the clones selected from a primary screening of the humanized antibody in yeast.

FIG. 13 illustrates an example of the method of the present invention for affinity maturation of humanized antibody leads selected from the primary antibody library. As illustrated in FIG. 13, the coding sequences of the humanized antibody leads selected from clones containing the primary library are mutagenized by using a poison PCR method. Since the coding sequences of the humanized antibody library are contained in the expression vectors isolated from the selected clones, one or more pairs of PCR primers may be used to specifically amplify the $V_H$ and $V_L$ region out of the vector. The PCR fragments containing the $V_H$ and $V_L$ sequences are mutagenized by the poison PCR under conditions that favors incorporation of mutations into the product.

Such conditions for poison PCR may include a) high concentrations of $Mn^{2+}$ (e.g. 0.4-0.6 mM) that efficiently induces malfunction of Taq DNA polymerase; and b) disproportionally high concentration of one nucleotide substrate (e.g., dGTP) in the PCR reaction that causes incorrect incorporation of this high concentration substrate into the template and produce mutations. Additionally, other factors such as, the number of PCR cycles, the species of DNA polymerase used, and the length of the template, may affect the rate of mis-incorporation of "wrong" nucleotides into the PCR product. Commercially available kits may be utilized for the mutagenesis of the selected antibody library, such as the "Diversity PCR random mutagenesis kit" (catalog No. K1830-1, Clontech, Palo Alto, Calif.).

The PCR primer pairs used in mutagenesis PCR may preferably include regions matched with the homologous recombination sites in the expression vectors. This design allows re-introduction of the PCR products after mutagenesis back into the yeast host strain again via homologous recombination. This also allows the modified $V_H$ or $V_L$ region to be fused with the AD domain directly in the expression vector in the yeast.

Still referring to FIG. 13, the mutagenized scFv fragments are inserted into the expression vector containing an AD domain via homologous recombination in haploid cells of α type yeast strain. Similarly to the selection of antibody clones from the primary antibody library, the AD-scFv containing haploid cells are mated with haploid cells of opposite mating type (e.g. a type) that contains the BD-Target vector and the reporter gene construct. The parental diploid cells are selected based on expression of the reporter gene and other selection criteria as described in detail in Section 2.

Other PCR-based mutagenesis method can also be used, alone or in conjunction with the poison PCR described above. For example, the PCR amplified $V_H$ and $V_L$ segments may be digested with DNase to create nicks in the double DNA strand. These nicks can be expanded into gaps by other exonucleases such as Bal 31. The gaps may be then be filled by random sequences by using DNA Klenow polymerase at low concentration of regular substrates dGTP, dATP, dTTP, and dCTP with one substrate (e.g., dGTP) at a disproportionately high concentration. This fill-in reaction should produce high frequency mutations in the filled gap regions. These method of DNase I digestion may be used in conjunction with poison PCR to create highest frequency of mutations in the desired $V_H$ and $V_L$ segments.

The PCR amplified $V_H$ and $V_L$ segments or antibody heavy chain and light chain segments may be mutagenized in vitro by using DNA shuffling techniques described by Stemmer (1994) Nature 370:389-391; and Stemmer (1994) Proc. Natl. Acad. Sci. USA 91:10747-10751. The $V_H$, $V_L$ or antibody segments from the primary antibody leads are digested with DNase I into random fragments which are then reassembled to their original size by homologous recombination in vitro by using PCR methods. As a result, the diversity of the library of primary antibody leads are increased as the numbers of cycles of molecular evolution increase in vitro.

The $V_H$, $V_L$ or antibody segments amplified from the primary antibody leads may also be mutagenized in vivo by exploiting the inherent ability of mution in pre-B cells. The Ig gene in pre-B cells is specifically susceptible to a high-rate of mutation in the development of pre-B cells. The Ig promoter and enhancer facilitate such high rate mutations in a pre-B cell environment while the pre-B cells proliferate. Accordingly, $V_H$ and $V_L$ gene segments may be cloned into a mammalian expression vector that contains human Ig enhancer and promoter. This construct may be introduced into a pre-B cell line, such as 38B9, which allows the mutation of the $V_H$ and $V_L$ gene segments naturally in the pre-B cells. Liu, X., and Van Ness, B. (1999) Mol. Immunol. 36:461-469. The mutagenized $V_H$ and $V_L$ segments can be amplified from the cultured pre-B cell line and re-introduced back into the AD-containing yeast strain via, for example, homologous recombination.

The secondary antibody library produced by mutagenesis in vitro (e.g. PCR) or in vivo, i.e., by passing through a mammalian pre-B cell line may be cloned into an expression vector and screened against the same target protein as in the first round of screening using the primary antibody library. For example, the expression vectors containing the secondary antibody library may be transformed into haploid cells of α type yeast strain. These α cells are mated with haploid cells a type yeast strain containing the BD-target expression vector and the reporter gene construct. The positive interaction of antibodies from the secondary antibody library is screened by following similar procedures as described for the selection of the primary antibody leads in yeast.

6. Functional Expression and Purification of Selected Antibody

The humanized antibodies that are generated and selected in the screening against the target antigen may be functionally expressed in hosts after the $V_H$ and $V_L$ sequences are operably linked to an expression control DNA sequence, including naturally-associated or heterologous promoters, in an expression vector. By operably linking the $V_H$ and $V_L$ sequences to an expression control sequence, the $V_H$ and $V_L$ coding sequences are positioned to ensure the transcription and translation of these inserted sequences. The expression vector may be replicable in the host organism as episomes or as an integral part of the host chromosomal DNA. The expression vector may also contain selection markers such as antibiotic resistance genes (e.g. neomycin and tetracycline resistance genes) to permit detection of those cells transformed with the expression vector.

Preferably, the expression vector may be a eukaryotic vector capable of transforming or transfecting eukaryotic host cells. Once the expression vector has been incorporated into the appropriate host cells, the host cells are maintained under conditions suitable for high level expression of humanized antibody or fragments, such as dcFv, Fab and antibody. The polypeptides expressed are collected and purified depending on the expression system used.

The dcFv, Fab, or fully assembled antibodies selected by using the methods of the present invention may be expressed in various scales in any host system. Examples of host systems include, but are not limited to, bacteria (e.g. *E. coli*), yeast (e.g. *S. cerevisiae*), and mammalian cells (COS). The bacteria expression vector may preferably contain the bacterial phage T7 promoter and express either the heavy chain and/or light chain region of the selected antibody. The yeast expression vector may contain a constitutive promoter (e.g. ADGI promoter) or an inducible promoter such as (e.g. GCN4 and Gal 1 promoters). All three types of antibody, dcFv, Fab, and full antibody, may be expressed in a yeast expression system.

The expression vector may be a mammalian express vector that can be used to express the humanized antibody in mammalian cell culture transiently or stably. Examples of mammalian cell lines that may be suitable of secreting immunoglobulins include, but are not limited to, various COS cell lines, HeLa cells, myeloma cell lines, CHO cell lines, transformed B-cells and hybridomas.

Typically, a mammalian expression vector includes certain expression control sequences, such as an origin of replication, a promoter, an enhancer, as well as necessary processing signals, such as ribosome binding sites, RNA splice sites, polyadenylation sites, and transcriptional terminator sequences. Examples of promoters include, but are not limited to, insulin promoter, human cytomegalovirus (CMV) promoter and its early promoter, simian virus SV40 promoter, Rous sarcoma virus LTR promoter/enhancer, the chicken cytoplasmic β-actin promoter, promoters derived from immunoglobulin genes, bovine papilloma virus and adenovirus.

One or more enhancer sequence may be included in the expression vector to increase the transcription efficiency. Enhancers are cis-acting sequences of between 10 to 300 bp that increase transcription by a promoter. Enhancers can effectively increase transcription when positioned either 5' or 3' to the transcription unit. They may also be effective if located within an intron or within the coding sequence itself. Examples of enhancers include, but are not limited to, SV40 enhancers, cytomegalovirus enhancers, polyoma enhancers, the mouse immunoglobulin heavy chain enhancer and adenovirus enhancers. The mammalian expression vector may also typically include a selectable marker gene. Examples of suitable markers include, but are not limited to, the dihydrofolate reductase gene (DHFR), the thymidine kinase gene (TK), or prokaryotic genes conferring antibiotic resistance. The DHFR and TK genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The expression vectors containing the humanized antibody sequences can then be transferred into the host cell by methods known in the art, depending on the type of host cells. Examples of transfection techniques include, but are not limited to, calcium phosphate transfection, calcium chloride transfection, lipofection, electroporation, and microinjection.

The humanized antibody sequences may also be inserted into a viral vector such as adenoviral vector that can replicate in its host cell and produce the antibody in large amounts.

In particular, the dcFv, Fab, or fully assembled antibody may be expressed in mammalian cells by using a method described by Persic et al. (1997) Gene, 187:9-18. The mammalian expression vector that is described by Persic and contains EF-α promoter and SV40 replication origin is preferably utilized. The SV40 origin allows a high level of transient expression in cells containing large T antigen such as COS cell line. The expression vector may also include secretion signal and different antibiotic markers (e.g. neo and hygro) for integration selection.

Once expressed, the humanized antibody may be isolated and purified by using standard procedures of the art, including ammonium sulfate precipitation, fraction column chromatography, and gel electrophoresis. Once purified, partially or to homogeneity as desired, the polypeptides may then be used therapeutically or in developing, performing assay procedures, immunofluorescent staining, and in other biomedical and industrial applications. In particular, the antibodies generated by the method of the present invention may be used for diagnosis and therapy for the treatment of various diseases such as cancer, autoimmune diseases, or viral infections.

In a preferred embodiment, the humanized antibodies that are generated and screened by using the methods of the present invention may be expressed directly in yeast. According to this embodiment, the heavy chain and light chain regions from the selected expression vectors may be PCR amplified with primers that simultaneously add appropriate homologous recombination sequences to the PCR products. These PCR segments of heavy chain and light chain may then be introduced into a yeast strain together with a linearized expression vector containing desirable promoters, expression tags and other transcriptional or translational signals.

For example, the PCR segments of heavy chain and light chain regions may be homologously recombined with a yeast expression vector that already contains a desirable promoter in the upstream and stop codons and transcription termination signal in the downstream. The promoter may be a constitutive expression promoter such as ADH1, or an inducible expression promoter, such as Gal 1, or GCN4 (A. Mimran, I. Marbach, and D. Engelberg, (2000) Biotechniques 28:552-560). The latter inducible promoter may be preferred because the induction can be easily achieved by adding 3-AT into the medium.

The yeast expression vector to be used for expression of the antibody may be of any standard strain with nutritional selection markers, such as His 3, Ade 2, Leu 2, Ura 3, Trp 1 and Lys 2. The marker used for the expression of the selected antibody may preferably be different from the AD vector used in the selection of antibody in the two-hybrid system. This may help to avoid potential carryover problem associated with multiple yeast expression vectors.

For expressing the dcFv antibody in a secreted form in yeast, the expression vector may include a secretion signal in the 5' end of the $V_H$ and $V_L$ segments of the humanized antibody, such as an alpha factor signal and a 5-pho secretion signal. Certain commercially available vectors that contain a desirable secretion signal may also be used (e.g., pYEX-S1, catalog # 6200-1, Clontech, Palo Alto, Calif.).

The dcFv antibody fragments generated may be analyzed and characterized for their affinity and specificity by using methods known in the art, such as ELISA, western, and immune staining. Those dcFv antibody fragments with reasonably good affinity (with dissociation constant preferably above $10^{-6}$ M) and specificity can be used as building blocks in Fab expression vectors, or can be further assembled with the constant region for full length antibody expression. These fully assembled human antibodies may also be expressed in yeast in a secreted form.

The $V_H$ sequence encoding the selected dcFv protein may be linked with the constant regions of a full antibody, $C_H1$, $C_H2$ and $C_H3$. Similarly, the $V_L$ sequence may be linked with the constant region $C_L$. The assembly of two units of $V_H$-$C_H1$-$C_H2$-$C_H3$ and $V_L$-$C_L$ leads to formation of a fully functional antibody.

The present invention provides a method for producing fully functional humanized antibody in yeast. Fully functional antibody retaining the rest of the constant regions may have a higher affinity (or avidity) than a dcFv or a Fab. The full antibody should also have a higher stability, thus allowing more efficient purification of antibody protein in large scale.

The method is provided by exploiting the ability of yeast cells to uptake and maintain multiple copies of plasmids of the same replication origin. According to the method, different vectors may be used to express the heavy chain and light chain separately, and yet allows for the assembly of a fully functional antibody in yeast. This approach has been successfully used in a two-hybrid system design where the BD and AD vectors are identical in backbone structure except the selection markers are distinct. This approach has been used in a two-hybrid system design for expressing both BD and AD fusion proteins in the yeast. The BD and AD vectors are identical in their backbone structures except the selection markers are distinct. Both vectors can be maintained in yeast in high copy numbers. Chien, C. T., et al. (1991) "The two-hybrid system: a method to identify and clone genes for proteins that interact with a protein of interest" Proc. Natl. Acad. Sci. USA 88:9578-9582.

In the present invention, the heavy chain gene and light chain genes are placed in two different vectors. Under a suitable condition, the $V_H$-$C_H1$-$C_H2$-$C_H3$ and $V_L$-$C_L$ sequences are expressed and assembled in yeast, resulting in a fully functional antibody protein with two heavy chains and two light chains. This fully functional antibody may be secreted into the medium and purified directly from the supernatant.

The dcFv with a constant region, Fab, or fully assembled antibody can be purified using methods known in the art. Conventional techniques include, but are not limited to, precipitation with ammonium sulfate and/or caprylic acid, ion exchange chromatography (e.g. DEAE), and gel filtration chromatography. Delves (1997) "Antibody Production: Essential Techniques", New York, John Wiley & Sons, pages 90-113. Affinity-based approaches using affinity matrix based on Protein A, Protein G or Protein L may be more efficiency and results in antibody with high purity. Protein A and protein G are bacterial cell wall proteins that bind specifically and tightly to a domain of the Fc portion of certain immunoglobulins with differential binding affinity to different subclasses of IgG. For example, Protein G has higher affinities for mouse IgG1 and human IgG3 than does Protein A. The affinity of Protein A of IgG1 can be enhanced by a number of different methods, including the use of binding buffers with increased pH or salt concentration. Protein L binds antibodies predominantly through kappa light chain interactions without interfering with the antigen-binding site. Chateau et al. (1993) "On the interaction between Protein L and immunoglobulins of various mammalian species" Scandinavian J. Immunol., 37:399-405. Protein L has been shown to bind strongly to human kappa light chain subclasses I, III and IV and to mouse kappa chain subclasses I. Protein L can be used to purify relevant kappa chain-bearing antibodies of all classes (IgG, IgM, IgA, IgD, and IgE) from a wide variety of species, including human, mouse, rat, and rabbit. Protein L can also be used for the affinity purification of scFv and Fab antibody fragments containing suitable kappa light chains. Protein L-based reagents is commercially available from Actigen, Inc., Cambridge, England. Actigen can provide a line of recombinant Protein products, including agarose conjugates for affinity purification and immobilized forms of recombinant Protein L and A fusion protein which contains four protein A antibody-binding domains and four protein L kappa-binding domains.

Other affinity matrix may also be used, including those that exploit peptidomimetic ligands, anti-immunoglobulins, mannan binding protein, and the relevant antigen. Peptidomimetic ligands resemble peptides but they do not correspond to natural peptides. Many of Peptidomimetic ligands contain unnatural or chemically modified amino acids. For example, peptidomimetic ligands designed for the affinity purification of antibodies of the IGA and IgE classes are commercially available from Tecnogen, Piana di Monte Vema, Italy. Mannan binding protein (MBP) is a mannose- and N-acetylglucosamine-specific lectin found in mammalian sera. This lectin binds IgM. The MBP-agarose support for the purification IgM is commercially available from Pierce.

Immunomagnetic methods that combine an affinity reagent (e.g. protein A or an anti-immunoglobulin) with the ease of separation conferred by paramagnetic beads may be used for purifying the antibody produced. Magnetic beads coated with Protein or relevant secondary antibody may be commercially available from Dynal, Inc., New York; Bangs Laboratories, Fishers, Ind.; and Cortex Biochem Inc., San Leandro, Calif.

Direct expression and purification of the selected antibody in yeast is advantageous in various aspects. As a eukaryotic organism, yeast is more of an ideal system for expressing human proteins than bacteria or other lower organisms. It is more likely that yeast will make the dcFv, Fab, or fully assembled antibody in a correct conformation (folded correctly), and will add post-translation modifications such as correct disulfide bond(s) and glycosylations.

Yeast has been explored for expressing many human proteins in the past. Many human proteins have been successfully produced from the yeast, such as human serum albumin (Kang, H. A. et al. (2000) Appl. Microbiol. Biotechnol. 53:578-582) and human telomerase protein and RNA complex (Bachand, F., et al. (2000) RNA 6:778-784).

Yeast has fully characterized secretion pathways. The genetics and biochemistry of many if not all genes that regulate the pathways have been identified. Knowledge of these pathways should aid in the design of expression vectors and procedures for isolation and purification of antibody expressed in the yeast.

Moreover, yeast has very few secreted proteases. This should keep the secreted recombinant protein quite stable. In addition, since yeast does not secrete many other and/or toxic proteins, the supernatant should be relatively uncontaminated. Therefore, purification of recombinant protein from yeast supernatant should be simple, efficient and economical.

Additionally, simple and reliable methods have been developed for isolating proteins from yeast cells. Cid, V. J. et al. (1998) "A mutation in the Rho&GAP-encoding gene BEM2 of *Saccharomyces cerevisiae* affects morphogenesis and cell wall functionality" Microbiol. 144:25-36. Although yeast has a relatively thick cell wall that is not present in either bacterial or mammalian cells, the yeast cells can still keep the yeast strain growing with the yeast cell wall striped from the cells. By growing the yeast strain in yeast cells without the cell wall, secretion and purification of recombinant human antibody may be made more feasible and efficient.

By using yeast as host system for expression, a streamlined process can be established to produce recombinant antibodies in fully assembled and purified form. This may save tremendous time and efforts as compared to using any other systems such as humanization of antibody in vitro and production of fully human antibody in transgenic animals.

In summary, the compositions, kits and methods provided by the present invention should be very useful for humanized antibodies with high affinity and specificity against a wide variety of targets including, but not limited to, soluble proteins (e.g. growth factors, cytokines and chemokines), membrane-bound proteins (e.g. cell surface receptors), and viral antigens. The whole process of library construction, functional screening and expression of highly diverse repertoire of human antibodies can be streamlined, and efficiently and economically performed in yeast or displayed on ribosome in a high throughput and automated manner. The selected proteins can have a wide variety of applications. For example, they can be used in therapeutics and diagnosis of diseases including, but not limited to, autoimmune diseases, cancer, transplant rejection, infectious diseases and inflammation.

What is claimed is:

1. A method for screening a library of human or humanized antibodies in yeast, comprising:
    assembling a library of antibodies in yeast cells, wherein the step of assembling the library comprises:
        mutagenizing a $V_H$ and $V_L$ to produce a plurality of $V_H$ and $V_L$; and
        introducing the plurality of $V_H$ and $V_L$ into expression vectors by homologous recombination;
    expressing the library of human or humanized antibodies in the yeast cells, wherein each of the human or humanized antibodies comprises a $V_H$ and a $V_L$ which form a $V_H/V_L$ heterodimer in the yeast cells;
    contacting a specific target protein with the library of human or humanized antibodies expressed in the yeast cells; and
    selecting those human or humanized antibodies based on their binding to the target protein.

2. The method of claim 1, wherein a member of the library of humanized antibodies comprises:
    $V_H$ having 3 CDRs, wherein at least one of the CDRs is a CDR3 of a non-human $V_H$ grafted into a human antibody framework, and
    $V_L$ having 3 CDRs, wherein at least one of the CDRs is a CDR3 of a non-human $V_L$ grafted into a human antibody framework; wherein
    the one or more heavy chain CDR or CDRs and the one or more light chain CDR or CDRs are from the same non-human antibody, and the selected antibodies bind to the same target protein as the antibody from which the non-human CDRs are obtained.

3. The method of claim 1, wherein the library of humanized antibodies is generated by mutagenizing a chimeric antibody that comprises:
    $V_H$ having 3 CDRs, wherein at least one of the CDRs is a CDR3 of a non-human $V_H$ grafted into a human antibody framework, and
    $V_L$ having 3 CDRs, wherein at least one of the CDRs is a CDR3 of a non-human $V_L$ grafted into a human antibody framework, wherein
    the one or more heavy chain CDR or CDRs and the one or more light chain CDR or CDRs are from the same non-human antibody, and the selected antibodies bind to the same target protein as the antibody from which the non-human CDRs are obtained.

4. The method of claim 1, wherein the $V_H$ and the VL each is linked with a zipper domain by which the $V_H$ and the $V_L$ are associated with each other to form a heterodimer.

5. The method of claim 4, wherein the zipper domains of the $V_H$ and the $V_L$ facilitate the heterodimerization of the $V_H$ and the $V_L$ through coiled-coil interactions.

6. The method of claim 4, wherein the zipper domains of the $V_H$ and the $V_L$ are leucine zippers.

7. The method of claim 4, wherein the zipper domains of the $V_H$ and the $V_L$ are leucine zippers formed by the leucine zippers from Fos and Jun.

8. The method of claim 4, wherein the zipper domains of the $V_H$ and the $V_L$ are leucine zippers formed by the leucine zippers from Myc and Max.

9. The method of claim 4, wherein the zipper domains of the $V_H$ and the $V_L$ each is linked to the C-terminus of the $V_H$ and the $V_L$, respectively.

10. A method for screening a library of human or humanized antibodies in yeast, comprising:
  assembling a library of antibodies in yeast cells, wherein the step of assembling the library comprises:
    mutagenizing a $V_H$ and $V_L$ to produce a plurality of $V_H$ and $V_L$; and
    introducing the plurality of $V_H$ and $V_L$ into expression vectors by gap repair homologous recombination;
  expressing the library of human or humanized antibodies in the yeast cells, wherein each of the human or humanized antibodies comprises a $V_H$ and a $V_L$ which form a $V_H/V_L$ heterodimer in the yeast cells;
  contacting a specific target protein with the library of human or humanized antibodies expressed in the yeast cells; and
  selecting those human or humanized antibodies based on their binding to the target protein.

11. The method of claim 10, wherein a member of the library of humanized antibodies comprises:
  $V_H$ having 3 CDRs, wherein at least one of the CDRs is a CDR3 of a non-human $V_H$ grafted into a human antibody framework, and
  $V_L$ having 3 CDRs, wherein at least one of the CDRs is a CDR3 of a non-human $V_L$ grafted into a human antibody framework; wherein
  the one or more heavy chain CDR or CDRs and the one or more light chain CDR or CDRs are from the same non-human antibody, and the selected antibodies bind to the same target protein as the antibody from which the non-human CDRs are obtained.

12. The method of claim 10, wherein the library of humanized antibodies is generated by mutagenizing a chimeric antibody that comprises:
  $V_H$ having 3 CDRs, wherein at least one of the CDRs is a CDR3 of a non-human $V_H$ grafted into a human antibody framework, and
  $V_L$ having 3 CDRs, wherein at least one of the CDRs is a CDR3 of a non-human $V_L$ grafted into a human antibody framework, wherein
  the one or more heavy chain CDR or CDRs and the one or more light chain CDR or CDRs are from the same non-human antibody, and the selected antibodies bind to the same target protein as the antibody from which the non-human CDRs are obtained.

13. The method of claim 10, wherein the $V_H$ and the VL each is linked with a zipper domain by which the $V_H$ and the $V_L$ are associated with each other to form a heterodimer.

14. The method of claim 13, wherein the zipper domains of the $V_H$ and the $V_L$ facilitate the heterodimerization of the $V_H$ and the $V_L$ through coiled-coil interactions.

15. The method of claim 13, wherein the zipper domains of the $V_H$ and the $V_L$ are leucine zippers.

16. The method of claim 13, wherein the zipper domains of the $V_H$ and the $V_L$ are leucine zippers formed by the leucine zippers from Fos and Jun.

17. The method of claim 13, wherein the zipper domains of the $V_H$ and the $V_L$ are leucine zippers formed by the leucine zippers from Myc and Max.

18. The method of claim 13, wherein the zipper domains of the $V_H$ and the $V_L$ each is linked to the C-terminus of the $V_H$ and the $V_L$, respectively.

* * * * *

UNITED STATES PATENT AND TRADEMARK OFFICE
CERTIFICATE OF CORRECTION

PATENT NO. : 9,464,286 B2
APPLICATION NO. : 11/480037
DATED : October 11, 2016
INVENTOR(S) : Zhu et al.

Page 1 of 1

It is certified that error appears in the above-identified patent and that said Letters Patent is hereby corrected as shown below:

In the Claims

Column 45, Claim 4: Line 1, replace "VL" with "$V_L$"; and Line 2, delete the "-" where it currently recites, "by which the $Y_H$ and-the $V_L$";

Column 46, Claim 13: Line 1, replace "VL" with "$V_L$"; and Line 2, delete the "-" where it currently recites, "by which the $Y_H$ and-the".

Signed and Sealed this
Seventh Day of February, 2017

Michelle K. Lee
*Director of the United States Patent and Trademark Office*

SEQUENCE LISTING

<160> NUMBER OF SEQ ID NOS: 9

<210> SEQ ID NO 1
<211> LENGTH: 296
<212> TYPE: DNA
<213> ORGANISM: Artificial Sequence

```
<220> FEATURE:
<223> OTHER INFORMATION: Consensus human germline VH sequence (DP47)

<400> SEQUENCE: 1
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcagct attagtggta gtggtggtag cacatactac       180
gcagactccg tgaagggccg gttcaccatc tccagagaca attccaagaa cacgctgtat     240
ctgcaaatga acagcctgag agccgaggac acggccgtat attactgtgc gaaaga         296

<210> SEQ ID NO 2
<211> LENGTH: 290
<212> TYPE: DNA
<213> ORGANISM: Artificial Sequence
<220> FEATURE:
<223> OTHER INFORMATION: Consensus human germline VL sequence (DPK22)

<400> SEQUENCE: 2
gaaattgtgt tgacgcagtc tccaggcacc ctgtctttgt ctccagggga agagccacc      60 ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag   240
cctgaagatt ttgcagtgta ttactgtcag cagtatggta gctcacctcc                 290

<210> SEQ ID NO 3
<211> LENGTH: 5
<212> TYPE: PRT
<213> ORGANISM: Artificial Sequence
<220> FEATURE:
<223> OTHER INFORMATION: Single chain antibody linker sequence G4S

<400> SEQUENCE: 3

Gly Gly Gly Gly Ser
1               5

<210> SEQ ID NO 4
<211> LENGTH: 357
<212> TYPE: DNA
<213> ORGANISM: Mus musculus

<400> SEQUENCE: 4
caggtccagt tgcagcagtc tggagctgag tcggtaaggc ctggacttc agtgaagata      60 tcctgcaagg cttctggcta caccttcact aactactggc taggttgggt aaagcagagg    120
cctggacatg gacttgagtg gattggagat atttaccctg aggtggtta tactaactac     180 aatgagaagt tcaaggacaa ggccacactg acaacagaca catcctccag cactgcctac   240
atgcagctca gtagcctgac atctgatgac tctgctgtct atttctgtgc aagggactac   300
ggtagtaggt actactttga ctactgggc caaggcacca ctctcacagt ctcctca         357

<210> SEQ ID NO 5
<211> LENGTH: 119
<212> TYPE: PRT
<213> ORGANISM: Mus musculus

<400> SEQUENCE: 5

Gln Val Gln Leu Gln Gln Ser Gly Ala Glu Ser Val Arg Pro Gly Thr
1               5                   10                  15
```

```
Ser Val Lys Ile Ser Cys Lys Ala Ser Gly Tyr Thr Phe Thr Asn Tyr
                20                  25                  30

Trp Leu Gly Trp Val Lys Gln Arg Pro Gly His Gly Leu Glu Trp Ile
            35                  40                  45

Gly Asp Ile Tyr Pro Gly Gly Gly Tyr Thr Asn Tyr Asn Glu Lys Phe
50                  55                  60

Lys Asp Lys Ala Thr Leu Thr Thr Asp Thr Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Asp Tyr Gly Ser Arg Tyr Tyr Phe Asp Tyr Trp Gly Gln Gly
            100                 105                 110

Thr Thr Leu Thr Val Ser Ser
        115

<210> SEQ ID NO 6
<211> LENGTH: 321
<212> TYPE: DNA
<213> ORGANISM: Mus musculus

<400> SEQUENCE: 6
gatatccaga tgacacagac tacatcctcc ctgtctgcct ctctgggaga cagagtcacc      60
atcagttgca gggcaagtca ggacattagc aattttttaa actggtatca gcagaaacca     120
gatggaactg ttaaactcct gatctactac acatcaagat tacactcagg agtcccatca     180
aggttcagtg gcagtgggtc tggaacagat tattctctca ccattagcaa cctggaacaa     240
gaagatattg ccacttactt ttgccaacag ggtaacacgc tgtggacgtt cggtggaggc     300
accaagctgg aaatcaaacg g                                               321

<210> SEQ ID NO 7
<211> LENGTH: 107
<212> TYPE: PRT
<213> ORGANISM: Mus musculus

<400> SEQUENCE: 7

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Phe
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Trp Thr
                85                  90                  95

Phe Gly Gly Gly Thr Lys Leu Glu Ile Lys Arg
            100                 105

<210> SEQ ID NO 8
<211> LENGTH: 118
<212> TYPE: PRT
<213> ORGANISM: Homo sapiens

<400> SEQUENCE: 8

Gln Val Gln Leu Leu Glu Ser Gly Ala Glu Leu Val Arg Pro Gly Ala
```

```
                1               5                      10                         15
            Ser Val Lys Ile Ser Cys Lys Ala Ser Gly Tyr Ala Phe Ser Ser Ser
                            20                      25                      30

Trp Met Asn Trp Val Lys Gln Arg Pro Gly Gln Gly Leu Glu Trp Ile
                        35                      40                  45

Gly Arg Ile Tyr Pro Gly Asp Gly Asp Thr Asn Tyr Asn Gly Lys Phe
                    50                      55                  60

Lys Glu Ala Ala Thr Leu Thr Ala Asp Lys Ser Ser Ser Thr Ala Tyr
             65                     70                  75                  80

Met Gln Leu Ser Ser Leu Thr Ser Val Asp Ser Ala Val Tyr Ser Cys
                            85                      90                  95

Ala Arg Ser Glu Tyr Trp Gly Asn Tyr Trp Ala Met Asp Tyr Trp Gly
                            100                     105                 110

Gln Gly Thr Thr Val Thr
                        115

<210> SEQ ID NO 9
            <211> LENGTH: 107
            <212> TYPE: PRT
            <213> ORGANISM: Homo sapiens

<400> SEQUENCE: 9

Asp Ile Gln Met Thr Gln Ser Pro Ser Ser Leu Ser Ala Ser Val Gly
             1               5                      10                     15

Asp Arg Val Thr Ile Thr Cys Arg Ala Ser Gln Ser Ile Ser Ser Tyr
                            20                      25                  30

Leu Asn Trp Tyr Gln Gln Lys Pro Gly Lys Ala Pro Lys Leu Leu Ile
                        35                      40                  45

Tyr Ala Ala Ser Ser Leu Gln Ser Gly Val Pro Ser Arg Phe Ser Gly
                        50                      55                  60

Ser Gly Ser Gly Thr Asp Phe Thr Leu Thr Ile Ser Ser Leu Gln Pro
             65                     70                  75                      80

Glu Asp Phe Ala Thr Tyr Tyr Cys Gln Gln Ser Tyr Ser Thr Leu Thr
                            85                      90                  95

Phe Gly Gly Gly Thr Lys Val Glu Ile Lys Arg
                            100                     105
```